(12) United States Patent
Rodino-Klapac

(10) Patent No.: US 12,263,230 B2
(45) Date of Patent: Apr. 1, 2025

(54) GENE THERAPY FOR LIMB-GIRDLE MUSCULAR DYSTROPHY TYPE 2C

(71) Applicant: Research Institute at Nationwide Children's Hospital, Columbus, OH (US)

(72) Inventor: Louise R. Rodino-Klapac, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 1111 days.

(21) Appl. No.: 16/966,407

(22) PCT Filed: Jan. 30, 2019

(86) PCT No.: PCT/US2019/015779
§ 371 (c)(1),
(2) Date: Jul. 30, 2020

(87) PCT Pub. No.: WO2019/152474
PCT Pub. Date: Aug. 8, 2019

(65) Prior Publication Data
US 2020/0360534 A1 Nov. 19, 2020

Related U.S. Application Data

(60) Provisional application No. 62/624,616, filed on Jan. 31, 2018.

(51) Int. Cl.
*A61K 48/00* (2006.01)
*A61K 45/06* (2006.01)
(Continued)

(52) U.S. Cl.
CPC ........ *A61K 48/005* (2013.01); *A61K 48/0075* (2013.01); *A61P 21/00* (2018.01);
(Continued)

(58) Field of Classification Search
CPC .. A61K 48/005; A61K 48/0075; A61K 45/06; A61K 38/1709; A61P 21/00;
(Continued)

(56) References Cited

U.S. PATENT DOCUMENTS

| | | |
|---|---|---|
| 5,173,414 A | 12/1992 | Lebkowski et al. |
| 5,449,616 A | 9/1995 | Campbell et al. |

(Continued)

FOREIGN PATENT DOCUMENTS

| | | |
|---|---|---|
| EP | 0 127 839 A2 | 12/1984 |
| EP | 0 155 476 A | 9/1985 |

(Continued)

OTHER PUBLICATIONS

Johns Hopkins Medicine, 2023 (Types of Muscular Dystrophy and Neuromuscular diseases, p. 1-4) (Year: 2023).*

(Continued)

*Primary Examiner* — Anna Skibinsky
*Assistant Examiner* — Morgan Taylor Lindgren Baltzel
(74) *Attorney, Agent, or Firm* — Foley & Lardner LLP

(57) ABSTRACT

The disclosure relates to gene therapy vectors, such as AAV vectors, comprising a polynucleotide encoding γ-sarcoglycan (SGCG) and methods of using such gene therapy vectors to treat subjects suffering from a muscular dystrophy, e.g. limb girdle dystrophy type 2C (LGMD2C).

17 Claims, 16 Drawing Sheets

Specification includes a Sequence Listing.

(51) Int. Cl.
*A61P 21/00* (2006.01)
*C07K 14/47* (2006.01)
*C12N 15/86* (2006.01)

(52) U.S. Cl.
CPC .......... *C07K 14/4707* (2013.01); *C12N 15/86* (2013.01); *A61K 45/06* (2013.01)

(58) Field of Classification Search
CPC .................. C07K 14/4707; C12N 15/86; C12N 2800/22; C12N 2830/008; C12N 2830/42; C12N 2750/14143; A01K 2217/075; A01K 2227/105; A01K 2267/0306
See application file for complete search history.

(56) References Cited

U.S. PATENT DOCUMENTS

| | | | |
|---|---|---|---|
| 5,658,776 | A | 8/1997 | Flotte et al. |
| 5,672,694 | A | 9/1997 | Campbell et al. |
| 5,786,211 | A | 7/1998 | Johnson |
| 5,871,982 | A | 2/1999 | Wilson et al. |
| 6,204,059 | B1 | 3/2001 | Samulski et al. |
| 6,258,595 | B1 | 7/2001 | Gao et al. |
| 6,262,035 | B1 | 7/2001 | Campbell et al. |
| 6,566,118 | B1 | 5/2003 | Atkinson et al. |
| 6,632,800 | B1 | 10/2003 | Russell et al. |
| 7,282,199 | B2 | 10/2007 | Gao et al. |
| 7,790,449 | B2 | 9/2010 | Gao et al. |
| 7,883,858 | B2 | 2/2011 | Hood et al. |
| 9,061,059 | B2 | 6/2015 | Chakraborty et al. |
| 9,434,928 | B2 | 9/2016 | Mendell et al. |
| 10,105,453 | B2 | 10/2018 | Mendell et al. |
| 11,358,993 | B2 | 6/2022 | Rodino-Klapac et al. |
| 2001/0029040 | A1 | 10/2001 | Toyo-Oka |
| 2003/0225260 | A1 | 12/2003 | Snyder |
| 2006/0154250 | A1 | 7/2006 | Morris et al. |
| 2007/0099251 | A1 | 5/2007 | Zhang et al. |
| 2008/0249052 | A1 | 10/2008 | Duan et al. |
| 2009/0054823 | A1 | 2/2009 | Bridges et al. |
| 2009/0275107 | A1 | 11/2009 | Lock et al. |
| 2009/0280103 | A1 | 11/2009 | Flueck |
| 2010/0003218 | A1 | 1/2010 | Duan et al. |
| 2010/0008979 | A1 | 1/2010 | Tomatsu et al. |
| 2010/0026655 | A1 | 2/2010 | Harley |
| 2010/0075866 | A1 | 3/2010 | Hood et al. |
| 2010/0112694 | A1 | 5/2010 | Marban |
| 2010/0120627 | A1 | 5/2010 | Belouchi et al. |
| 2010/0247495 | A1 | 9/2010 | Ichim et al. |
| 2010/0266551 | A1 | 10/2010 | Richard et al. |
| 2011/0023139 | A1 | 1/2011 | Weinstein et al. |
| 2011/0053221 | A1 | 3/2011 | Chen et al. |
| 2011/0070210 | A1 | 3/2011 | Andrijauskas |
| 2011/0076744 | A1 | 3/2011 | Wright et al. |
| 2011/0082192 | A1 | 4/2011 | Milne et al. |
| 2011/0104120 | A1 | 5/2011 | Xiao et al. |
| 2011/0266551 | A1 | 11/2011 | Thompson et al. |
| 2011/0294193 | A1 | 12/2011 | Amalfitano et al. |
| 2011/0301226 | A1 | 12/2011 | Mendell et al. |
| 2012/0087862 | A1 | 4/2012 | Hood et al. |
| 2013/0171172 | A1 | 7/2013 | Richard et al. |
| 2014/0010861 | A1 | 1/2014 | Bancel et al. |
| 2014/0147432 | A1* | 5/2014 | Bancel .............. C07K 14/485 424/94.64 |
| 2014/0179770 | A1 | 6/2014 | Zhang et al. |
| 2014/0234255 | A1 | 8/2014 | Lai et al. |
| 2014/0249208 | A1 | 9/2014 | Chakraborty et al. |
| 2014/0256802 | A1 | 9/2014 | Boye et al. |
| 2014/0273231 | A1 | 9/2014 | Zhang et al. |
| 2014/0323956 | A1 | 10/2014 | Mendell et al. |
| 2015/0111955 | A1 | 4/2015 | High et al. |
| 2015/0125429 | A1 | 5/2015 | Perlingeiro et al. |
| 2015/0232883 | A1 | 8/2015 | Dahlman et al. |
| 2015/0238627 | A1 | 8/2015 | Leger et al. |
| 2016/0058890 | A1 | 3/2016 | Buj Bello et al. |
| 2018/0256752 | A1 | 9/2018 | Buj Bello et al. |
| 2019/0000998 | A1 | 1/2019 | Mendell et al. |
| 2019/0202880 | A1 | 7/2019 | Rodino-Klapac et al. |
| 2019/0343966 | A1 | 11/2019 | Wang et al. |
| 2020/0339960 | A1 | 10/2020 | Sahenk |
| 2021/0128749 | A1 | 5/2021 | Rodino-Klapac et al. |
| 2021/0393801 | A1 | 12/2021 | Rodino-Klapac et al. |

FOREIGN PATENT DOCUMENTS

| | | |
|---|---|---|
| EP | 2 859 896 A1 | 4/2015 |
| JP | 2006-121961 A | 5/2006 |
| WO | WO-95/03392 A1 | 2/1995 |
| WO | WO-95/13365 A1 | 5/1995 |
| WO | WO-95/13392 A1 | 5/1995 |
| WO | WO-96/17947 A1 | 6/1996 |
| WO | WO-97/06243 A1 | 2/1997 |
| WO | WO-97/08298 A1 | 3/1997 |
| WO | WO-97/09441 A2 | 3/1997 |
| WO | WO-97/21825 A1 | 6/1997 |
| WO | WO-98/09657 A2 | 3/1998 |
| WO | WO-99/01176 A1 | 1/1999 |
| WO | WO-99/11764 A2 | 3/1999 |
| WO | WO-99/43360 A1 | 9/1999 |
| WO | WO-01/83692 A2 | 11/2001 |
| WO | WO-02/053703 A2 | 7/2002 |
| WO | WO-03/074714 A1 | 9/2003 |
| WO | WO-2004/058146 A2 | 7/2004 |
| WO | WO-2007/057781 A2 | 5/2007 |
| WO | WO-2009/019505 A2 | 2/2009 |
| WO | WO-2009/054725 A2 | 4/2009 |
| WO | WO-2013/016352 A1 | 1/2013 |
| WO | WO-2013/078316 A1 | 5/2013 |
| WO | WO-2013/123503 A1 | 8/2013 |
| WO | WO-2013/151665 A2 | 10/2013 |
| WO | WO-2013/176772 A1 | 11/2013 |
| WO | WO-2014/037526 A1 | 3/2014 |
| WO | WO-2014/093622 A2 | 6/2014 |
| WO | WO-2014/093712 A1 | 6/2014 |
| WO | WO-2014/204725 A1 | 12/2014 |
| WO | WO-2015/018503 A1 | 2/2015 |
| WO | WO-2015/021457 A2 | 2/2015 |
| WO | WO-2015/110449 A1 | 7/2015 |
| WO | WO-2015/158749 A2 | 10/2015 |
| WO | WO-2015/197232 A1 | 12/2015 |
| WO | WO-2016/115543 A2 | 7/2016 |
| WO | WO-2017/087395 A1 | 5/2017 |
| WO | WO-2017/165859 A1 | 9/2017 |
| WO | WO-2017/180857 A1 | 10/2017 |
| WO | WO-2017/180976 A1 | 10/2017 |
| WO | WO-2017/181014 A1 | 10/2017 |
| WO | WO-2017/181015 A1 | 10/2017 |
| WO | WO-2017/221145 A1 | 12/2017 |
| WO | WO-2018/170408 A1 | 9/2018 |
| WO | WO-2019/012336 A1 | 1/2019 |
| WO | WO-2019/078916 A1 | 4/2019 |
| WO | WO-2019/118806 A1 | 6/2019 |
| WO | WO-2019/152474 A1 | 8/2019 |
| WO | WO-2019/195362 A1 | 10/2019 |
| WO | WO-2019/209777 A1 | 10/2019 |
| WO | WO-2019/245973 A1 | 12/2019 |
| WO | WO-2020/006458 A1 | 1/2020 |
| WO | WO-2020/123645 A1 | 6/2020 |
| WO | WO-2020/176614 A1 | 9/2020 |
| WO | WO-2021/035120 A1 | 2/2021 |
| WO | WO-2021/257655 A1 | 12/2021 |

OTHER PUBLICATIONS

NCBI, GenBank accession No. U34976.1 (Nov. 8, 1995), 2 pages.
Noguchi, S., "Human gamma-sarcoglycan mRNA, complete cds.", Nov. 8, 1995, Database Accession No. U34976.
Herson et al., A phase I trial of adeno-associated virus serotype 1-gamma-sarcoglycan gene therapy for limb girdle muscular type 2C, Brain, 2012, vol. 135, Pt 2, pp. 483-492.
International Search Report and Written Opinion for PCT/US2019/015779 dated Apr. 30, 2019, 14 pages.

(56) References Cited

OTHER PUBLICATIONS

McNally et al., Mild and Severe Muscular Dystrophy Caused by a Single gamma-Sarcoglycan Mutation, American Journal of Human Genetics, Nov. 1996, vol. 59, No. 5, pp. 1040-1047.
Cordier et al., "Muscle-Specific Promoters May Be Necessary for Adeno-Associated Virus-Mediated Gene Transfer in the Treatment of Muscular Dystrophies," Human Gene Therapy, Jan. 20, 2001, vol. 12, pp. 205-215.
Cordier et al., "Rescue of Skeletal Muscles of gamma-Sarcoglycan-Deficient Mice with Adeno-Associated Virus-Mediated Gene Transfer," Molecular Therapy, Feb. 2000, vol. 1, No. 2 pp. 119-129.
Inouye et al., "Codon optimization of genes for efficient protein expression in mammalian cells by selection of only preferred human codons," Protein Expression and Purification, 2015, vol. 109, pp. 47-54.
Pozsgai et al., "Systemic AAV-Mediated [beta]-Sarcoglycan Delivery Targeting Cardiac and Skeletal Muscle Ameliorates Histological and Functional Deficits in LGMD2E Mice," Molecular Therapy, The Journal of the American Society of Gene Therapy, 25(4):855-869 (Apr. 2017).
Pozsgai et al., "Beta-Sarcoglycan gene transfer decreases fibrosis and restores force in LGMD2E mice," Gene Therapy, 2016, 23, pp. 57-66.
Abadi et al., Supplementation with alpha-lipoic acid, CoQ10, and vitamin E augments running performance and mitochondrial function in female mice, PLoS One, 8(4):e60722 (2013).
ABSS (Sequence Alignment; WO2020006458, SEQ ID #1; accessed Mar. 12, 2024) (Year: 2024).
ABSS2 (Sequence Alignment; U.S. Appl. No. 17/255,488, SEQ ID #1; accessed Mar. 12, 2024) (Year: 2024).
Allamand et al., Early adenovirus-mediated gene transfer effectively prevents muscular dystrophy in alpha-sarcoglycan-deficient mice, Gene Ther., 7(16):1385-91 (2000).
Anderson et al., "Nucleic acid hybridisation: A practical approach," Ch. 4, IRL Press Limited, Oxford, England (1 page) 1985.
Anderson et al., "Quantitative Filter Hybridisation—Chapter 4", Nucleic acid hyridisation a practical approach, 1985, pp. 73-111.
Angelini et al., The clinical spectrum of sarcoglycanopathies, Neurology, 52:176-179 (1999).
Araishi et al., Loss of the sarcoglycan complex and sarcospan leads to muscular dystrophy in beta-sarcoglycan-deficient mice, Hum. Mal. Genet. 8: 1589-1598 (1999).
Arnold et al., Electrophysiological Biomarkers in Spinal Muscular Atrophy: Preclinical Proof of Concept, Ann. Clin. Transl. Neural., 1 (1):34-44 (Jan. 2014).
Asokan et al., The AAV Vector Toolkit: Poised at the Clinical Crossroads; Molecular Therapy, 20(4):699-708 (2012).
Au et al., "Gene therapy advances: a meta-analysis of AAV Usage in Clinical Settings," Frontiers in Medicine, Feb. 9, 2022, vol. 8 (pp. 1-14).
Bang et al., The complete gene sequence of titin, expression of an unusual approximately 700-kDa titin isoform, and its interaction with obscurin identify a novel Z-line to I-band linking system, Gire. Res. 89:1065-72 (2001).
Barresi et al., Disruption of heart sarcoglycan complex and severe cardiomyopathy caused by beta sarcoglycan Nmutations, J. Med. Genet. 37: 102-107 (2000).
Bartoli et al., "Safety and efficacy of AAV-mediated calpain 3 gene transfer in a mouse model of limb-girdle muscular dystrophy type 2A", Mol. Ther., 13(2):250-259 (2006).
Bearzi et al., Human cardiac stem cells, Proc. Natl. Acad. Sci. USA. 104:14068-73 (2007).
Beastrom et al., mdx(5cv) mice manifest more severe muscle dysfunction and diaphragm force deficits than do mdx Mice, Am. J. Pathol., 179(5):2464-74 (2011).
Behlke, Chemical modification of siRNAs for in vivo use, Oligonucleotides. 18:305-319 (2008).
Belfort et al., Homing endonucleases: from genetic anomalies to programmable genomic clippers Methods Mal. Biol. 1123:1-26 (2014).

Boch et al., Breaking the code of DNA binding specificity of TAL-type III effectors, Science. 326:1509-12 (2009).
Boissel et al., "megaTALs a rare-cleaving nuclease architecture for therapeutic genome engineering," Nucleic Acids Research, 2014, vol. 42, No. 4 (pp. 2591-2601).
Boissel et al., Assembly and characterization of megaTALs for hyperspecific genome engineering applications, Methods Mal. Biol. 1239:171-96 (2015).
Bolduc et al., "Recessive Mutations in the Putative Calcium-Activated Chloride Channel Anoctamin 5 Cause Proximal LGMD2L and Distal MMD3 Muscular Dystrophies", The American Journal of Human Genetics, 86, Feb. 12, 2010, (pp. 213-221).
Bonnemann et al., Betasarcoglycan (A3b) mutations cause autosomal recessive muscular dystrophy with loss of the sarcoglycan complex, Nat. Genet., 11(3):266-273 (1995).
Bonnemann et al., Genomic screening for beta-sarcoglycan gene mutations: missense mutations may cause severe limb-girdle muscular dystrophy type 2E (LGMD 2E), Hum. Mol. Genet. 5:1953-1961 (1996).
Bouquet et al., Miyoshi-like distal myopathy with mutations in anoctamin 5 gene, Rev. Neural. (Paris), 168(2):135-41 (Feb. 2012).
Bramsen et al., Development of therapeutic-grade small interfering RNAs by chemical engineering, Front. Genet. 20:154 (2012).
Carter et al., "Adeno-associated virus vectors," Current Opinions in Biotechnology, 1992, vol. 3, Issue 5, pp. 533-539.
Ceccadi et al., Homologous recombination-deficient tumors are hyper-dependent on POLQ mediated repair, Nature. 518:258-262 (2015).
Cekaite et al., Gene expression analysis in blood cells in response to unmodified and 2'-modified siRNAs reveals TLR-dependent and independent effects, J. Mal. Biol. 365:90-108 (2007).
Centner et al., Identification of muscle specific ring finger proteins as potential regulators of the titin kinase domain, J. Mal. Biol. 306:717-26 (2001).
Cermak et al ., "Efficient design and assembly of custom TALEN and other TAL effector-based constructs for DNA targeting," Nucleic Acids Research, 2011, (pp. 1-11).
Cermak et al., Efficient design and assembly of custom TALENs using the Golden Gate platform, Methods Mal. Biol. 1239:133-59 (2015).
Ceyhan-Birsoy et al., Recessive truncating titin gene, TTN, mutations presenting as centronuclea1 myopathy, Neuroloov. 81:1205-14 (2013).
Chandrasekharan et al., Genetic defects in muscular dystrophy, Methods Enzymol. 479:291-322 (2010).
Chao et al., "Several log increase in therapeutic transgene delivery by distinct adeno-associated viral serotype vectors," Molecular therapy: the journal of the American Society of Gene Therapy, 2000, vol. 2, Issue 6, pp. 619-623.
Chao et al., "Sustained and complete phenotype correction of hemophilia B mice following intramuscular injection of AAV1 serotype vectors," Molecular therapy: the journal of the American Society of Gene Therapy, 2001, vol. 4, Issue 3, pp. 217-222.
Chauveau et al., A rising titan: TTN review and mutation update, Human Mutation. 35:1046-59 (2014).
Chernolovskaya et al., Chemical modification of siRNA, Curr. Opin. Mal. Ther. 12:158-67 (2010).
Chicoine et al., "Plasmapheresis eliminates the negative impact of AAV antibodies on microdystrophin gene expression following vascular delivery," Molecular therapy: the journal of the American Society of Gene Therapy, 2014, vol. 22, Issue 2, pp. 338-347.
Chicoine et al., "Vascular delivery of rAAVrh74.MCK.GALGT2 to the gastrocnemius muscle of the rhesus macaque stimulates the expression of dystrophin and laminin a2 surrogates", Mol. Ther., 22:713-24 (2014).
Chiorini et al., Cloning and characterization of adeno-associated virus type 5, J. Viral., 73(2): 1309-19 (Feb. 1999).
Chiorini et al., Cloning of adeno-associated virus type 4 (AAV4) and generation of recombinant AAV4 particles, J. Viral., 71 (9):6823-33 (Sep. 1997).
Cho et al., DNA repair: Familiar ends with alternative endings, Nature. 518:174-6 (2015).

(56) References Cited

OTHER PUBLICATIONS

Chu et al., "SV40 DNA transfection of cells in suspension: analysis of the efficiency of transcription and translation of T-antigen", Gene, 13, (1981) 197-202.
Clark et al., "Highly Purified Recombinant Adeno-Associated Virus Vectors Are Biologically Active and Free of Detectable Helper and Wild-Type Viruses," Hum. Gene. Ther., 1996, vol. 10, Issue 6, pp. 1031-1039.
Clark et al., "Recombinant adeno-associated viral vectors mediate long-term transgene expression in muscle," Human gene therapy, 1997, vol. 8, Issue 6, pp. 659-669.
Clark et al., A stable cell line carrying adenovirus-inducible rep and cap genes allows for infectivity titration of adeno-associated virus vectors, Gene. Therapy, 3(12):1124-1132 (1996).
Cox et al., "Therapeutic genome editing: prospects and challenges," Nature Medicine, Feb. 21, 2015, vol. 2 (pp. 121-131).
Cserjesi et al., "Myogenin induces the myocyte-specific enhancer binding factor MEF-2 independently of other muscle-specific gene products," Mol. Cell Biol., 1991, vol. 11, Issue 10, pp. 4854-4862.
D'Amario et al., Functionally competent cardiac stem cells can be isolated from endomyocardial biopsies of patients with advanced cardiomyopathies, Gire. Res. 108:857-61 (2011).
Database Genbank [online], Accession No. AJ277892.2, Nov. 14, 2006 issue.
Daya et al., "Gene Therapy Using Adeno-Associated Virus Vectors," Clinical Microbiology Reviews, Oct. 2008, vol. 21, No. 4 (pp. 583-593).
De et al., "High levels of persistent expression of alpha1-antitrypsin mediated by the nonhuman primate serotype rh.10 adeno-associated virus despite preexisting immunity to common human adeno-associated viruses," Molecular therapy: the journal of the American Society of Gene Therapy, 2006, vol. 13, Issue 1, pp. 67-76.
Deleavey et al., Chemical modification of siRNA, Curr. Protoc. Nucleic Acid Chem. Chapter 16:Unit 16.3 (2009).
Doench et al., "Optimized sgRNA design to maximize activity and minimize off-target effects of CRISPR-Cas9", Nature Biotechnology, Feb. 2016, vol. 34, No. 2 (pp. 184-191).
Draviam et al., The beta-li-core of sarcoglycan is essential for deposition at the plasma membrane, Muscle and Nerve. 34:691-701 (2006).
Dreier et al., "Development of Zinc Finger Domains for Recognition of the 5'-ANN-3' Family of DNA Sequences and Their Use in the Construction of Artificial Transcription Factors," The Journal of Biological Chemistry, Aug. 3, 2001, vol. 276, No. 31 (pp. 29466-29478).
Dreier et al., Insights into the molecular recognition of the 5'-GNN-3' family of DNA sequences by zinc finger domains, J. Mal. Biol. 303:489-502 (2000).
Dreier, B. et al, "Development of zinc finger domains for recognition of the 5'-CNN-3' family DNA sequence and their use in the construction of artificial transcription factors", The Journal of Biological Chemistry, vol. 280, No. 42, Oct. 21, 2005, pp. 35588-3597.
Dressman et al., Delivery of alpha- and beta-sarcoglycan by recombinant adeno-associated virus: efficient rescue of muscle, but differential toxicity, Hum. Gene. Ther., 13(13):1631-1646 (2002).
Dressman, AAV-Mediated gene transfer to models of muscular dystrophy: Insights into assembly of multi-subunit membrane proteins, University of Pittsburgh (1997).
Durbeej et al., Disruption of the beta-sarcoglycan gene reveals pathogenetic complexity of limb-girdle muscular dystrophy type 2E, Mol. Cell. 5:141-151 (2000).
Fanin et al., Gender difference in limb-girdle muscular dystrophy: a muscle fiber morphometric study in 101 patients, Clin. Neuropathology, 33:179-801 (2014).
Fanin et al., LGMD2E patients risk developing dilated cardiomyopathy, Neuromuscl. Disord., 13(4):303-309 (2003).
Flotte et al., "Gene expression from adeno-associated virus vectors in airway epithelial cells," American journal of respiratory cell and molecular biology, 1992, vol. 7, Issue 3, pp. 349-356.
Fonfara et al., "Phylogeny of Cas9 determines functional exchangeability of dual-RNA and Cas9 among orthologous type II CRISPR-Cas systems", Nucleic Acids Research, vol. 42, No. 4, Nov. 22, 2013, pp. 2377-2590 (14 pages).
Forbes et al., "Skeletal muscles of ambulant children with Duchenne muscular dystrophy: validation of multicenter study of evaluation with MR imaging and MR spectroscopy", Radiology, 269:198-207 (2013).
Fowler, et al., Improved knockdown from artificial microRNAs in an enhanced miR-155 Backbone: a designer's guide to potent multi-target RNAi, Nucleic Acids Research, 44(5): e48, (Nov. 2015).
Foye, Whole Genome Sequencing Solved Our Family's Genetic Mystery: Titin, Narrat. Inq. Bioeth 5:206-8 (2015).
Francois, et al., Accurate Titration of Infectious AAV Particles Requires Measurement of Biologically Active Vector Genomes and Suitable Controls. Molecular Therapy—Methods & Clinical Development, Sep. 21, 2018, vol. 10, pp. 223-236.
Fucini et al., Adenosine modification may be preferred for reducing siRNA immune stimulation, Nucleic Acid Ther. 22:205-210 (2012).
Gaglione et al., Recent progress in chemically modified siRNAs, Mini. Rev. Med. Chem. 10:578-9t (2010).
Gao et al., A novel and efficient model of coronary artery ligation and myocardial infarction in the mouse, Gire. Res. 107:1445-53 (2010).
Gao et al., A novel and efficient model of coronary artery ligation in the mouse, Methods Mal. Bic 1037:299-311 (2013).
Gao et al., Adeno-associated viruses undergo substantial evolution in primates during natural infections, Proc. Natl. Acad. Sci. U.S.A., 2003, vol. 100, pp. 6081-6086.
Gao, G. et al., "Clades of Adeno-Associated Viruses Are Widely Disseminated in Human Tissues," Journal of Virology, vol. 78, No. 12, 6381-6388, 2004.
Gautel et al., The central Z-disk region of titin is assembled from a novel repeat in variable copy numbers, Journal of Cell Science. 109:2747-2754 (1996).
Gebeyehu, et al., "Novel biotinylated nucleotide—analogs for labeling and colorimetric detection of DNA," Nucleic Acids Research, vol. 15, No. 11, (Jun. 11, 1987), p. 4513-4534.
GenBank Accession No. AF028704.1, Adena-associated virus 6, complete genome, Jan. 12, 1998.
GenBank Accession No. AF028705.1, Adeno-associated virus 3B, complete genome, Jan. 12, 1998.
GenBank Accession No. AF085716.1, Adeno-associated virus 5 DNA binding trs helicase (Rep22) and capsid protein (VP1) aenes, complete eds, Feb. 9, 1999.
Genbank Accession No. AX753246, Sequence 1 from Patent EP1310571, Jun. 23, 2003.
GenBank Accession No. AX753249, Sequence 4 from Patent EP1310571, Jun. 23, 2003.
GenBank Accession No. AX753250.1, Sequence 5 from Patent EP1310571, Jun. 23, 2003.
GenBank Accession No. AY631965.1, Adena-associated virus 10 nonstructural protein and caps protein genes, complete eds, Nov. 30, 2004.
GenBank Accession No. AY631966.1, Adena-associated virus 11 nonstructural protein and caps protein genes, complete eds, Nov. 30, 2004.
GenBank Accession No. DO813647.1, Adena-associated virus 12 Rep78 and VP1 genes, complete eds, Feb. 20, 2008.
GenBank Accession No. EU285562.1, Adena-associated virus 13 nonstructural protein and capsid protein genes, complete eds, Sep. 23, 2008.
Genbank Accession No. NC_001401.0, Adeno-associated virus-2, complete genome, Aug. 13, 2018.
GenBank Accession No. NC_001401.2, Adeno-associated virus-2, complete genome, Aug. 13, 2018.
Genbank Accession No. NC_001729.1, Adeno-associated virus-3, complete genome, Aug. 13, 2018.
GenBank Accession No. NC_001829.1, Adeno-associated virus-4, complete genome, Aug. 13, 2018.

(56) References Cited

OTHER PUBLICATIONS

GenBank Accession No. NC_001862, Adeno-associated virus 6, complete genome, Jan. 12, 2004, located at <https:www.ncbi.nlm.nih.gov/nuccore/NC_001862.1?report=genbank>.
GenBank Accession No. NC_002077.1, Adeno-associated virus-1, complete genome, Aug. 13, 2018, located at <https://www.ncbi.nlm.nih.gov/nuccore/NC_002077>.
GenBank Accession No. NC_006152.1, Adeno-associated virus 5, complete genome, Aug. 13, 2018.
GenBank Accession No. NC_006260.1, Adeno-associated virus-7, complete genome, Aug. 13, 2018.
GenBank Accession No. NC_006261.1, Adeno-associated virus-8, complete genome, Aug. 13, 2018.
Genbank Accession No. NM_00232.4, Homo sapiens sarcoglycan beta {SGCB}, Mma, Feb. 20, 2019.
Genbank Accession No. NP 000233.1, Beta Sarcoglyan {43kD dystrophin-associated glycoprotein} Homo Sapiens, Mar. 19, 1999.
GenBank Accession No. J01901, Adeno-associated virus 2, complete genome, Apr. 27, 1993.
GenBank Accession No. U89790.1, Adeno-associated virus 4, complete genome, Aug. 21, 2017.
GenBank Registered No. NG_011618, Homo sapiens titin (TTN), RefSeqGene (LRG_391) on chromosome 2, Apr. 5, 2020.
Genbank Synthetic construct Homo sapiens clone Image: 100069183, MGC:199194 anoctamin 5 (ANO5) mRNA, encodes complete protein GenBank: BC172489.1, Mar. 16, 2009.
GenBank: Accession No. NP 000223.1: beta-sarcoglycan sequence, dated Mar. 3, 1999.
Georganopoulou et al., "A Journey with LGMD: From Protein Abnormalities to Patient Impact", The Protein Journal, Kluwer Academic/Plenum Publishers, Dordrecht, NL, vol. 40, No. 4, Jun. 10, 2021, pp. 466-488.
Gerull et al., Identification of a novel frameshift mutation in the giant muscle filament titin in a large Australian family with dilated cardiomyopathy, J. Mal. Med. (Berl). 84:478-83 (2006).
Gerull et al., Mutations of TTN, encoding the giant muscle filament titin, cause familial dilated cardiomyopathy, Nat. Genet. 30:201-4 (2002).
Gibertini et al., Fibrosis and inflammation are greater in muscles of beta-sarcoglycan-null mouse than mdx mouse, Cell Tissue Res. 356:427-443 (2014).
Goeddel, "Gene Expression Technology: Methods in Enzymology," Academic Press, vol. 185, Jun. 11, 1990, pp. 3-7.
Gombash et al., Adeno-Associated Viral Vector Delivery to the Enteric Nervous System: A Review, Postdoc J., 2015, vol. 3, Issue 8, pp. 1-12.
Govoni et al., "Ongoing therapeutics trials and outcome measures for Duchenne muscular dystrophy", Cell Mol. Life Sci., 70:4585-602 (2013).
Graham et al., A new technique for the assay of infectivity of human adenovirus 5 DNA, Virology, 1973, vol. 52, Issue 2, pp. 456-467.
Gramlich et al., "Antisense-mediated exon skipping: a therapeutic strategy for titin-based dilated cardiomyopathy," EMBO Molecular Medicine, 7(5): 562-76 (2015).
Gramlich et al., "Stress-induced dilated cardiomyopathy in a knock-in mouse model mimicking human titin-based disease", J. Mal. Cell Cadiol. 47:352-8 (2009).
Granzier et al., "Deleting titin's I-band/A-band junction reveals critical roles for titin in biomechanica sensing and cardiac function", Proc. Natl. Acad. Sci. USA. 111:14589-94 (2014).
Greig et al., "Impact of intravenous infusion time on AAV8 vector pharmacokinetics, safety, and liver transduction in cynomolgus macaques," Molecular Therapy—Methods & Clinical Develop, 3: 16079, 7 pages (2016).
Grieger et al., "Production and characterization of adeno-associated viral vectors", Nat. Protoc. 1 :1412-1428 (2006).
Griffin et al. Preclinical systemic delivery of adeno-associated [alpha]-sarcoglycan gene transfer for limb-qirdle muscular dystrophy, Human Gene Therapy, 32(7-8): 390-404, (Apr. 2021).
Griffin et al., Defective Membrane Fusion and Repair in Anoctamin5-Deficient Muscular Dystrophy, Human Molecular Genetics, vol. 25, No. 10, pp. 1900-1911 (Feb. 23, 2016).
Griffin et al., "Dose-Escalation of Systemically Delivered Adeno-Associated Virus-Mediated alpha-Sarcoglycan in a Mouse Model With Limb-Girdle Muscular Dystrophy Type 2D," Presented at the 2019 Muscular Dystrophy Association Clinical and Scientific Conference, Apr. 13-17, 2019. (Retrieved from: investorrelations.sarepta.com/staticfiles/8b00e773-3b86-4769-83dc-4d2bf22ffb0c).
Griffin et al., "Systemic Dose Escalation Study of Alpha-Sarcoglycan Provides Functional Improvement in SGCA (I-) Mouse Model of LGMD2D," Molecular Therapy, vol. 26, No. 5S1, May 2018, p. 166.
Grose et al., "Homologous Recombination Mediates Functional Recovery of Dysferlin Deficiency following AAV5 Gene Transfer", PLoS One, Jun. 2012, vol. 7, Issue 6, e39233.
Guilinger et al., "Fusion of catalytically inactive Cas9 to FokI nuclease improves the specificity of genome modification," Nature Biotechnology, vol. 32, No. 6, Jun. 2014 (pp. 577-582).
Gutschner et al., "Genome engineering—Matching supply with demand," Cell Cycle, 15(11): 1395-96 2016.
Hafez et al., "Homing endonucleases: DNA scissors on a mission", Genome. 55:553-69 (2012).
Hagan, "When are mice considered old?" The Jackson Laboratory, https://www.jax.org/news-and-insights/jax-blog/2017/november/when-are-mice-considered-old# Nov. 7, 2017 (8 pages).
Hakim et al., Monitoring murine skeletal muscle function for muscle gene therapy, Methods Mal. Biol., 2011, vol. 709, pp. 75-89.
Hakim et al., The passive mechanical properties of the extensor digitorum longus muscle are compromised in 2- to 20-mo-old mdx mice, J. Appl. Physiol. 110: 1656-1663 (2011).
Handschin et al., Peroxisome proliferator-activated receptor gamma coactivator 1 coactivators, energy homeostasis, and metabolism, Endocrine reviews, 27:728-735 (2002).
Herman et al., "Truncations of titin causing dilated cardiomyopathy", N. Engl. J. Med. 366:619-28, 2012.
Hermonat et al., Use of adeno-associaled virus as a mammalian DNA cloning vector: transduction of neomycin resistance into mammalian tissue culture cells, Proc. Nall. Acad. Sci. U.S.A., 81:6466-6470 (1984).
Herzog et al., Stable gene transfer and expression of human blood coagulation factor IX after intramuscular injection of recombinant adeno-associated virus, Proc. Natl. Acad. Sci. USA, 1997, vol. 94 (pp. 5804-5809).
Hicks et al., A founder mutation in Anoctamin 5 is a major cause of limb-girdle muscular dystrophy, Brain, 134 (Pt. 1):171-82 (Jan. 2011).
Horii et al., Validation of microinjection methods for generating knockout mice by CRISPR/Cas-mediated genome engineering, Sci Rep. 4:4513 (2014).
International Application No. PCT/US2017/027636, International Preliminary Report on Patentability, mailed Oct. 16, 2018 (5 pages).
International Application No. PCT/US2017/027636, International Search Report and Written Opinion, mailed Jul. 5, 2017 (8 Pages).
International Application No. PCT/US19/39893, International Search Report and Written Opinion, mailed Sep. 25, 2019.
International Application No. PCT/US20/47339, International Preliminary Report on Patentability, mailed Mar. 3, 2022.
International Application No. PCT/US2016/061703, International Preliminary Report on Patentability, mailed May 15, 2018.
International Application No. PCT/US2020/019892, International Preliminary Report on Patentability, mailed Sep. 10, 2021 (8 pages).
International Preliminary Report on Patentability for Appl. Ser. No. PCT/US2016/062052 dated May 22, 2018.
International Preliminary Report on Patentability for Appl. Ser. No. PCT/US2017/027583 dated Oct. 25, 2018.
International Preliminary Report on Patentability for Appl. Ser. No. PCT/US2019/039893 dated Dec. 29, 2020 (7 pages).
International Preliminary Report on Patentability on PCT Appl. No. PCT/US2012/066265 dated May 27, 2014 (9 pages).
International Search report and Written Opinion for Appl. Ser. No. PCT/US2017/027583 dated Jul. 14, 2017 (8 pages).

(56) References Cited

OTHER PUBLICATIONS

International Search Report and Written Opinion for Appl. Ser. No. PCTUS2016/061703 dated Feb. 2, 2017 (13 pages).
International Search Report and Written Opinion on PCT Appl. No. PCT/US2020/047339 dated Dec. 10, 2020 (12 pages).
International Search Report and Written Opinion on PCT Appl. No. PCT/US2012/066265 dated Mar. 28, 2013 (7 pages).
International Search Report for Appl. Ser. No. PCT/US2016/062052 dated Feb. 7, 2017 (5 pages).
International Search Report issued in connection with PCT/US2020/019892 dated May 14, 2020 (4 pages).
Itoh-Satoh et al., Titan mutations as the molecular basis for dilated cardiomyopathy, Biochem. Biophys. Res. Commun. 291:385-93 (2002).
Jaber et al., Titin isoforms, extracellular matrix, and global chamber remodeling in experimental dilated cardiomyopathy: functional implications and mechanistic insight, Circ. Heart Fail. 1:192-9 (2008).
Jinek et al., "A Programmable Dual-RNA-Guided DNA Endonuclease in Adaptive Bacterial Immunity," Science, Aug. 17, 2012, 337(6096):816-821.
Johnson et al., "Muscle creatine kinase sequence elements regulating skeletal and cardiac muscle expression in transgenic mice," Mol. Cell Biol., 1989, vol. 9, Issue 8, pp. 3393-3399.
Judge et al., "Design of noninflammatory synthetic siRNA mediating potent gene silencing in vivo", Mol. Ther. 13:494-505 (2006).
Justison et al., Percutaneous assisted venous return isolated limb perfusion, J. Extra Corpor. Technol., 2009, vol. 41, Issue 4, pp. 231-234.
Kajigaya et al., Self-assembled B19 parvovirus caps ids, produced in a baculovirus system, are antigenically and immunogenically similar to native virions, Proc. Natl. Acad. Sci. USA, 88(11):4646-50 (Jun. 1991).
Kariko et al., "Suppression of RNA recognition by Toll-like receptors: the impact of nucleoside modification and the evolutionary origin of RNA," Immunity, Aug. 2005, vol. 23 (pp. 165-175).
Kennell, "Principles and Practices of Nucleic Acid Hybridization," Progress in Nucleic Acid Research and Molecular Biology, Academic Press, vol. 11, 1971, (pp. 259-301).
Kent et al., "Mechanism of microhomology-mediated end-joining promoted by human DNA polymerase theta", Nat. Struct. Mol. Biol. 22:230-237 (2015).
Kessler et al., "Gene delivery to skeletal muscle results in sustained expression and systemic delivery of a therapeutic protein," PNAS, 1996, vol. 93, pp. 14082-14087.
Kirnbauer et al., Virus-like particles of bovine papillomavirus type 4 in prophylactic and therapeutic immunization, Virology, 219(1):37-44 (May 1996).
Kleinstiver et al., The I-TevI nuclease and linker domains contribute to the specificity of monomerh TALENs, G3 (Bethesda). 4:1155-65 (2014).
Kobayashi et al., Sarcolemma-localized nNOS is required to maintain activity after mild exercise, Nature. 456:511-5 (2008).
Kole et al., "RNA therapeutics: beyond RNA interference and antisense oligonucleotides", Nat Rev Drug Discov. Jan. 20, 2012;11(2):125-40. doi: 10.1038/nrd3625.
Kolmerer et al., "Genomic organization of M line titin and its tissue-specific expression in two distinct isoforms", J. Mol. Biol. 256:556-63 (1996).
Kormann et al., "Expression of therapeutic proteins after delivery of chemically modified mRNA in mice," Nature Biotechnology, Feb. 2011, vol. 29, No. 2 (pp. 154-157).
Kornberg et al., "The early history of DNA polymerase: a commentary by Arthur Kornberg", Biochimica et Biophysica Acta. 1000:53-56 (1989).
Kotin et al., "Manufacturing Clinical Grade Recombinant Adeno-Associated Virus Using Invertebrate Cell Lines," Human Gene Therapy, 28(4):Abstract Only, (Apr. 1, 2017).
Kotin et al., Manufacturing Clinical Grade Recombinant Adeno-Associated Virus Using Invertebrate Cell Lines, Hum. Gene Ther., 28(4):350-360 (2017).
Kramerova et al., "Null mutation of calpain 3 {p94} in mice causes abnormal sarcomere formation in vivo and in vitro", Hum. Mol. Genet., 13(13):1373-1388 (2004).
Kramerova et al., Failure to up-regulate transcription of genes necessary for muscle adaptation underlies limb girdle muscular dystrophy 2A calpainopathy, Hum. Mol. Genet., 25(11):2194-2207 (2016).
Labeit et al., "Titins: giant proteins in charge of muscle ultrastructure and elasticity", Science. 270:293-6 (1995).
Laughlin et al., "Cloning of infectious adeno-associaled virus genomes in bacterial plasmids," Gene, 1983, vol. 23, Issue 1, pp. 65-73.
Laws et al., Progression of kyphosis in mdx mice, J. Appl. Physiol. 97:1970-7 (2004).
Lebkowski et al., Adeno-associated virus: a vector system for efficient introduction and integration of DNA into a variety of mammalian cell types, Mal. Cell. Biol., 1988, vol. 8, Issue 10, pp. 3988-3996.
Lewinter et al., Cardiac titin and heart disease, J. Cardiovasc. Pharmacol. 63:207-12 (2014).
Lewinter, "Titin isoforms in heart failure: are there benefits to supersizing", Circulation. 110:109-11 2004.
Lewis et al., "Generation of neutralizing activity against human immunodeficiency virus type 1 in serum by antibody gene transfer," Journal of virology, 2002, vol. 76, Issue 17, pp. 8769-8775.
Li et al., "Modularly assembled designer TAL effector nucleases for targeted gene knockout and gene replacement in eukaryotes," Nucleic Acids Research, 2011, vol. 39, No. 14 (pp. 6315-6325).
Li et al., Electrical impedance myography for the in vivo and ex vivo assessment of muscular dystrophy (mdx) mouse muscle, Muscle Nerve, 49(6):829-35 (Jun. 2014).
Li et al., Electrophysiologic biomarkers for assessing disease progression and the effect of riluzole in SOD1 G93A ALS mice, PLoS One, 8(6):e65976 (Jun. 2013).
Li et al., Intracoronary administration of cardiac stem cells in mice: a new, improved technique for cell therapy in murine models, Basic Res. Cardiol. 106:849-64 (2011).
Lin et al., Transcriptional co-activator PGC-1 alpha drives the formation of slow-twitch muscle fibres, Nature, 418:797-801 (2002).
Liu et al., "Adeno-associated virus-mediated microdystrophin expression protects young mdx muscle from contraction-induced injury," Molecular therapy: the journal of the American Society of Gene Therapy, 2005, vol. 11, Issue 2, pp. 245-256.
Liu et al., "Validated Zinc Finger Protein Designs for All 16 GNN DNA Triplet Targets," The Journal of Biological Chemistry, Feb. 8, 2002, vol. 277, No. 6 (pp. 3850-3856).
Louis et al., "EM_EST:BE676391", Jan. 27, 2011 (Jan. 27, 2011), XP055708767, Retrieved from the Internet: URL:http://ibis.internal.epo.org/exam/dbfetch.jsp?id=EM_EST:BE676391 [retrieved on Jun. 25, 2020].
Ma et al., Pol III Promoters to express small RNAs: Delineation of transcription initiation, Mol. Ther. Nucleic Acids. 3:e161 (2014).
Mader et al., "A steroid-inducible promoter for the controlled overexpression of cloned genes in eukaryotic cells," Proc Natl. Acad. Sci. U.S.A., 1993, vol. 90, Issue 12, pp. 5603-5607.
Mahmood et al., "Limb-girdle muscular dystrophies: Where next after six decades from the first proposal (review)," Molecular Medicine reports, 2014, vol. 9 (pp. 1515-1532).
Mak et al., "The crystal structure of TAL effector PthXo1 bound to its DNA target," Science, Feb. 10, 2012, vol. 335, No. 6069 (pp. 716-719).
Makarenko et al., Passive stiffness changes caused by upregulation of compliant titin isoforms in human dilated cardiomyopathy hearts, Gire. Res. 95:708-16 (2004).
Marsic et al., Vector Design Tour de Force: Integrating Combinatorial and Rational Approaches to Derive Novel Adeno-associated Virus Variants, Molecular Therapy, 22(11):1900-1909 (2014).

(56) References Cited

OTHER PUBLICATIONS

Martin et al., Overexpression of Galgt2 in skeletal muscle prevents injury resulting from eccentric contractions in both mdx and wild-type mice, Am. J. Physiol. Cell Physiol., vol. 296, pp. 476-488, Dec. 24, 2008.

Mashiko et al., Generation of mutant mice by pronuclear injection of circular plasmid expressing Cas9 and single guided RNA, Sci. Rep. 3:3355 (2013).

Mateos-Gomez et al., Mammalian Polymerase theta promotes alternative-NHEJ amd suppresses recombination, Nature. 518:254-257 (2015).

Matsuda et al., Visualization of dystrophic muscle fibers in mdx mouse by vital staining with Evans blue: evidence of apoptosis in dystrophin-deficient muscle, J. Biochem., 118(5):959-964 (1995).

McCarty et al., "Adeno-associated virus terminal repeat (TR) mutant generates self-complementary vectors to overcome the rate-limiting step to transduction in vivo", Gene Therapy, vol. 10, May 30, 2003, pp. 2112-2118.

McCarty et al., "Self-complementary recombinant adeno-associated virus (scAAV) vectors promote efficient transduction independently of DNA synthesis", Gene Therapy, May 22, 2001, vol. 8, pp. 1248-1254.

McCarty et al., Self-complementary AAV Vectors; Advances and Applications, Molecular Therapy, 2008, vol. 16, Issue 10, pp. 1648-1656.

McLaughlin et al., "Adeno-Associated Virus General Transduction Vectors: Analysis of Proviral Structures", Journal of Virology, 1988, vol. 62, No. 6, pp. 1963-1973.

McNally et al., The genetic landscape of cardiomyopathy and its role in heart failure, Cell. Metab. 21:174-182 (2015).

Meadows et al., Micro-RNA-29 Overexpression by adeno-associated virus suppresses fibrosis in mdx:utm+/− Mice (S61.003), Neurology, 82:S61.003 (Abstract) (2014).

Meadows et al., Reducing Skeletal Muscle Fibrosis with AAV-Delivered miR-29, 2012, Neurology, vol. 78, Issue 1, Supplement P04.089.

Melacini et al., Heart involvement in muscular dystrophies due to sarcoglycan gene mutations, Muscle Nerve. 22:473-479 (1999).

Mendell et al., "A phase 1/2a follistatin gene therapy trial for becker muscular dystrophy," Molecular therapy : the journal of the American Society of Gene Therapy, 2015, vol. 23, Issue 1, pp. 192-201.

Mendell et al., "Gene Therapy for Muscular Dystrophy: Lessons Learned and Path Forward", Neuroscience Letters, vol. 527, No. 2, Oct. 2012, 21 pages.

Mendell et al., "Limb-girdle muscular dystrophy type 2D gene therapy restores alpha-sarcoglycan and associated proteins," Ann. Neural., 2009, vol. 66 Issue 3, pp. 290-297.

Mendell et al., "Sustained alpha-sarcoglycan gene expression after gene transfer in limb-girdle muscular dystrophy, type 2D," Annals of neurology, 2010, vol. 68, Issue 5, pp. 629-638.

Mendell et al., Gene Delivery for Limb-Girdle Muscular Dystrophy Type 2D by Isolated Limb Infusion, Human Gene Therapy, 2019, vol. 30, Issue 7, pp. 794-801.

Mendell et al., Gene Therapy for Spinal Muscular Atrophy Type 1 Shows Potential to Improve Survival and Motor Functional Outcomes, Mol. Ther. 24:S190 (2016).

Mendell et al., Single-Dose Gene-Replacement Therapy for Spinal Muscular Atrophy, N. Engl. J. Med., 377:1713-1722 (2017).

Merten, O.W., AAV vector production: state of the art developments and remaining challenges. Cell and Gene Therapy Insights, Dec. 1, 2016, vol. 2, No. 5, pp. 521-551.

Mingozzi et al. "Therapeutic in vivo gene transfer for genetic disease using AAV: progress and challenges", Nature Reviews Genetics, May 2011, vol. 12 (pp. 341-355).

Monjaret et al., "The Phenotype of Dysferlin-Deficient Mice is not Rescued by Adeno-Associated Virus-Medicated Transfer of Anoctamin 5," Human Gene Therapy Clinical Development, 24(2):65-76 (Jun. 1, 2013).

Moore et al., Limb-girdle muscular dystrophy in the United States, J. Neuropathol. Exp. Neural., 65(10):995-1003 (2006).

Moorwood et al., Isometric and eccentric force generation assessment of skeletal muscles isolated from murine models of muscular dystrophies, Journal of Visualized Experiments. 71:e50036 (2013).

Mori et al., "Two novel adeno-associated viruses from cynomolgus monkey: pseudotyping characterization of capsid protein," Virology, 2004, vol. 330, Issue 2, pp. 375-383.

Moscou et al., "A Simple Cipher Governs DNA Recognition by TAL Effectors", Science, Dec. 11, 2009, vol. 326 (p. 1501).

Murphy et al., "Long-term correction of obesity and diabetes in genetically obese mice by a single intramuscular injection of recombinant adeno-associated virus encoding mouse leptin," Proceedings of the National Academy of Sciences of the United States of America, 1997, vol. 94, Issue 25, pp. 13921-13926.

Muscat et al., "Multiple 5'-flanking regions of the human alpha-skeletal actin gene synergislically modulate muscle-specific expression," Mol. Cell. Biol., 1987, vol. 7, Issue 11, pp. 4089-4099.

Muzyczka, "Use of Adeno-Associated Virus as a General Transduction Vector for Mammalian Cells," Current Topics in Microbiology and Immunology, 1992, vol. 158, pp. 97-129.

Narayanaswami et al., Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine, Neurology, 83:1453-1463 (2014).

NCBI Accession No. NG_051363.1, *Homo sapiens* TTN antisense RNA 1 (TTN-AS1), RefSeqGene on chromosome 2, dated Feb. 17, 2020.

NCBI Accession No. XM_012650762.1, Predicted:Propithecus coquereli titin (TTN), mRNA, dated Jun. 1, 2015.

NCBI Accession No. XM_024453100.1, Predicted: *Homo sapiens* titin (TTN), transcript variant X12, mRNA, dated Mar. 1, 2020.

NCBI Blast Tool: Pairwise Similarity 1, Instant App ('488) SEQ ID No. 1 [1-3977]:: U.S. Pat. No. 9,981,049 B2 SEQ ID No. 8 (CAPN3) (2024).

NCBI Blast Tool: Pairwise Similarity 2, Instant App ('488) SEQ ID No. 1 [1107-3572]:: U.S. Pat. No. 9,981,049 B2 SEQ ID No. 8 (CAPN3) (2024).

NCBI Reference Sequence: "anoctamin-5 isoform a [*Homo sapiens*]", GenPept, Mar. 15, 2015, NP_998764.1.

Obermann et al., Molecular structure of the sarcomeric M band: mapping of titin and myosin binding domains in myomesin and the identification of a potential regulatory phosphorylation site in myomesin, EMBO J. 16:211-20 (1997).

Pacak et al., Long-term Skeletal Muscle Protection After Gene Transfer in a Mouse Model of LGMD-2D, Molecular Therapy, 2007, vol. 15, Issue 10, pp. 1775-1781.

Paul et al., "Increased Viral Titer Through Concentration of Viral Harvests from Retroviral Packaging Lines," Human Gene Therapy, 1993, vol. 4, Issue 5, pp. 609-615.

Pavlovicova et al., Structure and composition of tubular aggregates of skeletal muscle fibres, Gen. Physiol. Biophys., 22(4):425-40 (Dec. 2003).

Payne et al., Nutritional therapy improves function and complements corticosteroid intervention in mdx mice. Muscle Nerve. Jan. 2006; 33(1):66-77.

Peer et al., Special delivery: targeted therapy with small RNAs, Gene. Ther. 18:1127-33 (2011).

Peled et al., Titin mutation in familial restrictive cardiomyopathy, Int. J. Cardiol. 171:24-30 (2014).

Penttila et al., Eight new mutations and the expanding phenotype variability in muscular dystrophy caused by ANOS, Neurology, 78(12):897-903 (Mar. 2012).

Perrin et al., "An experimental rabies vaccine produced with a new BHK-21 suspension cell culture process: use of serum-free medium and perfusion-reactor system," Vaccine, 1995, vol. 13, Issue 13, pp. 1244-1250.

Powers et al., Exercise-induced oxidative stress in humans: cause and consequences, Free Radic. Biol. Med., 51 (5):942-50 (Sep. 2011 ).

Pozsgai et al., "Beta-Sarcoglycan Gene Transfer Leads to Functional Improvement in a Model of LGMD2E," Molecular Therapy vol. 22, Supplement 1, May 2014 (p. S199).

(56) References Cited

OTHER PUBLICATIONS

Pozsgai et al., "Pre-Clinical Efficacy Study of Beta-Sarcoglycan Gene Transfer," Molecular Therapy, May 1, 2013, vol. 21, No. 1 (p. S68).

Rabinowitz et al., Cross-packaging of a single adeno-associated virus (AAV) type 2 vector genome into multiple AAV serotypes enables transduction with broad specificity, J Virol., 2002, vol. 76, Issue 2, pp. 791-801.

Rafael-Fortney et al., Early treatment with lisinopril and spironolactone preserves cardiac and skeletal muscle in duchenne muscular dystrophy mice, Circulation. 124:582-8 (2011).

Raj et al, "Self-complementary adeno-associated viral vectors for gene therapy of hemophilia B: progress and challenges" Expert Review of Hematology, Oct. 2011, vol. 4, No. 5 (pp. 539-549).

Ran et al., "In vivo genome editing using *Staphylococcus aureus* Cas9," Nature, Apr. 9, 2015, vol. 520, (18 pages).

Richard et al., "Mutations In The Proteolytic Enzyme Calpain 3 Cause Limb-Girdle Muscular Dystrophy Type 2A", Cell, 81(1):27-40 (1995).

Roberts et al., Integrated allelic, transcriptional, and phenomic dissection of the cardiac effects of titin truncations in health and disease, Sci. Transl. Med. 7:270ra6 (2015).

Rodino-Klapac et al., "A translational approach for limb vascular delivery of the micro-dystrophin gene without high volume or high pressure for treatment of Duchenne muscular dystrophy," Journal of Translational Medicine, 2007, vol. 5, Issue 45 (pp. 1-11).

Rodino-Klapac et al., "Micro-dystrophin and follistatin co-delivery restores muscle function in aged DMD model," Human Molecular Genetics, Dec. 2013, vol. 22, No. 24 (pp. 4929-4937).

Rodino-Klapac et al., "Persistent expression of FLAG-tagged micro dystrophin in nonhuman primates following intramuscular and vascular delivery," Molecular therapy: the journal of the American Society of Gene Therapy, 2010, vol. 18, Issue 1 (pp. 109-117).

Rodino-Klapac et al., Demonstration of SGCA Expression and Related Outcomes in Phase I/IIa Safety Isolated Limb Perfusion Trial in LGMD2D Subjects, Molecular Therapy, 2018, vol. 26, Issue 5, Supplemental 1, p. 1, Abstract No. 250.

Rodino-Klapac et al., Lack of toxicity of alpha-sarcoglycan overexpression supports clinical gene transfer trial in LGMD2D, Neurology, 2008, vol. 71, Issue 4, pp. 240-247.

Rose, comprehensive Virology 3:1-61 (1974).

Roudaut et al., "Restriction of Calpain3 Expression to the Skeletal Muscle Prevents Cardiac Toxicity and Corrects Pathology in a Murine Model of Limb-Girdle Muscular Dystrophy", Circulation, 128(10): 1094-1104, (Sep. 2013).

Ruffing et al., "Mutations in the carboxy terminus of adeno-associated virus 2 capsid proteins affect viral infectivity: lack of an RGD integrin-binding motif," Journal of General Virology, 1994, vol. 75, pp. 3385-3392.

Rutledge et al., Infectious clones and vectors derived from adeno-associated virus (AAV) serotypes other than AAV type 2, J. Viral., 7291):309-19 (Jan. 1998).

Sahenk et al., Systemic delivery of AAVrh74.tMCK.hCAPN3 rescues the phenotype in a mouse model for LGMD2A/R1, Mol. Ther. Methods Clin. Dev., 22:401-414 (2021).

Salva et al., "Design of Tissue-specific Regulatory Cassettes for High-level rAAV-mediated Expression in Skeletal and Cardiac Muscle," Mol. Ther., 2007, vol. 15, Issue 2, pp. 320-329.

Sambrook et al., "Molecular Cloning, a Laboratory Manual", Cold Spring Harbor Laboratory Press, Cold Spring Harbor, N.Y., 1989, 30 pages.

Sambrook et al., Cold spring harbor laboratory press, cold Spring Harbor, N.Y., (2001).

Sambrook et al., Molecular Cloning: A Laboratory Manual, 2" edition (1989).

Samulski et al., "Cloning of adeno-associaled virus into pBR322: rescue of intact virus from the recombinant plasmid in human cells," Proc. Nall. Acad. Sci. U.S.A., 1982, vol. 79, Issue 6, pp. 2077-2081.

Samulski et al., "Helper-Free Stocks of Recombinant Adeno-Associated Viruses: Normal Integration Does Not Require Viral Gene Expression," Journal of Virology, 1989, vol. 63, Issue 9, pp. 3822-3828.

Sander et al., CRISPR-Cas systems for editing, regulating and targeting genomes, Nat. Biotechnol. 32:347-55 (2014).

Sandona et al., Sarcoglycanopalhies: molecular pathogenesis and therapeutic prospects, Exp Rev. Mol. Med. 11:e28 (2009).

Sanganalmath et al., Cell therapy for heart failure: a comprehensive overview of experimental and clincal studes, current challenges, and future directions, Gire. Res. 113:810-34 (2013).

Sarepta Therapeutics: "Sarepta Therapeutics' Investigational Gene Therapy SRP-9003 for the Treatment of Limb-Girdle Muscular Dystrophy Type 2E Shows Sustained Expression and Functional Improvements 2 Years After Administration", Mar. 18, 2021, pp. 1-3, Retrieved from the Internet: URL: https://investorrelations.sarepta.com/news--releases/news-release-details/sarepta-therapeutics-investigational-gene-therapy-srp-9003-0 [retrieved on Jun. 23, 2023].

Schnepp et al., "Highly purified recombinant adeno-associated virus vectors. Preparation and quantitation," Methods Mol. Med., 2002, vol. 69, pp. 427-443.

Schreiber et al., The transcriptional coactivator PGC-1 regulates the expression and activity of the orphan nuclear receptor estrogen-related receptor alpha (ERRalpha), J. Biol. Chem., 278: 9013-9018 (2003).

Segal et al., "Toward controlling gene expression at will: Selection and design of zinc finger domains recognizing each of the 5'-GNN-3' DNA target sequences," Proceedings of the National Academy of Sciences, USA, Mar. 1999, vol. 96 (pp. 2758-2763).

Semenza et al., "Hypoxia-inducible nuclear factors bind to an enhancer element located 3' to the human erythropoietin gene," Proc. Natl. Acad. Sci. U.S.A., 1991, vol. 88, Issue 13, pp. 5680-5684.

Semplicini et al., Clinical and genetic spectrum in limb-girdle muscular dystrophy type 2E, Neurology, 84:1772-81 (2015).

Senapathy et al., "Molecular cloning of adeno-associated virus variant genomes and generation of infectious virus by recombination in mammalian cells," J Biol. Chem., 1984, vol. 259, pp. 4661-4666.

Shield et al., E-box sites and a proximal regulatory region of the muscle creatine kinase gene differentially regulate expression in diverse skeletal muscles and cardiac muscle of transgenic mice, Mal. Cell. Biol., 16(9):5058-5068 (1996).

Shih et al., Finding the Achilles' heel of Muscle Giant-TALEN-mediated Gene-editing in Zebrafish Titin, Circulation Research, Oct. 21, 2015, vol. 117, No.(suppl_1), pp. A344. DOI: https://doi.org/10.1161/res.117.suppl_1.344.

Siu et al., Familial dilated cardiomyopathy locus maps to chromosome 2q31, Circulation. 99:1022-6 (1999).

Smith et al., Modification and secretion of human interleukin 2 produced in insect cells by a baculovirus expression vector, Proc. Natl. Acad. Sci. USA, 82(24):8404-8 (1985).

Sondergaard et al., "AAV.Dysferlin Overlap Vectors Restore Function in Dysferlinopathy Animal Models," Annals of Clinical and Translational Neurology, 2015, vol. 2, Issue 3, pp. 256-270.

Sonntag et al., A viral assembly factor promotes AAV2 capsid formation in the nucleolus, PNAS, 2010, vol. 107, Issue 22, pp. 10220-10225.

Sorimachi et al., Tissue-specific expression and alpha-actinin binding properties of the Z-disc titin: implications for the nature of vertebrate Z-discs, J. Mal. Biol. 270:688-95 (1997).

Soutschek et al., "Therapeutic silencing of an endogenous gene by systemic administration of modified siRNAs," Nature, Nov. 2004, pp. 173-178, vol. 432.

Srivastava et al., "Nucleotide sequence and organization of the adeno-associated virus 2 genome," J Virol., 1983, vol. 45, Issue 2, pp. 555-564.

Steentoft et al., Precision genome editing: a small revolution for glycobiology, Glycobiology. 24:663-80 (2014).

Straub et al., Animal models for muscular dystrophy show different patterns of sarcolemmal disruption, J. Cell Biol. 139:375-385 (1997).

(56) References Cited

OTHER PUBLICATIONS

Strobel, et al. "Antioxidant Supplementation Reduces Skeletal Muscle Mitochondrial Biogenesis", Official Journal of the American College of Sports Medicine, 2011, pp. 1017-1024.
Sun et al., Correction of Multiple Striated Muscles in Murine Pompe Disease Through Adena-Associated Virus-mediated Gene Therapy, Mal. Ther., 16(8):1366-71 (2008).
Sveen et al., Cardiac involvement in patients with limb-girdle muscular dystrophy type 2 and Becker muscular dystrophy, Arch. Neurol., 65(9):1196-1201 (2008).
Thiruvengadam et al., "Anoctamin 5 Knockout Mouse Model Recapitulates LGMD2L Muscle Pathology and Offers Insight Into in vivo Functional Deficits," Journal of Neuromuscular Diseases, 2021, vol. 8 (S243-S255).
Torella, et al., "Cardiovascular development: towards biomedical applicability; Resident cardiac stem cells", CMLS Cellular and Molecular Life Sciences 64(6): 661-673 (2007).
Tratschin et al., "A Human Parvovirus, Adeno-Associated Virus, as a Eurcaryotic Vector: Transient Expression and Encapsidation of the Procaryotic Gene for Chloramphenicol Acetyltransferase", Molecular and Cellular Biology, vol. 4, No. 10, Oct. 1984 (pp. 2072-2081).
Tratschin et al., "Adeno-Associated Virus Vector for High-Frequency Integration, Expression, and Rescue of Genes in Mammalian Cells", Molecular and Cellular Biology, vol. 5, Issue 11, Nov. 1985, pp. 3251-3260.
Tsai et al., "Guide-seq enables genome-wide profiling of off-target cleavage by CRISPR-Cas nucleases," Nature Biotechnology, Feb. 2015, vol. 33, No. 2 (pp. 187-197).
Tsai et al., Dimeric CRISPR RNA-guided FokI nucleases for highly specific genome editing, Nat. Biotechnol. 32:569-76 (2014).
Van Akkooi et al., Isolated limb perfusion for an irresectable melanoma recurrence in a Jehovah's witness, Eur. J. Cardiothorac. Surg., 2006, vol. 30, Issue 2, pp. 408-410.
Voikar et al., Long-term individual housing in C57BU6J and DBA/2 mice: assessment of behavioral consequences, Genes Brain Behav., 4(4):240-52 (2005).
Volkov et al., Selective protection of nuclease-sensitive sites in siRNA prolongs silencing effect, Oligonucleotides. 19:191-202 (2009).
Wang et al., "Construction and analysis of compact muscle-specific promoters for AAV vectors," Gene Therapy, 2008, vol. 15, Issue 22, pp. 1489-1499.
Wang et al., "The potential of adeno-associated viral vectors for gene delivery to muscle tissue", Exp. Opin. on Drug. Del., 11(3):345-364 (2014).
Wang et al., Loss of miR-29 in myoblasts contributes to dystrophic muscle pathogenesis, Mol. Ther., 20(6):1222-33 (2012).
Wang et al., Rapid and efficient assembly of transcription activator-like effector genes by USER cloning, J. Genet. Genomics. 41:339-47 (2014).
Wang et al., Recombinant AAV serotype 1 transduction efficiency and tropism in the murine brain, Gene Ther., 2003, vol. 10, Issue 17, pp. 1528-1534.
Watson et al., "Recombinant DNA," Scientific American, Second Edition, 2001 (pp. 153-154).
Weber et al., "A Modular Cloning System for Standardized Assembly of Multigene Constructs," Feb. 2011, vol. 6, No. 2, e16765 (11 pages).
Wein et al., Translation from a DMD exon 5 IRES results in a functional dystrophin isoform that attenuates dystrophinopathy in humans and mice, Nature Medicine, 20(9):992-1000 (2014).
Weintraub et al., "The myoD gene family: nodal point during specification of the muscle cell lineage," Science, vol. 251, 1991, pp. 761-766.
Whitehead et al., Silencing or stimulation? siRNA delivery and the immune system, Annual Review of Chemical and Biomolecular Engineering. 2:77-96 (2011).
Wikipedia, "Adeno-associated virus," downloaded Dec. 29, 2017 (pp. 1-18).
Wikipedia, "Limb-girdle muscular dystrophy," 11 pages, Retrieved Oct. 26, 2023, from https://en.wikipedia.org/wiki/Limb-girdle_muscular_dystrophy (11 pages).
Winkler, Oligonucleotide conjugates for therapeutic applications, Ther. De/iv. 4:791-809 (2013).
Witting et al: "Anoctamin 5 muscular dystrophy in Denmark: prevalence, genotypes, phenotypes, cardiac findings, and muscleprotein expression", Case Reports, May 14, 2013, PMID: 23670307 DOI: 10.1007/s00415-013-6934-y.
Wolfs et al., MegaTevs: single-chain dual nucleases for efficient gene disruption, Nucliec Acids Res. 42:8816-29 (2014).
Wong-Kisiel et al., Two siblings with limb-girdle muscular dystrophy type 2E responsive to deflazacort, Neuromusc. Disord. 20:122-124 (2010).
Wu et al., Mutational analysis of the adeno-associated virus type 2 (AAV2) capsid gene and construction of AAV2 vectors with altered tropism, J. Viral., 74(18):8635-47 (Sep. 2000).
Xiao et al. "Production of High-Titer Recombinant Adeno-Associated Virus Vectors in the Absence of Helper Adenovirus," Journal of Virology, Mar. 1998, vol. 72 No. 3 (pp. 2224-2232).
Xiao et al., "Efficient long-term gene transfer into muscle tissue of immunocompetent mice by adeno-associated virus vector," Journal of virology, 1996, vol. 70, Issue 11, pp. 8098-8108.
Xu et al., "An Isolated Limb Infusion Method Allows for Broad Distribution of rAAVrh74.MCK.GALGT2 to Leg Skeletal Muscles in the Rhesus Macaque," Molecular Therapy—Methods & Clinical Develop, 10:89-104 (Sep. 2018).
Xu et al., "Genetic disruption of Ano5 in mice does not recapitulate human ANO5-deficient muscular dystrophy," Skeletal Muscle, 2015, vol. 5, No. 43 (pp. 1-14).
Xu et al., Postnatal overexpression of the CT GalNAc transferase inhibits muscular dystrophy in mdx mice without altering muscle growth or neuromuscular development: evidence for a utrophin-independent mechanism, Neuromuscul. Disord., 2007, vol. 17, Issue 3, pp. 209-220.
Yalvac et al., Impaired regeneration in calpain-3 null muscle is associated with perturbations in mTORC1 signaling and defective mitochondrial biogenesis, Skelet. Muscle, 7:27, 18 pages (2017).
Yan et al., Inverted terminal repeat sequences are important for intermolecular recombination and circularization of adeno-associated virus genomes, J. Viral., 79(1):364-79 (Jan. 2005).
Yuasa et al., "Gene therapy of muscular dystrophy: Systemic gene delivery to skeletal muscles" Jan. 2007, Drug Delivery System 22(2):140-147, doi.org/10.2745/dds.22.140 (English Abstract).
Zanotti et al., Opposing roles of miR-21 and miR-29 in the progression of fibrosis in Duchenne muscular dystrophy., Biochem. Biophys. Acta., 1852:1451-4 (2015).
Zetsche at el., "Cpfl Is a Single RNA-Guided Endonuclease of a Class 2 CRISPR-Cas System," Cell, Oct. 22, 2015, vol. 163, No. 3 (pp. 759-771).
Zhang et al., Dual AAV therapy ameliorates exercise-induced muscle injury and functional ischemia in murine models of Duchenne muscular dystrophy, Hum. Mal. Genet. 22:3720-9 (2013).
Zhao et al., BPV1 E2 protein enhances packaging of full-length plasmid DNA in BPV1 pseudovirions, Virology, 272(2):382-93 (Jul. 2000).
Zhou et al., Pressure Overload by Transverse Aortic Constriction Induces Maladaptive Hypertrophy in a Titin-Truncated Mouse Model, Biomed. Res. Int. 2015:163564 (2015).
Zou et al., "An internal promoter underlies the difference in disease severity between N- and C-terminal truncation mutations of Titin in zebrafish", eLife, Oct. 16, 2015, vol. 4, pp. e09406. DOI: https://doi.org/10.7554/eLife.09406.

\* cited by examiner

FIG. 14A
FIG. 14B
ALT
AST
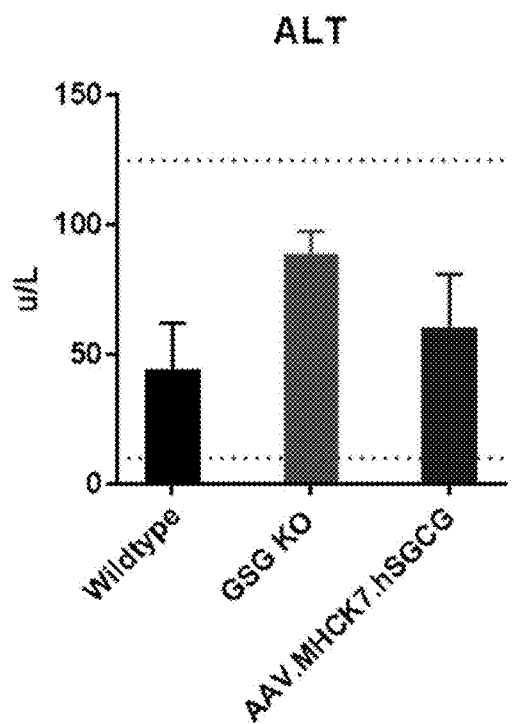
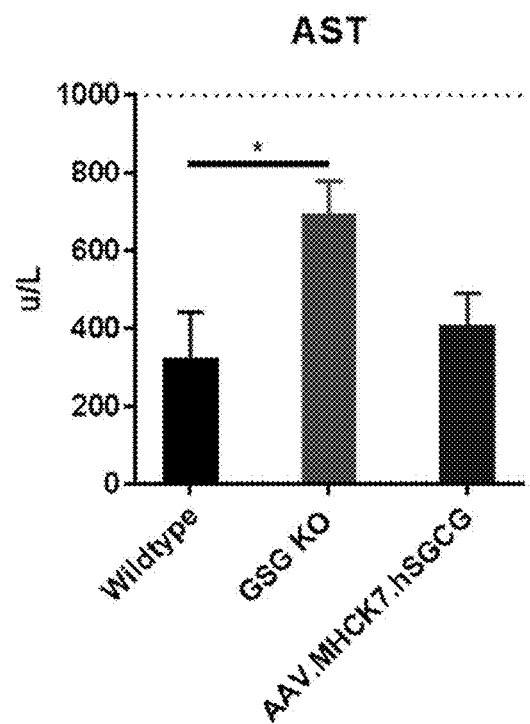

SEQUENCE LISTING

<160> NUMBER OF SEQ ID NOS: 11

<210> SEQ ID NO 1
<211> LENGTH: 876
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atggtgaggg agcagtacac cacagcaacc gagggaatct gcatcgagag gccagagaac      60
cagtacgtgt ataagatcgg catctacggc tggcggaaga gatgtctgta tctgttcgtg     120
ctgctgctgc tgatcatcct ggtggtgaat ctggccctga ccatctggat cctgaaagtg     180
atgtggtttt ccccagcagg aatgggacac ctgtgcgtga caaaggacgg actgcggctg     240
gagggagagt ctgagttcct gtttcccctg tatgccaagg agatccacag cagagtggat     300
agctccctgc tgctgcagtc cacccagaac gtgacagtga acgcaaggaa tagcgaggga     360
gaggtgaccg gcagactgaa ggtcggcccc aagatggtgg aggtgcagaa tcagcagttc     420
cagatcaact ccaatgacgg caagcctctg tttacagtga tgagaagga ggtggtggtg     480 ggcaccgaca agctgagggt gacaggacct gagggcgccc tgttcgagca ctctgtggag     540
```

```
accccactgg tgcgcgcaga cccttttcag gatctgaggc tggagagccc aacacgcagc    600
ctgtccatgg acgcacccag aggcgtgcac atccaggcac acgcaggcaa gatcgaggcc    660
ctgagccaga tggatatcct gttccactct agcgacggca tgctggtgct ggatgccgag    720
accgtgtgcc tgcctaagct ggtgcagggc acatggggcc catctggctc ctctcagagc    780
ctgtacgaga tctgcgtgtg cccagatggc aagctgtatc tgtccgtggc cggcgtgtct    840
accacatgcc aggagcacaa ccacatctgt ctgtga                             876
```

<210> SEQ ID NO 2
<211> LENGTH: 291
<212> TYPE: PRT
<213> ORGANISM: Homo sapiens

<400> SEQUENCE: 2

```
Met Val Arg Glu Gln Tyr Thr Thr Ala Thr Glu Gly Ile Cys Ile Glu
1               5                   10                  15

Arg Pro Glu Asn Gln Tyr Val Tyr Lys Ile Gly Ile Tyr Gly Trp Arg
            20                  25                  30

Lys Arg Cys Leu Tyr Leu Phe Val Leu Leu Leu Ile Ile Leu Val
        35                  40                  45

Val Asn Leu Ala Leu Thr Ile Trp Ile Leu Lys Val Met Trp Phe Ser
    50                  55                  60

Pro Ala Gly Met Gly His Leu Cys Val Thr Lys Asp Gly Leu Arg Leu
65                  70                  75                  80

Glu Gly Glu Ser Glu Phe Leu Phe Pro Leu Tyr Ala Lys Glu Ile His
                85                  90                  95

Ser Arg Val Asp Ser Ser Leu Leu Gln Ser Thr Gln Asn Val Thr
            100                 105                 110

Val Asn Ala Arg Asn Ser Glu Gly Glu Val Thr Gly Arg Leu Lys Val
        115                 120                 125

Gly Pro Lys Met Val Glu Val Gln Asn Gln Gln Phe Gln Ile Asn Ser
    130                 135                 140

Asn Asp Gly Lys Pro Leu Phe Thr Val Asp Glu Lys Glu Val Val Val
145                 150                 155                 160

Gly Thr Asp Lys Leu Arg Val Thr Gly Pro Glu Gly Ala Leu Phe Glu
                165                 170                 175

His Ser Val Glu Thr Pro Leu Val Arg Ala Asp Pro Phe Gln Asp Leu
            180                 185                 190

Arg Leu Glu Ser Pro Thr Arg Ser Leu Ser Met Asp Ala Pro Arg Gly
        195                 200                 205

Val His Ile Gln Ala His Ala Gly Lys Ile Glu Ala Leu Ser Gln Met
    210                 215                 220

Asp Ile Leu Phe His Ser Ser Asp Gly Met Leu Val Leu Asp Ala Glu
225                 230                 235                 240

Thr Val Cys Leu Pro Lys Leu Val Gln Gly Thr Trp Gly Pro Ser Gly
                245                 250                 255

Ser Ser Gln Ser Leu Tyr Glu Ile Cys Val Cys Pro Asp Gly Lys Leu
            260                 265                 270

Tyr Leu Ser Val Ala Gly Val Ser Thr Thr Cys Gln Glu His Asn His
        275                 280                 285

Ile Cys Leu
    290
```

<210> SEQ ID NO 3
<211> LENGTH: 2225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
ctgcgcgctc gctcgctcac tgaggccgcc cgggcaaagc ccgggcgtcg ggcgaccttt      60
ggtcgcccgg cctcagtgag cgagcgagcg cgcagagagg gagtgggggtt aaccaattgg   120
cgcggccgca agcttgcatg tctaagctag acccttcaga ttaaaaataa ctgaggtaag   180
ggcctgggta ggggaggtgg tgtgagacgc tcctgtctct cctctatctg cccatcggcc   240
ctttggggag gaggaatgtg cccaaggact aaaaaaaggc catggagcca gaggggcgag   300
ggcaacagac ctttcatggg caaaccttgg ggccctgctg tctagcatgc cccactacgg   360
gtctaggctg cccatgtaag gaggcaaggc ctggggacac ccgagatgcc tggttataat   420
taacccagac atgtggctgc ccccccccc caacacctg ctgcctctaa aaataacccct     480
gtccctggtg gatcccctgc atgcgaagat cttcgaacaa ggctgtgggg gactgagggc   540
aggctgtaac aggcttgggg gccagggctt atacgtgcct gggactccca aagtattact   600
gttccatgtt cccggcgaag ggccagctgt ccccgccag ctagactcag cacttagttt     660
aggaaccagt gagcaagtca gcccttgggg cagcccatac aaggccatgg ggctgggcaa   720
gctgcacgcc tgggtccggg gtgggcacgg tgcccgggca acgagctgaa agctcatctg   780
ctctcagggg cccctccctg gggacagccc tcctggcta gtcacaccct gtaggctcct     840
ctatataacc caggggcaca ggggctgccc tcattctacc accacctcca cagcacagac   900
agacactcag gagcagccag cggcgcgccc aggtaagttt agtctttttg tcttttattt   960
caggtcccgg atccggtggt ggtgcaaatc aaagaactgc tcctcagtgg atgttgcctt  1020
tacttctagg cctgtacgga agtgttactt ctgctctaaa agctgcggaa ttgtacccgg  1080
taccaccatg gtgagggagc agtacaccac agcaaccgag ggaatctgca tcgagaggcc  1140
agagaaccag tacgtgtata agatcggcat ctacggctgg cggaagagat gtctgtatct  1200
gttcgtgctg ctgctgctga tcatcctggt ggtgaatctg gccctgacca tctggatcct  1260
gaaagtgatg tggttttccc cagcaggaat gggacacctg tgcgtgacaa aggacggact  1320
gcggctggag ggagagtctg agttcctgtt tcccctgtat gccaaggaga tccacagcag  1380
agtggatagc tccctgctgc tgcagtccac ccagaacgtg acagtgaacg caaggaatag  1440
cgagggagag gtgaccggca gactgaaggt cggccccaag atggtggagg tgcagaatca  1500
gcagttccag atcaactcca atgacggcaa gcctctgttt acagtggatg agaaggaggt  1560
ggtggtgggc accgacaagc tgagggtgac aggacctgag ggcgccctgt cgagcactc   1620
tgtggagacc ccactggtgc gcgcagaccc ttttcaggat ctgaggctgg agagcccaac  1680
acgcagcctg tccatggacg cacccagagg cgtgcacatc caggcacacg caggcaagat  1740
cgaggccctg agccagatgg atatcctgtt ccactctagc gacggcatgc tggtgctgga  1800
tgccgagacc gtgtgcctgc ctaagctggt gcagggcaca tggggcccat ctggctcctc  1860
tcagagcctg tacgagatct gcgtgtgccc agatggcaag ctgtatctgt ccgtggccgg  1920
cgtgtctacc acatgccagg agcacaacca catctgtctg tgactcgagg gccgcaataa  1980
aagatcttta ttttcattag atctgtgtgt tggttttttg tgtgtcctgc aggggcgcgc  2040
ctaatctaga gcatggctac gtagataagt agcatggcgg gttaatcatt aactacaagg  2100
```

```
aaccccctagt gatggagttg gccactccct ctctgcgcgc tcgctcgctc actgaggccg      2160
ggcgaccaaa ggtcgcccga cgcccgggct tgcccgggc ggcctcagtg agcgagcgag       2220
cgcgc                                                                  2225

<210> SEQ ID NO 4
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
aagcttgcat gtctaagcta gacccttcag attaaaaata actgaggtaa gggcctgggt        60
aggggaggtg gtgtgagacg ctcctgtctc tcctctatct gcccatcggc cctttgggga      120
ggaggaatgt gcccaaggac taaaaaaagg ccatggagcc agaggggcga ggcaacaga       180 cctttcatgg gcaaaccttg ggccctgct gtctagcatg ccccactacg ggtctaggct       240
gcccatgtaa ggaggcaagg cctggggaca cccgagatgc ctggttataa ttaacccaga     300
catgtggctg cccccccccc cccaacacct gctgcctcta aaataacccc tgtccctggt      360
ggatcccctg catgcgaaga tcttcgaaca aggctgtggg ggactgaggg caggctgtaa     420
caggcttggg ggcagggct tatacgtgcc tgggactccc aaagtattac tgttccatgt      480
tcccggcgaa gggccagctg tccccgcca gctagactca gcacttagtt taggaaccag      540
tgagcaagtc agcccttggg gcagcccata caaggccatg gggctgggca agctgcacgc    600
ctgggtccgg ggtgggcacg gtgcccgggc aacgagctga aagctcatct gctctcaggg    660
gcccctccct ggggacagcc cctcctggct agtcacaccc tgtaggctcc tctatataac    720
ccaggggcac aggggctgcc ctcattctac caccacctcc acagcacaga cagacactca   780
ggagcagcca gc                                                         792

<210> SEQ ID NO 5
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aggtaagttt agtcttttg tcttttattt caggtcccgg atccggtggt ggtgcaaatc        60
aaagaactgc tcctcagtgg atgttgcctt tacttctagg cctgtacgga agtgttactt     120
ctgctctaaa agctgcggaa ttgtaccc                                        148

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggccgcaata aaagatcttt attttcatta gatctgtgtg ttggttttt gtg              53

<210> SEQ ID NO 7
<211> LENGTH: 110
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ctgcgcgctc gctcgctcac tgaggccgcc cgggcaaagc ccgggcgtcg ggcgaccttt      60
ggtcgcccgg cctcagtgag cgagcgagcg cgcagagagg gagtgggggtt              110

<210> SEQ ID NO 8
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ccactccctc tctgcgcgct cgctcgctca ctgaggccgg cgaccaaag gtcgcccgac      60 gcccgggctt tgcccgggcg gcctcagtga gcgagcgagc gcgc                     104

<210> SEQ ID NO 9
<211> LENGTH: 876
<212> TYPE: DNA
<213> ORGANISM: Homo sapiens

<400> SEQUENCE: 9
atggtgcgtg agcagtacac tacagccaca gaaggcatct gcatagagag gccagagaat     60
cagtatgtct acaaaattgg catttatggc tggagaaagc gctgtctcta cttgtttgtt    120 cttctttttac tcatcatcct cgttgtgaat ttagctctta caatttggat tcttaaagtg   180
atgtggtttt ctccagcagg aatgggccac ttgtgtgtaa caaagatgg actgcgcttg     240 gaagggaat cagaattttt attcccattg tatgccaaag aaatacactc cagagtggac     300
tcatctctgc tgctacaatc aacccagaat gtgactgtaa atgcgcgcaa ctcagaaggg    360
gaggtcacag gcaggttaaa agtcggtccc aaaatggtag aagtccagaa tcaacagttt   420
cagatcaact ccaacgacgg caagccacta tttactgtag atgagaagga agttgtggtt    480
ggtacagata aacttcgagt aactgggcct gaaggggctc ttttgaaca ttcagtggag     540 acaccccttg tcagagccga cccgtttcaa gaccttagat tagaatcccc cactcggagt    600
ctaagcatgg atgccccaag gggtgtgcat attcaagctc acgctgggaa aattgaggcg    660
ctttctcaaa tggatattct ttttcatagt agtgatggaa tgcttgtgct tgatgctgaa    720
actgtgtgct acccaagct ggtgcagggg acgtggggtc cctctggcag ctcacagagc     780
ctctacgaaa tctgtgtgtg tccagatggg aagctgtacc tgtctgtggc cggtgtgagc    840
accacgtgcc aggagcacag ccacatctgc ctctga                             876

<210> SEQ ID NO 10
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Ala Gly Gly Gly Ala Pro Met Ala Asp Asn Asn Glu Gly Ala
1               5                   10                  15
```

-continued

```
Asp Gly Val Gly Ser Ser Gly Asn Trp His Cys Asp Ser Thr Trp
         20              25              30

Leu Gly Asp Arg Val Ile Thr Thr Ser Thr Arg Thr Trp Ala Leu Pro
         35              40              45

Thr Tyr Asn Asn His Leu Tyr Lys Gln Ile Ser Asn Gly Thr Ser Gly
         50              55              60

Gly Ser Thr Asn Asp Asn Thr Tyr Phe Gly Tyr Ser Thr Pro Trp Gly
65                   70              75              80

Tyr Phe Asp Phe Asn Arg Phe His Cys His Phe Ser Pro Arg Asp Trp
                 85              90              95

Gln Arg Leu Ile Asn Asn Asn Trp Gly Phe Arg Pro Lys Arg Leu Asn
             100             105             110

Phe Lys Leu Phe Asn Ile Gln Val Lys Glu Val Thr Gln Asn Glu Gly
         115             120             125

Thr Lys Thr Ile Ala Asn Asn Leu Thr Ser Thr Ile Gln Val Phe Thr
         130             135             140

Asp Ser Glu Tyr Gln Leu Pro Tyr Val Leu Gly Ser Ala His Gln Gly
145             150             155             160

Cys Leu Pro Pro Phe Pro Ala Asp Val Phe Met Ile Pro Gln Tyr Gly
                 165             170             175

Tyr Leu Thr Leu Asn Asn Gly Ser Gln Ala Val Gly Arg Ser Ser Phe
             180             185             190

Tyr Cys Leu Glu Tyr Phe Pro Ser Gln Met Leu Arg Thr Gly Asn Asn
         195             200             205

Phe Glu Phe Ser Tyr Asn Phe Glu Asp Val Pro Phe His Ser Ser Tyr
210             215             220

Ala His Ser Gln Ser Leu Asp Arg Leu Met Asn Pro Leu Ile Asp Gln
225             230             235             240

Tyr Leu Tyr Tyr Leu Ser Arg Thr Gln Ser Thr Gly Gly Thr Ala Gly
                 245             250             255

Thr Gln Gln Leu Leu Phe Ser Gln Ala Gly Pro Asn Asn Met Ser Ala
             260             265             270

Gln Ala Lys Asn Trp Leu Pro Gly Pro Cys Tyr Arg Gln Gln Arg Val
         275             280             285

Ser Thr Thr Leu Ser Gln Asn Asn Asn Ser Asn Phe Ala Trp Thr Gly
290             295             300

Ala Thr Lys Tyr His Leu Asn Gly Arg Asp Ser Leu Val Asn Pro Gly
305             310             315             320

Val Ala Met Ala Thr His Lys Asp Asp Glu Glu Arg Phe Phe Pro Ser
                 325             330             335

Ser Gly Val Leu Met Phe Gly Lys Gln Gly Ala Gly Lys Asp Asn Val
             340             345             350

Asp Tyr Ser Ser Val Met Leu Thr Ser Glu Glu Ile Lys Thr Thr
         355             360             365

Asn Pro Val Ala Thr Glu Gln Tyr Gly Val Val Ala Asp Asn Leu Gln
         370             375             380

Gln Gln Asn Ala Ala Pro Ile Val Gly Ala Val Asn Ser Gln Gly Ala
385             390             395             400

Leu Pro Gly Met Val Trp Gln Asn Arg Asp Val Tyr Leu Gln Gly Pro
                 405             410             415

Ile Trp Ala Lys Ile Pro His Thr Asp Gly Asn Phe His Pro Ser Pro
             420             425             430

Leu Met Gly Gly Phe Gly Leu Lys His Pro Pro Pro Gln Ile Leu Ile
```

| | | 435 | | | | 440 | | | | 445 | | |
|---|---|---|---|---|---|---|---|---|---|---|---|---|

Lys Asn Thr Pro Val Pro Ala Asp Pro Pro Thr Thr Phe Asn Gln Ala
450                     455                 460

Lys Leu Ala Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Asn Val Asp Phe
            500                 505                 510

Ala Val Asn Thr Glu Gly Thr Tyr Ser Glu Pro Arg Pro Ile Gly Thr
            515                 520                 525

Arg Tyr Leu Thr Arg Asn Leu
            530             535

<210> SEQ ID NO 11
<211> LENGTH: 2217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | | | | | |
|---|---|---|---|---|---|
| atggctgccg | atggttatct | tccagattgg | ctcgaggaca | acctctctga | gggcattcgc | 60 |
| gagtggtggg | aacctgaaacc | tggagccccg | aaacccaaag | ccaaccagca | aaagcaggac | 120 |
| aacggccggg | tctggtgct | tcctggctac | aagtacctcg | acccttcaa | cggactcgac | 180 |
| aaggggagc | ccgtcaacgc | ggcggacgca | gcggccctcg | agcacgacaa | ggcctacgac | 240 |
| cagcagctcc | aagcgggtga | caatccgtac | ctgcggtata | tcacgccga | cgccgagttt | 300 |
| caggagcgtc | tgcaagaaga | tacgtctttt | gggggcaacc | tcgggcgcgc | agtcttccag | 360 |
| gccaaaaagc | gggttctcga | acctctgggc | ctggttgaat | cgccggttaa | gacggctcct | 420 |
| ggaaagaaga | gaccggtaga | gccatcaccc | cagcgctctc | cagactcctc | tacgggcatc | 480 |
| ggcaagaaag | ccagcagcc | cgcaaaaaag | agactcaatt | ttgggcagac | tggcgactca | 540 |
| gagtcagtcc | ccgaccctca | accaatcgga | gaaccaccag | caggcccctc | tggtctggga | 600 |
| tctggtacaa | tggctgcagg | cggtggcgct | ccaatggcag | acaataacga | aggcgccgac | 660 |
| ggagtgggta | gttcctcagg | aaattggcat | tgcgattcca | catggctggg | cgacagagtc | 720 |
| atcaccacca | gcacccgcac | ctgggccctg | cccacctaca | acaaccacct | ctacaagcaa | 780 |
| atctccaacg | gaacctcggg | aggaagcacc | aacgacaaca | cctacttcgg | ctacagcacc | 840 |
| ccctgggggt | attttgactt | caacagattc | cactgccact | tttcaccacg | tgactggcag | 900 |
| cgactcatca | caacaactg | gggattccgg | cccaagaggc | tcaacttcaa | gctcttcaac | 960 |
| atccaagtca | aggaggtcac | gcagaatgaa | ggcaccaaga | ccatcgccaa | taacctacc | 1020 |
| agcacgattc | aggtctttac | ggactcggaa | taccagctcc | cgtacgtgct | cggctcggcg | 1080 |
| caccagggct | gcctgcctcc | gttcccggcg | gacgtcttca | tgattcctca | gtacgggtac | 1140 |
| ctgactctga | acaatggcag | tcaggctgtg | ggccggtcgt | ccttctactg | cctggagtac | 1200 |
| tttccttctc | aaatgctgag | aacgggcaac | aactttgaat | tcagctacaa | cttcgaggac | 1260 |
| gtgcccttcc | acagcagcta | cgcgcacagc | cagagcctgg | accggctgat | gaaccctctc | 1320 |
| atcgaccagt | acttgtacta | cctgtcccgg | actcaaagca | cggcggtac | tgcaggaact | 1380 |
| cagcagttgc | tattttctca | ggccgggcct | aacaacatgt | cggctcaggc | caagaactgg | 1440 |

```
ctaccecggtc  cctgctaccg  gcagcaacgc  gtctccacga  cactgtcgca  gaacaacaac   1500
agcaactttg  cctggacggg  tgccaccaag  tatcatctga  atggcagaga  ctctctggtg   1560
aatcctggcg  ttgccatggc  tacccacaag  gacgacgaag  agcgattttt  tccatccagc   1620
ggagtcttaa  tgtttgggaa  acagggagct  ggaaaagaca  acgtggacta  tagcagcgtg   1680
atgctaacca  gcgaggaaga  aataaagacc  accaacccag  tggccacaga  acagtacggc   1740
gtggtggccg  ataacctgca  acagcaaaac  gccgctccta  ttgtaggggc  cgtcaatagt   1800
caaggagcct  tacctggcat  ggtgtggcag  aaccgggacg  tgtacctgca  gggtcccatc   1860
tgggccaaga  ttcctcatac  ggacggcaac  tttcatccct  cgccgctgat  gggaggcttt   1920
ggactgaagc  atccgcctcc  tcagatcctg  attaaaaaca  cacctgttcc  cgcggatcct   1980
ccgaccacct  tcaatcaggc  caagctggct  tctttcatca  cgcagtacag  taccggccag   2040
gtcagcgtgg  agatcgagtg  ggagctgcag  aaggagaaca  gcaaacgctg  gaacccagag   2100
attcagtaca  cttccaacta  ctacaaatct  acaaatgtgg  actttgctgt  caatactgag   2160
ggtacttatt  ccgagcctcg  ccccattggc  acccgttacc  tcacccgtaa  tctgtaa     2217
```

GENE THERAPY FOR LIMB-GIRDLE MUSCULAR DYSTROPHY TYPE 2C

CROSS REFERENCE TO RELATED APPLICATIONS

This application is a U.S. national stage application under 35 U.S.C. § 371 of International Application No. PCT/US2019/015779, filed Jan. 30, 2019, which in turn claims priority under 35 U.S.C. § 119 (e) to U.S. Provisional Patent Application No. 62/624,616, filed Jan. 31, 2018, the contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 25, 2019, is named 106887-7141 SL.txt and is 18,760 bytes in size.

FIELD OF THE INVENTION

The invention relates to gene therapy. More specifically, the disclosure provides gene therapy vectors such as adeno-associated virus (AAV) vectors for treating muscular dystrophy, e.g. limb girdle dystrophy type 2C (LGMD2C).

BACKGROUND OF THE INVENTION

Muscular dystrophies (MDs) are a group of genetic diseases. The group is characterized by progressive weakness and degeneration of skeletal muscles that control movement. Some forms of MD develop in infancy or childhood, while others may not appear until middle age or later. The disorders differ in terms of the distribution and extent of muscle weakness—some forms of MD also affect cardiac muscle, the age of onset, the rate of progression, and the pattern of inheritance.

One group of MDs is the limb girdle group (LGMD) of MDs. LGMDs are rare conditions, which present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, affected individuals can develop problems with walking and may need to use a wheelchair over time. The involvement of shoulder and arm muscles can lead to difficulty in raising arms over head and in lifting objects. In some types of LGMD, the heart and breathing muscles may be involved.

LGMD2C (limb girdle dystrophy type 2C) is caused by gamma(γ)-sarcoglycan (SGCG) deficiency. Like the other sarcoglycanopathies, it presents as a progressive muscular dystrophy starting in the girdle muscles before extending to lower and finally upper extremity muscles. Presentation typically occurs in mid to late teens. In attempting to treat LGMD2C, no form of drug therapy, including even corticosteroids, has changed the course of the disease.

Functional improvement in patients suffering from LGMD2C and other muscular dystrophies require both gene restoration and reduction of fibrosis. There is a need in the art for compositions and methods for treating LGMD2C and other muscular dystrophies.

SUMMARY OF THE INVENTION

Described herein are gene therapy vectors, e.g. recombinant adeno-associated virus (AAV) vectors, encoding γ-sarcoglycan and methods of delivering such vectors encoding γ-sarcoglycan to the muscle to reduce or prevent fibrosis; to maintain or improve muscle function; to increase muscular force; to increase muscle endurance; or to treat a γ-sarcoglycanopathy in a mammalian subject suffering from muscular dystrophy.

In addition, the disclosure provides therapies and approaches using gene therapy vectors to deliver γ-sarcoglycan to address the gene defect observed in LGMD2C (limb girdle dystrophy type 2C). In one aspect provided herein is a method for one or more of treating γ-sarcoglycanopathy; increasing muscular force, muscle endurance, and/or muscle mass; reducing fibrosis; reducing contraction-induced injury; decreasing fatty infiltration; and/or decreasing central nucleation in a subject in need thereof, and/or treating muscular dystrophy reducing degenerating fibers or necrotic fibers; reducing inflammation; elevating creatine kinase levels; treating myofiber atrophy and hypertrophy, and/or decreasing dystrophic calcification in a subject suffering from muscular dystrophy, the methods comprising, or consisting essentially of, or yet further consisting of administering to the subject a therapeutically effective amount of a recombinant adeno-associated virus (AAV) vector, wherein the rAAV vector comprises, or consists essentially of, or yet further consists of a gene expression cassette that comprises, or consists essentially of, or yet further consists of a polynucleotide sequence encoding γ-sarcoglycan under the transcriptional control of a promoter, said cassette flanked by one or more AAV inverted terminal repeats.

In one aspect, described herein is a recombinant AAV (rAAV) vector comprising, or consisting essentially of, or yet further consisting of a polynucleotide sequence encoding γ-sarcoglycan under the transcriptional control of a promoter. In some embodiments, the polynucleotide sequence encoding γ-sarcoglycan comprises, or consists essentially of, or yet further consists of a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 1 and encodes a protein that retains γ-sarcoglycan activity. In some embodiments, the polynucleotide sequence encoding γ-sarcoglycan comprises, or consists essentially of, or yet further consists of the nucleotide sequence set forth in SEQ ID NO: 1. In some embodiments, the polynucleotide sequence encoding γ-sarcoglycan consists the nucleotide sequence set forth in SEQ ID NO: 1 or a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 1 and encodes a protein that retains γ-sarcoglycan activity, that in one aspect, retains the nucleotide changes of SEQ ID NO: 1 as compared to the corresponding nucleotides in wild-type human polynucleotide encoding γ-sarcoglycan In another aspect, an rAAV vector described herein comprises, or consists essentially of, or yet further consists of a polynucleotide sequence encoding γ-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the amino acid sequence of SEQ ID NO: 2, and the protein retains γ-sarcoglycan activity.

γ-sarcoglycan activity is critical for muscle function. γ-sarcoglycan is one of several sarcolemmal transmembrane glycoproteins that interact with dystrophin and forms the dystrophin-glycoprotein complex, which spans the sarcolemma and is comprised of dystrophin, syntrophin, α-dystroglycans and β-dystroglycans, and sarcoglycans including γ-sarcoglycan. The dystrophin-glycoprotein complex provides a structural link between the subsarcolemmal cytoskeleton and the extracellular matrix of muscle cells. Non-limiting examples of muscle cells include cardiac, diaphragm, leg, pelvic girdle, shoulder and arm muscle cells. Further non-limiting examples of γ-sarcoglycan activity and consequences of γ-sarcoglycanopathy are described in Blake et al. (2002) Physiol Rev.; 82(2):291-329 and Tarakci et al. (2016) Front Biosci (Landmark Ed); 21:744-56.

In another aspect, the rAAV vectors described herein may be operably linked to a promoter and/or a muscle-specific control element to restrict expression to muscle. For example the muscle-specific control element is human skeletal actin gene element (GenBank Accession No. NG_006672.1), cardiac actin gene element (GenBank Accession No. NG_007553.1), myocyte-specific enhancer binding factor MEF (GenBank Accession No. NG_016443.2), muscle creatine kinase (MCK) (GenBank Accession No. AF188002.1), tMCK (truncated MCK), myosin heavy chain (MHC), MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypozia-inducible nuclear factors, steroid-inducible element or glucocorticoid response element (GRE).

In some embodiments, the muscle-specific promoter is MHCK7 (SEQ ID NO: 4) or an equivalent thereof. An exemplary rAAV vector described herein is pAAV.MHCK7.hSCGC which comprises, or consists essentially of, or yet further consists of the nucleotide sequence of SEQ ID NO: 3 or an equivalent thereof wherein the MHCK7 promoter spans nucleotides 136-927, a CMV intron spans nucleotides 937-1084, the γ-sarcoglycan sequence spans nucleotides 1094-1968 and the polyA spans nucleotides 1976-2028. In certain cases, pAAV.MHCK7.hSCGC is packaged in an AAV rh74 capsid.

The AAV can be any serotype, for example AAV1, AAV2, AAV3, AAV4, AAV5, AAV6, AAV7, AAV8, AAV9, AAV-10, AAV-11, AAV-12, AAV-13 or AAV rh74. In some embodiments, a rAAV vector comprises the inverted terminal repeat (ITR) sequences of AAV2.

Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

Compositions comprising or consisting essentially of any of the rAAV vectors described herein are also contemplated.

Methods of producing a recombinant AAV vector particle comprising culturing a cell that has been transfected with any recombinant AAV vector described herein and recovering recombinant AAV particles from the supernatant of the transfected cells are also provided. Viral particles comprising or consisting essentially of any of the recombinant AAV vectors described herein are also contemplated.

Methods of reducing fibrosis in a mammalian subject in need thereof is also provided. In this regard, the method comprises, or consists essentially of, or yet further consists of administering a therapeutically effective amount of an AAV vector described herein (or composition comprising, or consisting essentially of an AAV vector described herein) to the mammalian subject. In some embodiments, the mammalian subject suffers from muscular dystrophy. In some embodiments, administration of an AAV vector described herein (or composition comprising, or consisting essentially of an AAV vector described herein) reduces fibrosis in skeletal muscle or in cardiac muscle of the subject.

In another aspect, described herein is a method of increasing muscular force or muscle mass or muscle endurance in a mammalian subject comprising, or consisting essentially of, or yet further consisting of administering a therapeutically effective amount of an AAV vector described herein (or composition comprising, or consisting essentially of an AAV vector described herein) to the mammalian subject.

In any of the methods of the disclosure, the subject may be suffering from muscular dystrophy such as limb-girdle muscular dystrophy or any other dystrophin-associated muscular dystrophy.

Also provided is a method of treating muscular dystrophy in a mammalian subject comprising, or consisting essentially of, or yet further consisting of administering a therapeutically effective amount of an AAV vector described herein (or composition comprising, or consisting essentially of an AAV vector described herein) to the mammalian subject. In some embodiments, the muscular dystrophy is limb-girdle muscular dystrophy.

In any of the methods of the disclosure, the rAAV is administered by any appropriate mode of administration, e.g., intramuscular injection or intravenous injection. In addition, in any of the method of the disclosure, the rAAV is administered systemically, such as parental administration by injection, infusion or implantation.

The compositions of the disclosure are formulated for intramuscular injection or intravenous injection. In addition, the compositions of the disclosure are formulated for systemic administration, such as parental administration by injection, infusion or implantation.

In addition, any of the compositions formulated for administration to a subject suffering from muscular dystrophy (such as limb-girdle muscular dystrophy or any other dystrophin-associated muscular dystrophy). Also described herein are combination therapies comprising, or consisting essentially of one or more of the compositions disclosed herein and a corticosteroid. Provided herein are host cells comprising the rAAV vector of this disclosure. Further provided herein are kits comprising any of one or more of the embodiments disclosed herein and instructions for use. The kits can comprise, or consist essentially of, one or more of the compositions disclosed herein and a corticosteroid or one or more of the combination therapies provided herein. In any of the uses of the disclosure, the medicament is formulated for administration, e.g., intramuscular injection or intravenous injection. In addition, in any of the uses of the disclosure, the medicament is formulated for systemic administration, such as parental administration by injection, infusion or implantation. In addition, any of the medicaments may be prepared for administration to a subject suffering from muscular dystrophy (such as limb-girdle muscular dystrophy or any other dystrophin associated muscular dystrophy).

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

BRIEF DESCRIPTION OF THE DRAWINGS

Figures 3A, 3B:
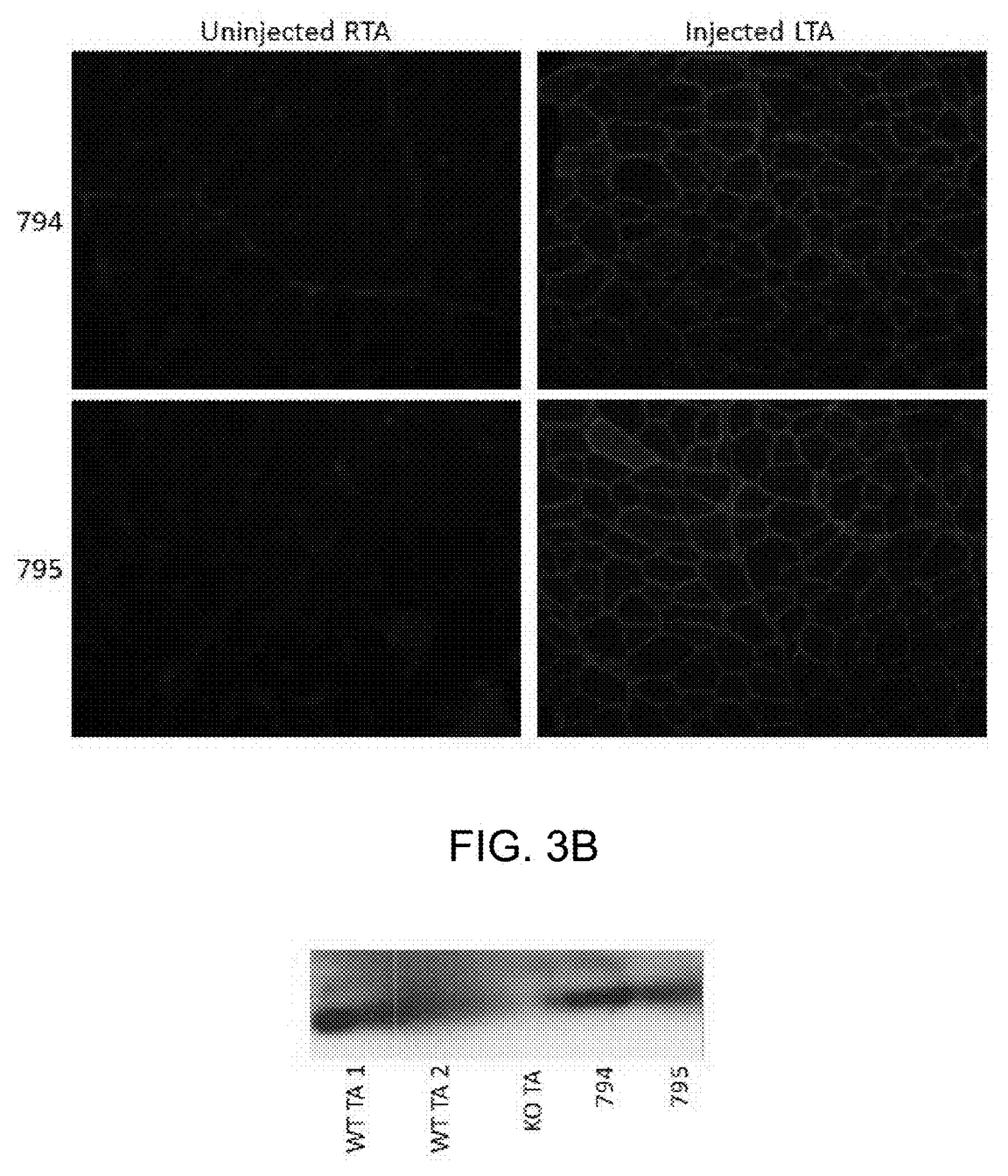

FIGS. 3A-3C depict in vivo vector potency. scAAVrh74.MHCK7. hSGCG was injected into the tibialis anterior (TA) muscle of γ-SG KO mice at 3e10 vg total dose. FIG. 3A shows immunofluorescence staining of TA muscle in γ-SG KO mice. Nearly 100% γ-sarcoglycan protein expression at the sarcolemma resulted from vector delivery. FIG. 3B shows a Western blot for γ-sarcoglycan expression in injected TA muscles from treated mice #794, 795. FIG. 3C shows immunofluorescence staining of TA muscle in control wild-type mice ("BL6 WT TA") or uninjected control γ-SG KO mice ("GSG KO TA"), as well as an unstained sample ("GSG KO No Primary").

FIG. 4A shows immunofluorescence staining indicating overexpression of γ-sarcoglycan by membrane and intracellular staining. FIG. 4B shows Western blotting indicating overexpression of γ-sarcoglycan in injected LTA muscle.

FIGS. 14A-14B show comparison of serum ALT and AST. Serum from BL6 WT mice (n=6), untreated SGCG−/− mice (n=6), and AAV.MHCK7.hSGCG IV treated SGCG−/− mice (n=5) (1e13vg total dose) was analyzed for biochemical component levels. Liver enzymes alkaline aminotransferase (ALT, FIG. 14A) and aspartate aminotransferase (AST, FIG. 14B) were elevated in diseased SGCG−/− mice and returned to near WT levels following treatment. *=$p<0.05$. Dashed lines represent lower and upper limits of normal range.

DETAILED DESCRIPTION

Figure 1:
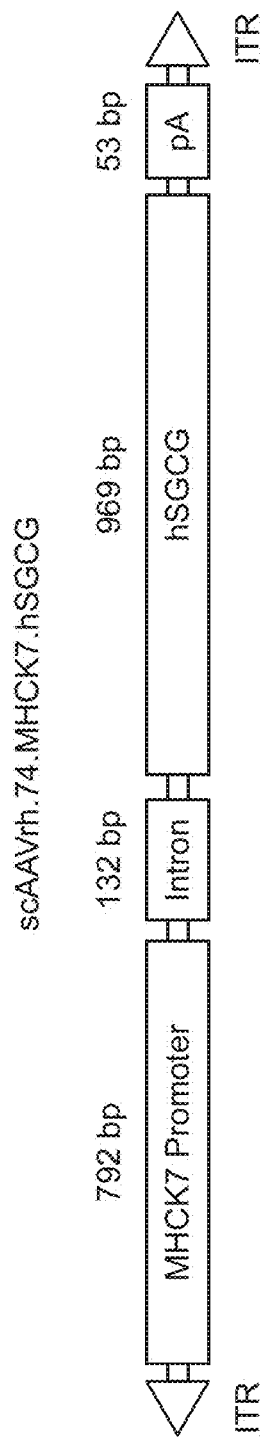
FIG. 1 depicts an AAV vector (scAAVrh74.MHCK7.hSGCG) comprising a codon-optimized full-length human γ-sarcoglycan (hSCGB) cDNA (SEQ ID NO: 1). The construct is flanked by two ~100 bp AAV inverted terminal repeats (ITR), includes a codon optimized human γ-sarcoglycan cDNA (hSGCG), chimeric intron (Intron), synthetic polyadenylation signal (pA), and is driven by the skeletal and cardiac muscle specific MHCK7 promoter.

The present disclosure relates to administration of a recombinant adeno-associated virus (rAAV) vector comprising a polynucleotide expressing γ-sarcoglycan for a reduction or complete reversal of muscle fibrosis in an individual suffering from limb-girdle muscular dystrophy As demonstrated in the Examples, administration of the rAAV vector described herein resulted in restoration of γ-sarcoglycan expression in knockout mice. Administration of an rAAV vector described herein will result in the reversal of dystrophic features including fewer degenerating fibers, reduced inflammation, and improved functional recovery by protection against eccentric contraction with increased force generation. The disclosure encompasses treatment of limb-girdle muscular dystrophy in a subject (e.g., a human subject) by administration of a rAAV vector described herein.

In the present description, any concentration range, percentage range, ratio range, or integer range is to be understood to include the value of any integer within the recited range and, when appropriate, fractions thereof (such as one tenth and one hundredth of an integer) unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. As used herein, "plurality" may refer to one or more components (e.g., one or more miRNA target sequences). In this application, the use of "or" means "and/or" unless stated otherwise.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Decrease" or "reduce" refers to a decrease or a reduction in a particular value of at least 5%, for example, 5, 6, 7, 8, 9, 10, 15, 20, 25, 30, 35, 40, 45, 50, 55, 60, 65, 70, 75, 80, 85, 90, 95, 99 or 100% as compared to a reference value. A decrease or reduction in a particular value may also be represented as a fold-change in the value compared to a reference value, for example, at least 1, 2, 3, 4, 5, 6, 7, 8, 9, 10, 15, 20, 30, 40, 50, 60, 70, 80, 90, 100, 200, 500, 1000-fold, or more, decrease as compared to a reference value.

"Increase" refers to an increase in a particular value of at least 5%, for example, 5, 6, 7, 8, 9, 10, 15, 20, 25, 30, 35, 40, 45, 50, 55, 60, 65, 70, 75, 80, 85, 90, 95, 99, 100, 200, 300, 400, 500% or more as compared to a reference value. An increase in a particular value may also be represented as a fold-change in the value compared to a reference value, for example, at least 1-fold, 2, 3, 4, 5, 6, 7, 8, 9, 10, 15, 20, 30, 40, 50, 60, 70, 80, 90, 100, 200, 500, 1000-fold or more, increase as compared to the level of a reference value.

"Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

"Administration" refers herein to introducing an agent or composition into a subject.

"Treating" as used herein refers to delivering an agent or composition to a subject to affect a physiologic outcome. In some embodiments, treating refers to the treatment of a disease in a subject, e.g., in a human, including (a) inhibiting the disease, e.g., arresting disease development or preventing disease progression; (b) relieving the disease, e.g., causing regression of the disease state; (c) curing the disease; and (d) preventing onset of disease, e.g., arresting disease development in an asymptomatic subject identified as a carrier of a genetic defect. In one aspect, treatment excludes prophylaxis or prevention.

When the disease is muscular dystrophy the following clinical end points are non-limiting examples of treatment: decrease in specific force, increase in resistance to injury, increase in muscular force, increase in muscle endurance, increase in muscle mass, reduction in contraction-induced injury, decrease in fatty infiltration, decrease in central nucleation, reduction in degenerating fibers or necrotic fibers, reduction in inflammation, elevation in creatine kinase levels, decrease in myofiber atrophy and hypertrophy and/or decrease in dystrophic calcification.

When the disease is fibrosis, the following clinical end points are non-limiting examples of treatment: reduction in fibrotic tissue, reduction in inflammation, reduction in fibroblastic lesions, reduction in activated fibroblast proliferation, reduction in myofibroblast genesis, reduction in rate of decline of Forced Vital Capacity (FVC), wherein FVC is the total amount of air exhaled during the lung function test, absolute and relative increases from baseline in FVC, absolute increase from baseline in FVC (% Predicted), increase in progression-free survival time, decrease from baseline in St George's Respiratory Questionnaire (SGRQ) total score, wherein SGRQ is a health-related quality of life questionnaire divided into 3 components: symptoms, activity and impact and the total score (summed weights) can range from 0 to 100 with a lower score denoting a better health status, and relative decrease from baseline in high resolution computerized tomography (HRCT) quantitative lung fibrosis (QLF) score, wherein the QLF score ranges from 0 to 100% and greater values represent a greater amount of lung fibrosis and are considered a worse health status. Non-limiting examples clinical end points for fibrosis treatment and tests that can be performed to measure said clinical end points are described in the following clinical trials: NCT03733444 (clinicaltrials.gov/ct2/show/NCT03733444) (last accessed on Jan. 9, 2019), NCT00287729 (clinicaltrials.gov/ct2/show/NCT00287729) (last accessed on Jan. 9, 2019), NCT00287716 (clinicaltrials.gov/ct2/show/NCT00287716) (last accessed on Jan. 9, 2019), NCT02503657(clinicaltrials.gov/ct2/show/NCT02503657) (last accessed on Jan. 9, 2019), NCT00047645 (clinicaltrials.gov/ct2/show/NCT00047645) (last accessed on Jan. 9, 2019), NCT02802345 (clinicaltrials.gov/ct2/show/NCT02802345) (last accessed on Jan. 9, 2019), NCT01979952 (clinicaltrials.gov/ct2/show/NCT01979952) (last accessed on Jan. 9, 2019), NCT00650091 (clinicaltrials.gov/ct2/show/NCT00650091) (last accessed on Jan. 9, 2019), NCT01335464 (clinicaltrials.gov/ct2/show/NCT01335464) (last accessed on Jan. 9, 2019), NCT01335477 (clinicaltrials.gov/ct2/show/NCT01335477) (last accessed on Jan. 9, 2019), NCT01366209 (clinicaltrials.gov/ct2/show/NCT01366209) (last accessed on Jan. 9, 2019). Further non-limiting examples clinical end points for fibrosis treatment and tests that can be performed to measure said clinical end points are described in King et al, (2014) N Engl J Med. May 29;370(22):2083-92 and Richeldi et al., (2014) N Engl J Med. May 29; 370(22): 2071-82.

The term "effective amount" or "therapeutically effective amount" refer to the minimum amount of an agent or composition required to result in a particular physiological effect (e.g., an amount required to increase, activate, or enhance a particular physiological effect). The effective amount or therapeutically effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount or therapeutically effective amount of a particular agent may also be expressed as the half-maximal effective concentration ($EC_{50}$), which refers to the concentration of an agent that results in a magnitude of a particular physiological response that is half-way between a reference level and a maximum response level.

"Population" of cells refers to any number of cells greater than 1, but is preferably at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, at least $1\times10^{10}$ cells, or more cells. A population of cells may refer to an in vitro population (e.g., a population of cells in culture) or an in vivo population (e.g., a population of cells residing in a particular tissue).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans and/or domestic animals.

As used herein "vector" refers to a nucleic acid molecule capable transferring or transporting a nucleic acid molecule to cell, along with, in a viral vector, one or more viral proteins, such as for encapsulated viruses the capsid of the virus. The transferred nucleic acid is generally linked to, e.g., inserted into, the vector nucleic acid molecule. A vector may include sequences that direct autonomous replication or reverse transcription in a cell, or may include sequences sufficient to allow integration into host cell DNA. "Vectors" include gene therapy vectors. As used herein, the term "gene therapy vector" refers to a vector capable of use in performing gene therapy, e.g., delivering a polynucleotide sequence encoding a therapeutic polypeptide to a subject. Gene therapy vectors may comprise a polynucleotide ("transgene") encoding a protein, e.g., γ-sarcoglycan.

As used herein, the term "expression cassette" refers to a DNA segment that is capable in an appropriate setting of driving the expression of a polynucleotide (e.g., a transgene) encoding a protein (e.g., γ-sarcoglycan) that is incorporated in said expression cassette. When introduced into a host cell, an expression cassette inter alia is capable of directing the cell's machinery to transcribe the transgene into RNA, which is then usually further processed and finally translated into the therapeutically active polypeptide. The gene therapy vector can comprise, or consist essentially of expression cassette. The term expression cassette excludes polynucleotide sequences 5' to the 5' ITR and 3' to the 3' ITR. Provided herein are host cells comprising, or consisting essentially of, or yet further consisting of the rAAV vector of this disclosure. The cells can be of any appropriate species, e.g., mammalian cells.

As used herein, the phrases "operably linked" or "under the transcriptional control" with respect to a polynucleotide refers, interchangeably, to a configuration of promoter or muscle-specific control element and polynucleotide that enables the polynucleotide to be transcribed by a polymerase capable of binding to the promoter. In one aspect, the muscle-specific control element is to restrict expression to muscle. Non-limiting examples of muscle-specific control elements are human skeletal actin gene element (GenBank Accession No. NG_006672.1), cardiac actin gene element (GenBank Accession No. NG_007553.1), myocyte-specific enhancer binding factor MEF (GenBank Accession No. NG_016443.2), muscle creatine kinase (MCK) (GenBank Accession No. AF188002.1), tMCK (truncated MCK), myosin heavy chain (MHC), MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypozia-inducible nuclear factors, steroid-inducible element or glucocorticoid response element (GRE).

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

As used herein, the term "AAV" is a standard abbreviation for adeno-associated virus. Adeno-associated virus is a single-stranded DNA parvovirus that grows only in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector." Thus, production of AAV vector particle necessarily includes production of AAV vector, as such a vector is contained within an AAV vector particle.

Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983}; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and pi 9), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes of the disclosure comprise, or consist essentially of, or yet further consist of a nucleic acid molecule encoding γ-sarcoglycan (e.g., SEQ ID NO: 1) and one or more AAV ITRs flanking the nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). The nucleotide sequences of the genomes of various AAV serotypes are known in the art. To promote skeletal muscle specific expression, AAV1, AAVS, AAV6, AAV8 or AAV9 may be used.Thus, in one aspect, described herein is a recombinant AAV vector comprising, or consisting essentially of a polynucleotide sequence encoding γ-sarcoglycan under the transcriptional control of a promoter and/or a muscle-specific control element. In some embodiments, the polynucleotide sequence encoding γ-sarcoglycan comprises, or consists essentially of, or yet further consists of a sequence e.g. at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence of codon-optimized human γ-sarcoglycan, which is set forth in SEQ ID NO: 1 (see Table 1) and encodes protein that retains γ-sarcoglycan activity. In some embodiments, the polynucleotide sequence encoding γ-sarcoglycan comprises the nucleotide sequence set forth in SEQ ID NO: 1 or a sequence e.g. at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% identical to SEQ ID NO. 1 that encodes a protein that retains γ-sarcoglycan activity.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared. A polynucleotide or polynucleotide region (or a polypeptide or polypeptide region) having a certain percentage (for example, 60%, 65%, 70%, 75%, 80%, 85%, 90%, 95%, 98% or 99%) of "sequence identity" to a reference sequence means that, when aligned, that percentage of bases (or amino acids) at each position in the test sequence are identical to the base (or amino acid) at the same position in the reference sequence. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Details of these programs can be found at the following Internet address: ncbi.nlm.nih.gov/blast/Blast.cgi. An "equivalent" of a polypeptide or protein is one that has a certain sequence identity to that reference polypeptide or protein, (for example, 60%, 65%, 70%, 75%, 80%, 85%, 90%, 95%, 98% or 99% identity to the reference) and retains similar activity or function compared to the reference polypeptide or protein.

"Comprising" or "comprises" is intended to mean that the compositions, for example media, and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

In one aspect, the gene expression cassette of rAAV vector of this disclosure is flanked by one or more AAV inverted terminal repeats. In another aspect, the polynucleotide sequence encoding γ-sarcoglycan of rAAV vector comprises, or consists essentially of, or yet further consists of a nucleotide sequence at least 95% identical to SEQ ID NO: 1 and/or the nucleotide sequence set forth in SEQ ID NO: 1 and encodes protein that retains γ-sarcoglycan activity. In a further aspect, the polynucleotide sequence encoding γ-sarcoglycan of rAAV vector encodes an amino acid sequence at least 95% identical, at least 99% identical, or 100% to SEQ ID NO: 2 and encodes protein that retains γ-sarcoglycan activity.

In some embodiments, the rAAV vector disclosed herein is of the serotype AAV1, AAV2, AAV4, AAV5, AAV6, AAV7, AAV8, AAV9, AAV10, AAV11, AAV12, AAV13 or AAV rh74. In other embodiments, the genome of the rAAV vector comprises, or consists essentially of a muscle-specific control element and wherein muscle-specific control element is operably linked to the polynucleotide sequence. Non-limiting examples of muscle-specific control elements are human skeletal actin gene element, cardiac actin gene element, myocyte-specific enhancer binding factor mef, muscle creatine kinase (MCK), truncated MCK (tMCK), myosin heavy chain (MHC), MHCK7, C5-12, murine creatine kinase enhancer element, skeletal fast-twitch troponin c gene element, slow-twitch cardiac troponin c gene element, the slow-twitch troponin I gene element, hypoxia-inducible nuclear factors, steroid-inducible element, and glucocorticoid response element (gre). In one aspect, the muscle-specific control element of the rAAV vector is truncated MCK (tMCK). In another aspect, the promoter and/or the muscle-specific control element of the rAAV vector is an MHCK7 promoter. In a further aspect, the MHCK promoter comprises, or consists essentially of, or yet further consists of the nucleotide sequence set forth in SEQ ID NO: 3 or an equivalent thereof and provides promoter function. In one embodiment, the genome of the rAAV vector disclosed herein comprises, or consists essentially of, or yet further consists of an intron comprising the nucleotide sequence set forth in SEQ ID NO: 5.

In some embodiments, the polynucleotide sequence encoding γ-sarcoglycan consists the nucleotide sequence set forth in SEQ ID NO: 1 or a polynucleotide sequence encoding γ-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to SEQ ID NO: 1 and retains γ-sarcoglycan activity.

In another aspect, a recombinant AAV vector described herein comprises, or consists essentially of a polynucleotide sequence encoding γ-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the amino acid sequence of human γ-sarcoglycan, which is set forth in SEQ ID NO: 2 (see Table 1), and the protein retains γ-sarcoglycan activity.

TABLE 1

Non-Limiting Examples of Protein and Nucleotide Sequences

| Sequence description | Sequence | SEQ ID NO |
|---|---|---|
| Human γ-sarcoglycan nucleotide sequence (codon-optimized) | ATGGTGAGGGAGCAGTACACCACAGCAACCGAGGG AATCTGCATCGAGAGGCCAGAGAACCAGTACGTGT ATAAGATCGGCATCTACGGCTGGCGGAAGAGATGT CTGTATCTGTTCGTGCTGCTGCTGCTGATCATCCT GGTGGTGAATCTGGCCCTGACCATCTGGATCCTGA AAGTGATGTGGTTTTCCCCAGCAGGAATGGGACAC CTGTGCGTGACAAAGGACGGACTGCGGCTGGAGGG AGAGTCTGAGTTCCTGTTTCCCCTGTATGCCAAGG AGATCCACAGCAGAGTGGATAGCTCCCTGCTGCTG CAGTCCACCCAGAACGTGACAGTGAACGCAAGGAA TAGCGAGGGAGAGGTGACCGGCAGACTGAAGGTCG GCCCCAAGATGGTGGAGGTGCAGAATCAGCAGTTC CAGATCAACTCCAATGACGGCAAGCCTCTGTTTAC AGTGGATGAGAAGGAGGTGGTGGTGGGCACCGACA AGCTGAGGGTGACAGGACCTGAGGGCGCCCTGTTC GAGCACTCTGTGGAGACCCCACTGGTGCGCGCAGA CCCTTTTCAGGATCTGAGGCTGGAGAGCCCAACAC GCAGCCTGTCCATGGACGCACCCAGAGGCGTGCAC ATCCAGGCACACGCAGGCAAGATCGAGGCCCTGAG CCAGATGGATATCCTGTTCCACTCTAGCGACGGCA TGCTGGTGCTGGATGCCGAGACCGTGTGCCTGCCT AAGCTGGTGCAGGGCACATGGGGCCCATCTGGCTC CTCTCAGAGCCTGTACGAGATCTGCGTGTGCCCAG ATGGCAAGCTGTATCTGTCCGTGGCCGGCGTGTCT ACCACATGCCAGGAGCACAACCACATCTGTCTGTG A | 1 |
| Human γ-sarcoglycan, amino acid sequence | MVREQYTTATEGICIERPENQYVYKIGIYGWRKRC LYLFVLLLIILVVNLALTIWILKVMWFSPAGMGH LCVTKDGLRLEGESEFLFPLYAKEIHSRVDSSLLL QSTQNVTVNARNSEGEVTGRLKVGPKMVEVQNQQF QINSNDGKPLFTVDEKEVVVGTDKLRVTGPEGALF EHSVETPLVRADPFQDLRLESPTRSLSMDAPRGVH IQAHAGKIEALSQMDILFHSSDGMLVLDAETVCLP KLVQGTWGPSGSSQSLYEICVCPDGKLYLSVAGVS TTCQEHNHICL | 2 |
| 5'ITR-MHCK7-Chimeric Intron-hSGCG-PolyA-3'ITR (full sequence between ITRs) | CTGCGCGCTCGCTCGCTCACTGAGGCCGCCCGGGC AAAGCCCGGGCGTCGGGCGACCTTTGGTCGCCCGG CCTCAGTGAGCGAGCGAGCGCGCAGAGAGGGAGTG GGGTTAACCAATTGGCGCGGCCGCAAGCTTGCATG TCTAAGCTAGACCCTTCAGATTAAAAATAACTGAG GTAAGGGCCTGGGTAGGGGAGGTGGTGTGAGACGC TCCTGTCTCTCCTCTATCTGCCCATCGGCCCTTTG GGGAGGAGGAATGTGCCCAAGGACTAAAAAAAGGC CATGGAGCCAGAGGGGCGAGGGCAACAGACCTTTC ATGGGCAAACCTTGGGGCCCTGCTGTCTAGCATGC CCCACTACGGGTCTAGGCTGCCCATGTAAGGAGGC AAGGCCTGGGGACACCCGAGATGCCTGGTTATAAT TAACCAGACATGTGGCTGCCCCCCCCCCCCCAAC ACCTGCTGCCTCTAAAAATAACCCTGTCCCTGGTG GATCCCTGCATGCGAAGATCTTCGAACAAGGCTG TGGGGGACTGAGGGCAGGCTGTAACAGGCTTGGGG GCCAGGGCTTATACGTGCCTGGGACTCCCAAAGTA TTACTGTTCCATGTTCCCGGCGAAGGGCCAGCTGT CCCCCGCCAGCTAGACTCAGCACTTAGTTTAGGAA CCAGTGAGCAAGTCAGCCCTTGGGGCAGCCCATAC AAGGCCATGGGGCTGGGCAAGCTGCACGCCTGGGT CCGGGTGGGCACGGTGCCCGGGCAACGAGCTGAA AGCTCATCTGCTCTCAGGGGCCCCTCCTGGGAC AGCCCCTCCTGGCTAGTCACACCCTGTAGGCTCCT CTATATAACCCAGGGGCACAGGGGCTGCCCTCATT CTACCACCACCTCCACAGCACAGACAGACACTCAG GAGCAGCCAGCGGCGCGCCCAGGTAAGTTTAGTCT TTTTGTCTTTTATTTCAGGTCCCGGATCCGGTGGT GGTGCAAATCAAAGAACTGCTCCTCAGTGGATGTT GCCTTTACTTCTAGGCCTGTACGGAAGTGTTACTT | 3 |

TABLE 1-continued

Non-Limiting Examples of Protein and Nucleotide Sequences

| Sequence description | Sequence | SEQ ID NO |
|---|---|---|
| | CTGCTCTAAAAGCTGCGGAATTGTACCCGGTACCA CCATGGTGAGGGAGCAGTACACCACAGCAACCGAG GGAATCTGCATCGAGAGGCCAGAGAACCAGTACGT GTATAAGATCGGCATCTACGGCTGGCGGAAGAGAT GTCTGTATCTGTTCGTGCTGCTGCTGCTGATCATC CTGGTGGTGAATCTGGCCCTGACCATCTGGATCCT GAAAGTGATGTGGTTTTCCCCAGCAGGAATGGGAC ACCTGTGCGTGACAAAGGACGGACTGCGGCTGGAG GGAGAGTCTGAGTTCCTGTTTCCCCTGTATGCCAA GGAGATCCACAGCAGAGTGGATAGCTCCCTGCTGC TGCAGTCCACCCAGAACGTGACAGTGAACGCAAGG AATAGCGAGGGAGAGGTGACCGGCAGACTGAAGGT CGGCCCCAAGATGGTGGAGGTGCAGAATCAGCAGT TCCAGATCAACTCCAATGACGGCAAGCCTCTGTTT ACAGTGGATGAGAAGGAGGTGGTGGTGGGCACCGA CAAGCTGAGGGTGACAGGACCTGAGGGCGCCCTGT TCGAGCACTCTGTGGAGACCCCACTGGTGCGCGCA GACCCTTTTCAGGATCTGAGGCTGGAGAGCCCAAC ACGCAGCCTGTCCATGGACGCACCCAGAGGCGTGC ACATCCAGGCACACGCAGGCAAGATCGAGGCCCTG AGCCAGATGGATATCCTGTTCCACTCTAGCGACGG CATGCTGGTGCTGGATGCCGAGACCGTGTGCCTGC CTAAGCTGGTGCAGGGCACATGGGGCCCATCTGGC TCCTCTCAGAGCCTGTACGAGATCTGCGTGTGCCC AGATGGCAAGCTGTATCTGTCCGTGGCCGGCGTGT CTACCACATGCCAGGAGCACAACCACATCTGTCTG TGACTCGAGGGCCGCAATAAAAGATCTTTATTTTC ATTAGATCTGTGTGTTGGTTTTTTGTGTGTCCTGC AGGGGCGCGCCTAATCTAGAGCATGGCTACGTAGA TAAGTAGCATGGCGGGTTAATCATTAACTACAAGG AACCCCTAGTGATGGAGTTGGCCACTCCCTCTCTG CGCGCTCGCTCGCTCACTGAGGCCGGGCGACCAAA GGTCGCCCGACGCCCGGGCTTTGCCCGGGCGGCCT CAGTGAGCGAGCGAGCGCGC | |
| MHCK7 Promoter | AAGCTTGCATGTCTAAGCTAGACCCTTCAGATTAA AAATAACTGAGGTAAGGGCCTGGGTAGGGGAGGTG GTGTGAGACGCTCCTGTCTCTCCTCTATCTGCCCA TCGGCCCTTTGGGGAGGAGGAATGTGCCCAAGGAC TAAAAAAAGGCCATGGAGCCAGAGGGGCGAGGGCA ACAGACCTTTCATGGGCAAACCTTGGGGCCCTGCT GTCTAGCATGCCCCACTACGGGTCTAGGCTGCCCA TGTAAGGAGGCAAGGCCTGGGGACACCCGAGATGC CTGGTTATAATTAACCCAGACATGTGGCTGCCCCC CCCCCCCAACACCTGCTGCCTCTAAAAATAACCC TGTCCCTGGTGGATCCCCTGCATGCGAAGATCTTC GAACAAGGCTGTGGGGGACTGAGGGCAGGCTGTAA CAGGCTTGGGGGCCAGGGCTTATACGTGCCTGGGA CTCCCAAAGTATTACTGTTCCATGTTCCCGGCGAA GGGCCAGCTGTCCCCCGCCAGCTAGACTCAGCACT TAGTTTAGGAACCAGTGAGCAAGTCAGCCCTTGGG GCAGCCCATACAAGGCCATGGGGCTGGGCAAGCTG CACGCCTGGGTCCGGGTGGGCACGGTGCCCGGGC AACGAGCTGAAAGCTCATCTGCTCTCAGGGGCCCC TCCTGGGACAGCCCCTCCTGGCTAGTCACACCC TGTAGGCTCCTCTATATAACCCAGGGGCACAGGGG CTGCCCTCATTCTACCACCACCTCCACAGCACAGA CAGACACTCAGGAGCAGCCAGC | 4 |
| Chimeric Intron | AGGTAAGTTTAGTCTTTTTGTCTTTTATTTCAGGT CCCGGATCCGGTGGTGGTGCAAATCAAAGAACTGC TCCTCAGTGGATGTTGCCTTTACTTCTAGGCCTGT ACGGAAGTGTTACTTCTGCTCTAAAAGCTGCGGAA TTGTACCC | 5 |
| PolyA | GGCCGCAATAAAAGATCTTTATTTTCATTAGATCT GTGTGTTGGTTTTTTGTG | 6 |
| 5' ITR | CTGCGCGCTCGCTCGCTCACTGAGGCCGCCCGGGC AAAGCCCGGGCGTCGGGCGACCTTTGGTCGCCCGG CCTCAGTGAGCGAGCGAGCGCGCAGAGAGGGAGTG GGGTT | 7 |

TABLE 1-continued

Non-Limiting Examples of Protein and Nucleotide Sequences

| Sequence description | Sequence | SEQ ID NO |
|---|---|---|
| 3' ITR | CCACTCCCTCTCTGCGCGCTCGCTCGCTCACTGAG GCCGGGCGACCAAAGGTCGCCCGACGCCCGGGCTT TGCCCGGGCGGCCTCAGTGAGCGAGCGAGCGCGC | 8 |
| Human γ-sarcoglycan nucleotide sequence (wild-type), GenBank U34976.1 | ATGGTGCGTGAGCAGTACACTACAGCCACAGAAGG CATCTGCATAGAGAGGCCAGAGAATCAGTATGTCT ACAAAATTGGCATTTATGGCTGGAGAAAGCGCTGT CTCTACTTGTTTGTTCTTCTTTTACTCATCATCCT CGTTGTGAATTTAGCTCTTACAATTTGGATTCTTA AAGTGATGTGGTTTTCTCCAGCAGGAATGGGCCAC TTGTGTGTAACAAAAGATGGACTGCGCTTGGAAGG GGAATCAGAATTTTTATTCCCATTGTATGCCAAAG AAATACACTCCAGAGTGGACTCATCTCTGCTGCTA CAATCAACCCAGAATGTGACTGTAAATGCGCGCAA CTCAGAAGGGGAGGTCACAGGCAGGTTAAAAGTCG GTCCCAAAATGGTAGAAGTCCAGAATCAACAGTTT CAGATCAACTCCAACGACGGCAAGCCACTATTTAC TGTAGATGAGAAGGAAGTTGTGGTTGGTACAGATA AACTTCGAGTAACTGGGCCTGAAGGGGCTCTTTTT GAACATTCAGTGGAGACACCCCTTGTCAGAGCCGA CCCGTTTCAAGACCTTAGATTAGAATCCCCCACTC GGAGTCTAAGCATGGATGCCCCAAGGGGTGTGCAT ATTCAAGCTCACGCTGGGAAAATTGAGGCGCTTTC TCAAATGGATATTCTTTTTCATAGTAGTGATGGAA TGCTTGTGCTTGATGCTGAAACTGTGTGCTTACCC AAGCTGGTGCAGGGGACGTGGGGTCCCTCTGGCAG CTCACAGAGCCTCTACGAAATCTGTGTGTGTCCAG ATGGGAAGCTGTACCTGTCTGTGGCCGGTGTGAGC ACCACGTGCCAGGAGCACAGCCACATCTGCCTCTG A | 9 |
| AAV rh.74 capsid amino acid sequence | MAAGGGAPMADNNEGADGVGSSSGNWHCDSTWLGD RVITTSTRTWALPTYNNHLYKQISNGTSGGSTNDN TYFGYSTPWGYFDFNRFHCHFSPRDWQRLINNNWG FRPKRLNFKLFNIQVKEVTQNEGTKTIANNLTSTI QVFTDSEYQLPYVLGSAHQGCLPPFPADVFMIPQY GYLTLNNGSQAVGRSSFYCLEYFPSQMLRTGNNFE FSYNFEDVPFHSSYAHSQSLDRLMNPLIDQYLYYL SRTQSTGGTAGTQQLLFSQAGPNNMSAQAKNWLPG PCYRQQRVSTTLSQNNNSNFAWTGATKYHLNGRDS LVNPGVAMATHKDDEERFFPSSGVLMFGKQGAGKD NVDYSSVMLTSEEEIKTTNPVATEQYGVVADNLQQ QNAAPIVGAVNSQGALPGMVWQNRDVYLQGPIWAK IPHTDGNFHPSPLMGGFGLKHPPPQILIKNTPVPA DPPTTFNQAKLASFITQYSTGQVSVEIEWELQKEN SKRWNPEIQYTSNYYKSTNVDFAVNTEGTYSEPRP IGTRYLTRNL | 10 |
| rAAV vector polynucleotide sequence | ATGGCTGCCGATGGTTATCTTCCAGATTGGCTCGA GGACAACCTCTCTGAGGGCATTCGCGAGTGGTGGG ACCTGAAACCTGGAGCCCCGAAACCCAAAGCCAAC CAGCAAAAGCAGGACAACGGCCGGGGTCTGGTGCT TCCTGGCTACAAGTACCTCGGACCCTTCAACGGAC TCGACAAGGGGGAGCCCGTCAACGCGGCGGACGCA GCGGCCCTCGAGCACGACAAGGCCTACGACCAGCA GCTCCAAGCGGGTGACAATCCGTACCTGCGGTATA ATCACGCCGACGCCGAGTTTCAGGAGCGTCTGCAA GAAGATACGTCTTTTGGGGGCAACCTCGGGCGCGC AGTCTTCCAGGCCAAAAAGCGGGTTCTCGAACCTC TGGGCCTGGTTGAATCGCCGGTTAAGACGGCTCCT GGAAAGAAGAGACCGGTAGAGCCATCACCCCAGCG CTCTCCAGACTCCTCTACGGGCATCGGCAAGAAAG GCCAGCAGCCCGCAAAAAAGAGACTCAATTTTGGG CAGACTGGCGACTCAGAGTCAGTCCCCGACCCCTA ACCAATGGAGAACCACCAGCAGGCCCCTCTGGTC TGGGATCTGTACAATGGCTGCAGGCGGTGGCGCT CCAATGGCAGACAATAACGAAGGCGCCGACGGAGT GGGTAGTTCCTCAGGAAATTGGCATTGCGATTCCA CATGGCTGGGCGACAGAGTCATCACCACCAGCACC CGCACCTGGGCCCTGCCCACCTACAACAACCACCT CTACAAGCAAATCTCCAACGGGACCTCGGGAGGAA GCACCAACGACAACACCTACTTCGGCTACAGCACC CCCTGGGGGTATTTTGACTTCAACAGATTCCACTG CCACTTTTCACCACGTGACTGGCAGCGACTCATCA ACAACAACTGGGGATTCCGGCCCAAGAGGCTCAAC TTCAAGCTCTTCAACATCCAAGTCAAGGAGGTCAC GCAGAATGAAGGCACCAAGACCATCGCCAATAACC TTACCAGCACGATTCAGGTCTTTACGGACTCGGAA TACCAGCTCCCCGTACGTGCTCGGCTCGGCGCACCA GGGCTGCCTGCCTCCGTTCCCGGCGGACGTCTTCA TGATTCCTCAGTACGGGTACCTGACTCTGAACAAT GGCAGTCAGGCTGTGGGCCGGTCGTCCTTCTACTG CCTGGAGTACTTTCCTTCTCAAATGCTGAGAACGG GCAACAACTTTGAATTCAGCTACAACTTCGAGGAC GTGCCCTTCCACAGCAGCTACGCGCACAGCCAGAG CCTGGACCGGCTGATGAACCCTCTCATCGACCAGT ACTTGTACTACCTGTCCCGGACTCAAAGCACGGGC GGTACTGCAGGAACTCAGCAGTTGCTATTTTCTCA GGCCGGGCCTAACAACATGTCGGCTCAGGCCAAGA ACTGGCTACCCGGTCCCTGCTACCGGCAGCAACGC GTCTCCACGACACTGTCGCAGAACAACAACAGCAA CTTTGCCTGGACGGGTGCCACCAAGTATCATCTGA ATGGCAGAGACTCTCTGGTGAATCCTGGCGTTGCC ATGGCTACCCACAAGGACGACGAAGAGCGATTTTT TCCATCCAGCGGAGTCTTAATGTTTGGGAAACAGG GAGCTGGAAAAGACAACGTGGACTATAGCAGCGTG ATGCTAACCAGCGAGGAAGAAATAAAGACCACCAA CCCAGTGGCCACAGAACAGTACGGCGTGGTGGCCG ATAACCTGCAACAGCAAAACGCCGCTCCTATTGTA GGGGCCGTCAATAGTCAAGGAGCCTTACCTGGCAT GGTGTGGCAGAACCGGGACGTGTACCTGCAGGGTC CCATCTGGGCCAAGATTCCTCATACGGACGGCAAC TTTCATCCCTCGCCGCTGATGGGAGGCTTTGGACT GAAGCATCCGCCTCCTCAGATCCTGATTAAAAACA CACCTGTTCCCGCGGATCCTCCGACCACCTTCAAT CAGGCCAAGCTGGCTTCTTTCATCACGCAGTACAG TACCGGCCAGGTCAGCGTGGAGATCGAGTGGGAGC TGCAGAAGGAGAACAGCAAACGCTGGAACCCAGAG ATTCAGTACACTTCCAACTACTACAAATCTACAAA TGTGGACTTTGCTGTCAATACTGAGGGTACTTATT CCGAGCCTCGCCCCATTGGCACCCGTTACCTCACC GTAATCTGTAA | 11 |

In another aspect, described herein is a recombinant AAV vector comprising a polynucleotide sequence encoding functional γ-sarcoglycan that comprises, or consists essentially of, or yet further consists of a nucleotide sequence that hybridizes under stringent conditions to the nucleic acid sequence of SEQ ID NO: 1, or a complement thereof. Functional γ-sarcoglycan intends a γ-sarcoglycan polypeptide that retains γ-sarcoglycan activity. γ-sarcoglycan activity is critical for muscle function. γ-sarcoglycan is one of several sarcolemmal transmembrane glycoproteins that interact with dystrophin and forms the dystrophin-glycoprotein complex, which spans the sarcolemma and is comprised of dystrophin, syntrophin, α-dystroglycans and β-dystroglycans, and sarcoglycans including γ-sarcoglycan. The dystrophin-glycoprotein complex provides a structural link between the subsarcolemmal cytoskeleton and the extracellular matrix of muscle cells. Non-limiting example of muscle cells include cardiac, diaphragm, leg, pelvic girdle, shoulder and arm muscle cells. Further non-limiting examples of γ-sarcoglycan activity and consequences of γ-sarcoglycanopathy are described in Blake et al. (2002) Physiol Rev.; 82(2):291-329 and Tarakci et al. (2016) Front Biosci (Landmark Ed); 21:744-56.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodS04, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

In another aspect, the recombinant AAV vectors described herein may comprise, or consist essentially of, or yet further consist of a polynucleotide sequence encoding γ-sarcoglycan that is operably linked to a promoter and/or a muscle-specific control element. For example the muscle-specific control element is human skeletal actin gene element, cardiac actin gene element, myocyte-specific enhancer binding factor MEF, muscle creatine kinase (MCK), tMCK (truncated MCK), myosin heavy chain (MHC), MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypozia-inducible nuclear factors, steroid-inducible element or glucocorticoid response element (GRE). In one embodiment, a rAAV vector comprises the MHCK7 promoter (SEQ ID NO: 4).

An exemplary rAAV vector described herein is pAAV.MHCK7.hSCGC, which comprises the nucleotide sequence of SEQ ID NO: 3; wherein the MCHK7 promoter spans nucleotides 136-927 (SEQ ID NO: 4), an intron spans nucleotides 937-1084 (SEQ ID NO: 5), the γ-sarcoglycan sequence spans nucleotides 1094-1969 (SEQ ID NO: 1) and the polyA spans nucleotides 1976-2028 (SEQ ID NO: 6). See FIG. 1. In some cases, the only viral sequences included in a rAAV vector are the inverted terminal repeats, which are required for viral DNA replication and packaging. In some cases, the intron (SEQ ID NO: 5) spanning nucleotides 7-116, and the 5' UTR (SEQ ID NO: 7), spanning nucleotides 2128-2231, are derived from plasmid pCMVβ (Clontech). In certain cases, the 3' UTR comprises the sequence set forth in SEQ ID NO: 8. In certain cases, pAAV.MHCK7.hSCGC is packaged in an AAV rh.74 capsid.

DNA plasmids of the disclosure comprise rAAV genomes. The DNA plasmids are transferred to cells permissible for infection with a helper virus of AAV (e.g., adenovirus, El-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. In some embodiments, a rAAV vector comprises the inverted terminal repeat (ITR) sequences of AAV2. Production of pseudotyped rAAV is disclosed in, for example, WO 01/83692 which is incorporated by reference herein in its entirety. In certain aspects, a rAAV vector comprises the inverted ITR sequences of AAV2 and is encapsidated in a capsid of AAV rh.74. In certain cases, the genome of the rAAV vector comprises the polynucleotide sequence set forth in SEQ ID NO: 11. In certain cases, the AAV rh.74 capsid comprises the amino acid sequence set forth in SEQ ID NO: 10. In some embodiments, the rAAV vector comprises a polynucleotide that comprises, or consists essentially of, or yet further consists of a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 11 and encodes the capsid proteins VP1, VP2, and VP3 of the rAAV. In some embodiments, the rAAV vector comprises a polypeptide that comprises, or consists essentially of, or yet further consists of a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to amino acid sequence of AAV rh.74 VP3 which is set forth in SEQ ID NO: 10.

A method of generating a packaging cell line is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells. In certain cases, the genome of the rAAV vector comprises the polynucleotide sequence set forth in SEQ ID NO: 11. In certain cases, the AAV rh.74 capsid comprises the amino acid sequence set forth in SEQ ID NO: 10. In some embodiments, the rAAV vector comprises a polynucleotide that comprises, or consists essentially of, or yet further consists of a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 11 and encodes the capsid proteins VP1, VP2, and VP3 of the rAAV. In some embodiments, the rAAV vector comprises a polypeptide that comprises, or consists essentially of, or yet further consists of a sequence, e.g., at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to amino acid sequence of AAV rh.74 VP3 which is set forth in SEQ ID NO: 10.

General principles of rAAV production are reviewed in, for example, Carter, 1992, Current Opinions in Biotechnology, 1533-539; and Muzyczka, 1992, Curr. Topics in Microbial, and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62: 1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/U598/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13: 1244-1250; Paul et al. (1993) Human Gene Therapy 4:609-615; Clark et al. (1996) Gene Therapy 3: 1124-1132; U.S. Pat. Nos. 5,786,211; 5,871,982; and 6,258, 595. The foregoing documents are hereby incorporated by reference in their entirety herein, with particular emphasis on those sections of the documents relating to rAAV production.

The disclosure thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the disclosure comprise a rAAV genome. Embodiments include, but are not limited to, the rAAV named pAAV.MHCK7.hSCGC which comprises the polynucleotide sequence set forth in SEQ ID NO: 3.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the disclosure contemplates compositions comprising, or consisting essentially of rAAV of the present disclosure. Compositions described herein comprise, or consist essentially of rAAV in a pharmaceutically acceptable carrier. In one particular embodiment, the composition of this disclosure comprise, or consist essentially of of Lactated Ringer's Solution (LRS). The compositions may also comprise other ingredients such as diluents and adjuvants. Acceptable carriers, diluents and adjuvants are non-toxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-formig counterions such as sodium; and/or nonionic surfactants such as Tween, pluronics or polyethylene glycol (PEG). The compositions disclosed can be used for one or more of for one or more of treating γ-sarcoglycanopathy; increasing muscular force, muscle endurance, and/or muscle mass; reducing fibrosis; reducing contraction-induced injury; decreasing fatty infiltration; and/or decreasing central nucleation in a subject in need thereof, and/or treating muscular dystrophy reducing degenerating fibers or necrotic fibers; reducing inflammation; elevating creatine kinase levels; treating myofiber atrophy and hypertrophy, and/or decreasing dystrophic calcification in a subject suffering from muscular dystrophy.

Titers of rAAV to be administered in methods of the disclosure will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times0^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the disclosure. The term "transduction" is used to refer to the administration/delivery of a polynucleotide of interest (e.g., a polynucleotide sequence encoding γ-sarcoglycan) to a recipient cell either in vivo or in vitro, via a replication-deficient rAAV described resulting in expression of γ-sarcoglycan by the recipient cell.

In one aspect provided herein are a methods for one or more of treating γ-sarcoglycanopathy; increasing muscular force, muscle endurance, and/or muscle mass; reducing fibrosis; reducing contraction-induced injury; decreasing fatty infiltration; and/or decreasing central nucleation in a subject in need thereof, and/or treating muscular dystrophy reducing degenerating fibers or necrotic fibers; reducing inflammation; elevating creatine kinase levels; treating myofiber atrophy and hypertrophy, and/or decreasing dystrophic calcification in a subject suffering from muscular dystrophy, comprising, or consisting essentially of, or yet further consisting of administering to the subject a therapeutically effective amount of a recombinant adeno-associated virus (AAV) vector, wherein the rAAV vector comprises, or consists essentially of, or yet further consists of a gene expression cassette comprising, or consisting essentially of, or yet further consisting of a polynucleotide sequence encoding γ-sarcoglycan under the transcriptional control of a promoter, said cassette flanked by one or more AAV inverted terminal repeats. In some embodiments, said promoter is a muscle-specific control element. In one embodiment, the methods disclosed herein increase muscular force, muscle endurance, and/or muscle mass of one or more muscles of the subject. Non-limiting examples of muscles include heart, diaphragm, upper legs, lower legs, pelvic girdle shoulder, and arm muscles. In one specific embodiment, the muscular force, muscle endurance, and/or muscle mass is increased at least about 5%, at least about 10%, at least about 15%, at least about 20%, at least about 50%, or at least about 80% compared to an untreated control subject.

In one particular aspect, the subject is suffering from limb-girdle muscular dystrophy. In a further aspect, the subject is suffering from limb-girdle muscular dystrophy is limb-girdle muscular dystrophy type 2C.

The terms "administering" or "administration" in reference to delivering the polynucleotides to a subject include any route of introducing or delivering to a subject the polynucleotides to perform the intended function. Administration can be carried out by any suitable route, including orally, intranasally, parenterally (intravenously, intramuscularly, intraperitoneally, or subcutaneously), intracranially, or topically. Additional routes of administration include intraorbital, infusion, intraartenal, intracapsular, intracardiac, intraderrnal, intrapulmonary, intraspinal, intrasternal, intrathecal, intrauterine, intravenous, subarachnoid, subcapsular, subcutaneous, transmucosal, or transtracheal. Administration includes self-administration and the administration by another.

In one aspect, the methods disclosed herein comprise, or consist essentially of, or yet further consist of administering a composition comprising, or consisting essentially of, or yet further consisting of the rAAV vector and a pharmaceutically acceptable carrier. In a further aspect, the methods disclosed herein comprise, or consist essentially of, or yet further consist of administering the rAAV vector or the composition comprising, or consisting essentially of, or yet further consisting of the rAAV vector and a pharmaceutically acceptable carrier by intramuscular injection or intravenous injection. In a yet further aspect, the methods disclosed herein comprise, or consist essentially of, or yet further consist of administering the rAAV vector or the composition comprising, or consisting essentially of, or yet further consisting of the rAAV vector and a pharmaceutically acceptable carrier systemically. In one particular aspect, the methods disclosed herein comprise, or consist essentially of, or yet further consist of administering the rAAV vector or the composition comprising, or consisting essentially of, or yet further consisting of the rAAV vector and a pharmaceutically acceptable carrier parentally by injection, infusion, or implantation.

In one aspect, the polynucleotide sequence encoding γ-sarcoglycan of the rAAV vector for use in the methods described herein comprises, or consists essentially of, or yet further consists of the nucleotide sequence set forth in SEQ ID NO: 1. In another aspect, the polynucleotide sequence encoding γ-sarcoglycan of the rAAV vector encodes the amino acid sequence of SEQ ID NO: 2. In yet another aspect, the rAAV vector used in the methods disclosed herein comprises, or consists essentially of, or yet further consists of a self-complementary AAV vector genome. In one particular embodiment, the rAAV vector comprises, or consists essentially of, or yet further consists of a genome lacking AAV rep and cap DNA. In another embodiment, the rAAV vector is of the serotype AAV1, AAV2, AAV4, AAV5, AAV6, AAV7, AAV8, AAV9, AAV10, AAV11, AAV12, AAV13 or AAV rh74. In a further aspect, the rAAV vector is of the serotype AAV rh74 and the rAAV vector comprises, or consists essentially of, or yet further consists of an AAV rh.74 capsid. In a yet further aspect, AAV rh.74 capsid of the rAAV vector comprises, or consists essentially of, or yet further consists of the amino acid sequence set forth in SEQ ID NO: 10 or an equivalent thereof.

The rAAV vector used in the methods disclosed herein may further comprise, or consist essentially of a promoter and/or a muscle-specific control element and wherein the muscle-specific control element is operatively linked to the polynucleotide encoding γ-sarcoglycan. Non-limiting examples some muscle-specific control elements are human skeletal actin gene element, cardiac actin gene element, myocyte-specific enhancer binding factor mef, muscle creatine kinase (MCK), truncated MCK (tMCK), myosin heavy chain (MHC), MHCK7, C5-12, murine creatine kinase enhancer element, skeletal fast-twitch troponin c gene element, slow-twitch cardiac troponin c gene element, the slow-twitch troponin I gene element, hypoxia-inducible nuclear factors, steroid-inducible element, and glucocorticoid response element (gre). In one aspect, the muscle-specific control element of the rAAV vector is truncated MCK (tMCK). In another aspect, the promoter and/or the muscle-specific control element of the rAAV vector is an MHCK7 promoter. In a further aspect, the MHCK promoter comprises, or consists essentially of, or yet further consists of the nucleotide sequence set forth in SEQ ID NO: 3 or an equivalent thereof.

In one embodiment, the genome of the rAAV vector disclosed herein comprises an intron comprising the nucleotide sequence set forth in SEQ ID NO: 5.

The in vivo methods comprise, or consist essentially of, or yet further consist of the step of administering an effective dose, or effective multiple doses, of a composition comprising, or consisting essentially of, or yet further consisting of a rAAV of the disclosure to an animal (including a human being) in need thereof. If the dose is administered prior to development of a disorder/disease, the administration is prophylactic. If the dose is administered after the development of a disorder/disease, the administration is therapeutic. In embodiments of the disclosure, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the disclosure is muscular dystrophy, such as limb-girdle muscular dystrophy. In some embodiments, a disease contemplated for prevention or treatment with methods of the disclosure is limb-girdle muscular dystrophy type 2C (LGMD2C).

The term "muscular dystrophy" as used herein refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type ID congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 21 muscular dystrophy, limb-girdle type 21 muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In some embodiments, the subject is suffering from limb-girdle muscular dystrophy. In some embodiments, the subject is suffering from limb-girdle muscular dystrophy type 2C (LGMD2C).

There are at least nineteen forms of LGMD, and the forms are classified by their associated genetic defects.

| Type | Pattern of Inheritance | Gene or Chromosome |
|---|---|---|
| LGMD1A | Autosomal dominant | Myotilin gene |
| LGMD1B | Autosomal dominant | Lamin A/C gene |
| LGMD1C | Autosomal dominant | Caveolin gene |
| LGMD1D | Autosomal dominant | Chromosome 7 |
| LGMD1E | Autosomal dominant | Chromosome 6 |
| LGMD1F | Autosomal dominant | Chromosome 7 |
| LGMD1G | Autosomal dominant | Chromosome 4 |
| LGMD2A | Autosomal recessive | Calpain-3 gene |
| LGMD2B | Autosomal recessive | Dysferlin gene |
| LGMD2C | Autosomal recessive | Gamma-sarcoglycan gene |
| LGMD2D | Autosomal recessive | Alpha-sarcoglycan gene |
| LGMD2E | Autosomal recessive | Beta-sarcoglycan gene |
| LGMD2F | Autosomal recessive | Delta-sarcoglycan gene |
| LGMD2G | Autosomal recessive | Telethonin gene |
| LGMD2H | Autosomal recessive | TRIM32 |
| LGMD2I | Autosomal recessive | FKRP gene |
| LGMD2J | Autosomal recessive | Titin gene |
| LGMD2K | Autosomal recessive | POMT1 gene |
| LGMD2L | Autosomal recessive | ANO5 gene |

In some aspects, the disclosure relates to a method of treating muscular dystrophy (e.g., LGMD2C) in a subject, the method comprising, or consisting essentially of, or yet further consisting of administering to the subject a therapeutically effective amount of a rAAV vector encoding γ-sarcoglycan as described herein or a composition comprising, or consisting essentially of such a rAAV vector.

In some embodiments, the disclosure provides a method of increasing muscular force, muscle endurance and/or muscle mass in a subject suffering from muscular dystrophy (e.g., LGMD2C), the method comprising, or consisting essentially of, or yet further consisting of administering to the subject a therapeutically effective amount of a rAAV vector encoding γ-sarcoglycan as described herein or a composition comprising, or consisting essentially of such a rAAV vector.

In certain aspects, the disclosure encompasses a method of reducing contraction-induced injury in a subject suffering from muscular dystrophy (e.g., LGMD2C), the method comprising, or consisting essentially of, or yet further consisting of administering to the subject a therapeutically effective amount of a rAAV vector encoding γ-sarcoglycan as described herein or a composition comprising, or consisting essentially of such a rAAV vector.

In certain aspects, the disclosure encompasses a method of treating γ-sarcoglycanopathy in a subject, the method comprising, or consisting essentially of, or yet further consisting of administering to the subject a therapeutically effective amount of a rAAV vector encoding γ-sarcoglycan as described herein or a composition comprising, or consisting essentially of such a rAAV vector.

The disclosure also encompasses a method of reducing fibrosis in a subject suffering from muscular dystrophy (e.g., LGMD2C), the method comprising, or consisting essentially of, or yet further consisting of administering to the subject a therapeutically effective amount of a rAAV vector encoding γ-sarcoglycan as described herein or a composition comprising, or consisting essentially of such a rAAV vector. The term "fibrosis" as used herein refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include collagen, e.g., collagen 1, collagen 2 or collagen 3, and fibronectin.

In certain embodiments, a subject treated by the methods described herein may be a mammal. In some cases, a subject is a human, a non-human primate, a pig, a horse, a cow, a dog, a cat, a rabbit, a mouse or a rat. A subject may be a human female or a human male. In some cases, the subject is a human subject between the ages of 1-7, 7-15, 16-25, 26-50, 50-70, or greater than 70 years of age. Other age ranges are contemplated and include without limitation, 5-10, 10-15, 15-20, 20-25, 25-30, 30-40, 40-50, 60-70, or greater than 70 years of age, as well as any range comprised by the foregoing.

As used herein, the term "patient in need" or "subject in need" refers to a patient or subject at risk of, or suffering from, a disease, disorder or condition that is amenable to treatment or amelioration with a rAAV comprising a nucleic acid sequence encoding γ-sarcoglycan or a composition comprising, or consisting essentially of such a rAAV provided herein. A patient or subject in need may, for instance, be a patient or subject diagnosed with a disease associated with the malfunction of γ-sarcoglycan, such as LGMD2C. A subject may have a mutation or a malfunction in a γ-sarcoglycan gene or protein. "Subject" and "patient" are used interchangeably herein.

Combination therapies comprising, or consisting essentially of, or yet further consisting of one or more of the compositions disclosed herein and a corticosteroid are also contemplated by the disclosure. Combination as used herein includes simultaneous treatment or sequential treatment. Combinations of methods of the disclosure with standard medical treatments (e.g., corticosteroids) are specifically contemplated, as are combinations with novel therapies. In some embodiments, a subject may be treated with a steroid (e.g., prednisone, prednisolone, deflazacort) to prevent or to reduce an immune response to administration of a rAAV described herein. In certain cases, a subject may receive apheresis or another immune modulator if the subject expresses antibodies to the rAAV described herein.

A therapeutically effective amount of the rAAV vector is in some embodiments a dose of rAAV ranging in one or more administrations in ranges from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e14 vg/kg, or about 1e13 vg/kg to about 2e14 vg/kg, or 1e13 vg/kg to about 3e14 vg/kg, or about 1x13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg. The disclosure also comprises, or consists essentially of, or yet further consists of compositions comprising, or consisting essentially of, or yet further consisting of these ranges of rAAV vector.

For example, a therapeutically effective amount of rAAV vector is a dose of 1e13 vg/kg, about 2e13 vg/kg, about 3e13 vg/kg, about 4e13 vg/kg, about 5e13 vg/kg, about 6e13 vg/kg, about 7e13 vg/kg, about 8e13 vg/kg, about 9e13 vg/kg, about 1e14 vg/kg, about 2e14 vg/kg, about 3e14 vg/kg, about 4e14 vg/kg and 5e14 vg/kg. The disclosure also comprises, or consists essentially of, or yet further consists of compositions comprising, or consisting essentially of, or yet further consisting of these doses of rAAV vector.

A therapeutic effective amount of rAAV is in some embodiments a dose of rAAV ranging from about 1e14 vg/kg to about 1e15 vg/kg or about 1e15 vg/kg to about 1e16 vg/kg. In some embodiments, the disclosure provides methods of administering an rAAV vector of the disclosure to subject at a dose of about 1e14 vg/kg, about 1.5e14 vg/kg, about 2e14 vg/kg, about 2.5e14 vg/kg, about 3e14 vg/kg, about 3.5e14 vg/kg, about 4e14 vg/kg, about 4.5e14 vg/kg, about 5e14 vg/kg, about 5.5e14 vg/kg, about 6e14 vg/kg, about 6.5e14 vg/kg, about 7e14 vg/kg, about 7.5e14 vg/kg, about 8e14 vg/kg, about 8.5e14 vg/kg about 9e14 vg/kg, about 9.5e14 vg/kg about 1e15 vg/kg, about 1.5e15 vg/kg, about 2e15 vg/kg, about 2.5e15 vg/kg, about 3e15 vg/kg, about 3.5e15 vg/kg, about 4e15 vg/kg, about 4.5e15 vg/kg, or about 5e15 vg/kg. In some embodiments, the disclosure provides methods of administering an rAAV vector of the disclosure to subject at a total dose of about 4.0e14 vg/kg, about 4.1e14 vg/kg, about 4.2e14 vg/kg, about 4.3e14 vg/kg, about 4.4e14 vg/kg, about 4.5e14 vg/kg, about 4.6e14 vg/kg, about 4.7e14 vg/kg, about 4.8e14 vg/kg, about 4.9e14 vg/kg, about 5.0e14 vg/kg, about 5.1e14 vg/kg, about 5.2e14 vg/kg, about 5.3e14 vg/kg, about 5.4e14 vg/kg, about 5.5e14 vg/kg about 5.6e14 vg/kg, about 5.7e14 vg/kg about 5.8e14 vg/kg, about 5.9e14 vg/kg, or about 6e14 vg/kg.

In various embodiments, the administering step may comprise administering the total dose in 1, 2, 3, 4, 5, 6, 7, 8, 9, 10 or more divided doses. For examples, the total dose may be delivered by injection to multiple sites on the subject or to the subject spaced over several minutes, several hours, or several days.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the disclosure may be chosen and/or matched by those skilled in the art taking into account the infection and/or disease state being treated and the target cells/tissue(s) that are to express the γ-sarcoglycan.

The disclosure provides for local administration and systemic administration of an effective dose of rAAV and compositions of the disclosure. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present disclosure may be accomplished by using any physical method that will transport the rAAV recombinant vector into the target tissue of an animal. Administration according to the disclosure includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV).

Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the disclosure. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the disclosure results in sustained expression of γ-sarcoglycan. The present disclosure thus provides methods of administering/delivering rAAV which express γ-sarcoglycan to a mammalian subject, preferably a human being. These methods include transducing tissues (including, but not limited to, tissues such as muscle, organs such as liver and brain, and glands such as salivary glands) with one or more rAAV of the present disclosure. Transduction may be carried out with gene cassettes comprising tissue specific control elements. For example, one embodiment of the disclosure provides methods of transducing muscle cells and muscle tissues directed by muscle specific control elements, including, but not limited to, those derived from the actin and myosin gene families, such as from the myoD gene family [See Weintraub et ah, Science, 251: 761-766 (1991)], the myocyte-specific enhancer binding factor MEF-2 [Cserjesi and Olson, Mol Cell Biol 11: 4854-4862 (1991)], control elements derived from the human skeletal actin gene [Muscat et al, Mol Cell Biol, 7: 4089-4099 (1987)], the cardiac actin gene, muscle creatine kinase sequence elements [See Johnson et ah, Mol Cell Biol, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et ah, Proc Natl Acad Sci USA, 88: 5680-5684 (1991)), steroid-inducible elements and promoters including the glucocorticoid response element (GRE) (See Mader and White, Proc. Natl. Acad. Sci. USA 90: 5603-5607 (1993)), and other control elements.

Muscle tissue is an attractive target for in vivo DNA delivery, because it is not a vital organ and is easy to access. The disclosure contemplates sustained expression of a transgene (e.g., γ-sarcoglycan) from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

Thus, also described herein are methods of administering an effective dose (or doses, administered essentially simultaneously or doses given at intervals) of rAAV that encode γ-sarcoglycan to a mammalian subject in need thereof.

Further provided herein are kits comprising, or consisting essentially of, or yet further consisting of, any of one or more of the embodiments disclosed herein and optional instructions for use. The kits can comprise, or consist essentially of, or yet further consist of one or more of the compositions disclosed herein and a corticosteroid or one or more of the combination therapy provided herein and optional instructions for use.

It is to be understood that the present disclosure is not limited to particular aspects described, as such may, of course, vary. It is also to be understood that the terminology used herein is for the purpose of describing particular embodiments only, and is not intended to be limiting, since the scope of the present disclosure will be limited only by the appended claims.

A number of embodiments of the disclosure have been described. Nevertheless, it will be understood that various modifications may be made without departing from the spirit and scope of the disclosure. Accordingly, the following examples are intended to illustrate but not limit the scope of disclosure described in the claims.

It is to be inferred without explicit recitation and unless otherwise intended, that when the present technology relates to a polypeptide, protein, polynucleotide or antibody, an equivalent or a biologically equivalent of such is intended within the scope of the present technology.

Citation of any patent, patent application, publication or any other document is not an admission that any of the foregoing is pertinent prior art, nor does it constitute any admission as to the contents or date of these publications or documents.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation and use of such terms and expressions do not exclude any equivalents of the features shown and described or segments thereof, and various modifications are possible within the scope of the technology claimed.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

The section headings used herein are for organizational purposes only and are not to be construed as limiting the subject matter described.

The disclosure is further described in the following Examples, which do not limit the scope of the disclosure described in the claims.

EXAMPLES

Example 1: scAAVrh74.tMCK.hSGCB Construction and Vector Potency

SGCG AAV construct containing a codon-optimized full-length human γ-sarcoglycan (SCGB) cDNA (SEQ ID NO: 1) as shown in FIG. 1 was constructed. The SGCG AAV construct was configured to be packaged using a self-complementary AAV backbone for more efficient transduction efficiency. The SGCG cDNA (969) was configured to be driven by a MHCK7 promoter (792 bp). The intron and 5' UTR were derived from plasmid pCMVβ (Clontech). The SGCG AAV construct had a consensus Kozak immediately in front of the ATG start and a small 53 bp synthetic polyA signal for mRNA termination. The cDNA was codon optimized for human usage and synthesized by GenScript (Piscataway, NJ). The only viral sequences included in this vector were the inverted terminal repeats of AAV2, which were required for both viral DNA replication and packaging.

The vector for this study was produced utilizing a triple-transfection method of HEK293 cells, under research grade conditions. Characterization of the vector following production included titer determination by qPCR with a supercoiled standard, endotoxin level determination (EU/mL) and a sterility assessment. The produced vector was analyzed by SDS-PAGE to verify banding pattern consistency with expected rAAV. Vector preps were titered with a linear plasmid standard and re-titered with a supercoiled plasmid standard. The vector was produced using plasmid containing the full-length human γ-sarcoglycan cDNA (NC_000013.11), a muscle specific MHCK7 promoter to drive expression, a consensus Kozak sequence (CCACC), an SV40 chimeric intron, synthetic polyadenylation site (53 bp) (FIG. 1). The SGCG expression cassette is cloned between AAV2 ITRs packaged into a self-complementary (sc) AAVrh.74 vector for enhanced transduction of cardiac tissue.

An overview of the study design is provided in TABLE 2. The dose values are determined by qPCR estimation of total number of vector genomes (vg). Inclusion of at least some partially full AAV capsids in a vector preparation may result in overestimation of dose by qPCR methods. Therefore determination of efficacy at a given dose (e.g. 5E+13) suggests efficacy may be observed at a lower qPCR-measured dose of vector when the vector is purified to remove partially full AAV capsids. The total dose (vg) and dose in terms of vector genomes per kilogram of subject (vg/kg) listed in Table 2 and throughout the Examples do not account for partially full AAV capsids.

TABLE 2

Overview of scAAVrh74.MHCK7.hSGCG Study Design

| Study Arm | Delivery Route | Animal Strain | Total Dose (vg) | Dose (vg/kg) | # Mice | Treatment Endpoint (months) | Analysis |
|---|---|---|---|---|---|---|---|
| Potency | IM | SGCG-/- | 3E+11 | N/A | 2 | 1 | IF |
| Potency | IV | SGCG-/- | 1E+13 | 5E+14 | 1 | 1.5 | IF |
| Efficacy | IV | SGCG-/- | 1E+12 | 5E+13 | 6 | 3 | IF, H&E, Western Blot, TA Phys, Dia Phys, Activity Cage, Histopath, Biodistribution qPCR, Serum Chem |
| Efficacy | IV | SGCG-/- | 4E+12 | 2E+14 | 6 | 3 | IF, H&E, Western Blot, TA Phys, Dia Phys, Activity Cage, Histopath, Biodistribution qPCR, Serum Chem |
| Efficacy | IV | SGCG-/- | 1E+13 | 5E+14 | 5 | 3 | IF, H&E, Western Blot, TA Phys, Dia Phys, Activity Cage, Histopath, Biodistribution qPCR, Serum Chem |
| Efficacy | IV | SGCG-/- | — | — | 6 | — | IF, H&E, Western Blot, TA Phys, Dia Phys, Activity Cage, Histopath, Serum Chem |
| Efficacy | IV | C57BL/6 | LRS | — | 6 | 3 | IF, H&E, Western Blot, TA Phys, Dia Phys, Activity Cage, Histopath, Serum Chem |

N/A: Not Applicable
IF: immunofluoresence; H&E: hematoxylin & eosin staining; TA Phys: specific force measurements and resistance to ECC injury in TA muscle; Dia Phys: specific force measurements in diaphragm muscle; Histopath: formal histopathology review; '—': uninjected.

All efficacy animals were treated at 4-8 weeks of age and necropsied 3 months post-injection. SGCG-/- negative control mice were necropsied at 4 months of age.

Potency determination of the scAAVrh.74.MHCK7.hSGCG test article was achieved by performing intramuscular and systemic injections of the vector into SGCG-/- mice. Wild type mice injected with Lactated Ringer's Solution (LRS) serve as a positive control and uninjected SGCG-/- mice serve as a negative control.

Figure 2:
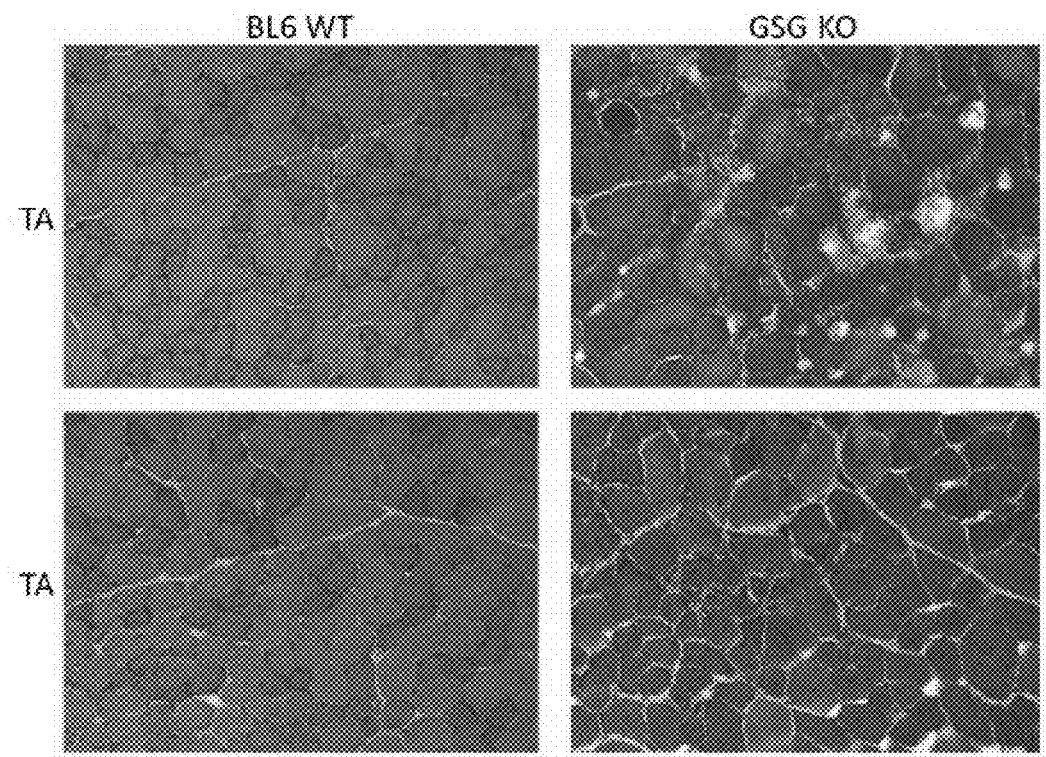
FIG. 2 depicts Hematoxylin and Eosin (H&E) staining of tibialis anterior (TA) muscle from 8 week old BL6 WT mice and γ-sarcoglycan knockout (γ-SG KO) mice showing a dystrophic phenotype in diseased mice.

Tibialis anterior (TA) muscle from 8 week old BL6 wild-type (WT) mice and γ-sarcoglycan knockout (γ-SG KO) mice was extracted and tissue sections were stained with Hematoxylin and Eosin (H&E) to view the histology of each muscle. Even at this very early age, γ-SG KO mice demonstrated a disease phenotype in the muscle with necrotic muscle fibers, inflammatory infiltrates, and the presence of fibrotic tissue. (FIG. 2).

The SGCG AAV construct was packaged into an AAV of rh.74 serotype to create the recombinant AAV (rAAV) termed scAAVrh.74.MHCK7.hSGCG. A total of 3 mice were injected to determine potency of scAAVrh.74.MHCK7.hSGCG. One C57BL/6 WT mouse injected with LRS and one uninjected SGCG−/− mouse served as the Positive and Negative Controls respectively. The remaining 3 mice were SGCG−/− and were injected via either IM in the LTA (n=2) or IV in the tail vein (n=1) with scAAVrh.74.MHCK7.hSGCG to determine if the vector lot is potent. The study design is summarized in TABLE 3.

TABLE 3 scAAVrh.74.MHCK7.hSGCG Potency Assay

| Number of Mice | Mouse Strain | Injection Material | Dose (vg total) | Delivery Route | Volume (μL) |
|---|---|---|---|---|---|
| 1 | SGCG−/− | N/A | Negative Control | N/A | N/A |
| 1 | C57BL/6 | LRS | Positive Control | IV | 200 |
| 2 | SGCG−/− | AAV.hSGCG | $3 \times 10^{11}$ vg | IM | 30 |
| 1 | SGCG−/− | AAV.hSGCG | $1 \times 10^{13}$ vg | IV | 460 (230/230) |

γ-SG KO mice were injected via intramuscular (IM) injection into the TA muscle at 4 weeks of age with scAAVrh.74.MHCK7.hSGCG at a dose of 3e10 vg total dose. Mice were euthanized at 4 weeks post-injection (8 weeks of age) and the TA muscle was extracted and fresh frozen in liquid nitrogen cooled methylbutane. Immunofluorescence (IF) staining for γ-sarcoglycan showed the absence of γ-sarcoglycan in uninjected right TA (RTA) muscle and showed nearly full restoration of membrane γ-sarcoglycan protein expression in injected left TA (LTA) muscle (FIG. 3A). Western blotting for γ-sarcoglycan (FIG. 3B) showed γ-sarcoglycan expression in two BL6 WT TA muscles; the absence of the protein in γ-SG KO TA muscle; and rrestoration of γ-sarcoglycan protein expression in TA muscle from injected mice #794 and #795.

Figure 3C:
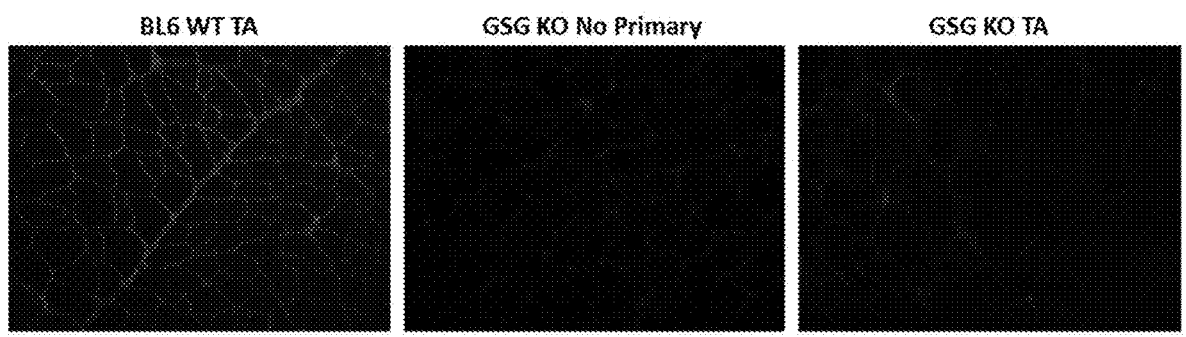

Delivery of scAAVrh.74.MHCK7.hSGCG via IM to SGCG−/− mice at the specified dose of $3\times10^{11}$ vg total dose resulted in 93.03% expression of hSGCG in the injected LTA muscles, which is similar to the levels of our previously studied γ-sarcoglycan (scAAVrh.74.MHCK7.hSGCB) vector. Immunofluorescence imaging of the vector dosed mice (Animals IDs: 794, 795) confirms expression of the hSGCG transgene (FIG. 3A). 20× images are included to visualize the amount of expression in injected muscle. As expected, the C57BL/6 WT mouse showed 100% expression of γ-sarcoglycan protein and the SGCG−/− mouse was completely absent for γ-sarcoglycan expression (FIG. 3C).

Figure 7:
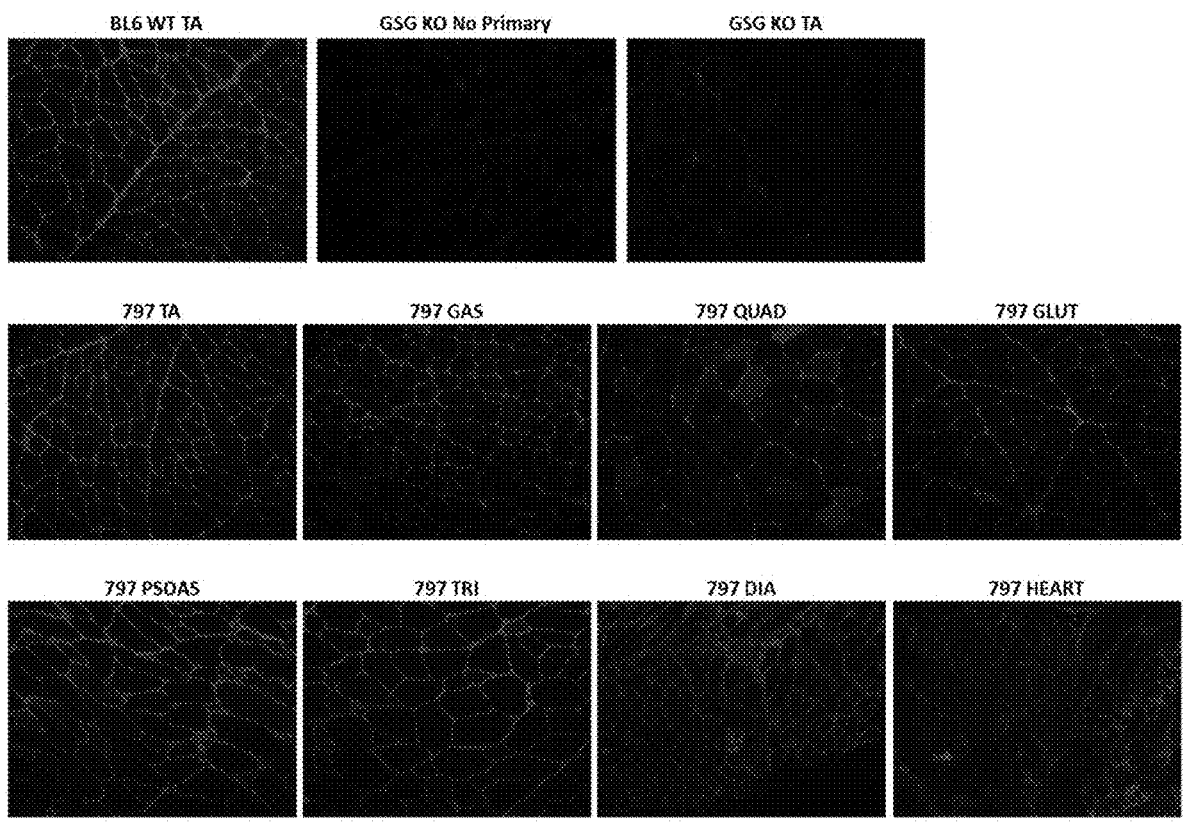
FIG. 7 depicts immunofluorescence staining of IV potency tissues. IF staining for γ-sarcoglycan in various skeletal muscles, diaphragm, and heart demonstrates robust expression with rare negative fibers 6 weeks following systemic delivery of scAAVrh. 74.MHCK7.hSGC G.

Systemic injection through the tail vein to one SGCG−/− mouse (#797) resulted in high levels of expression of the hSGCG transgene. Applicant was able to accomplish ≥94.00% transduction in all skeletal muscles of this potency mouse treated with $1\times10^{13}$ vg total dose ($5\times10^{14}$ vg/kg) scAAVrh.74.MHCK7.hSGCG. The average percent expression of the AAV delivered hSGCG transgene across all skeletal muscles analyzed was 95.98%. Applicant was also able to achieve very high levels of transduction in heart upon systemic delivery. Representative 20× immunofluorescence images of all skeletal muscles along with the diaphragm and heart illustrating the widespread expression of hSGCG are shown in FIG. 7.

Example 2: Potency and Toxicity of scAAVrh74.tMCK.hSGCB Vector in BL6 WT Mice

Figure 4A:
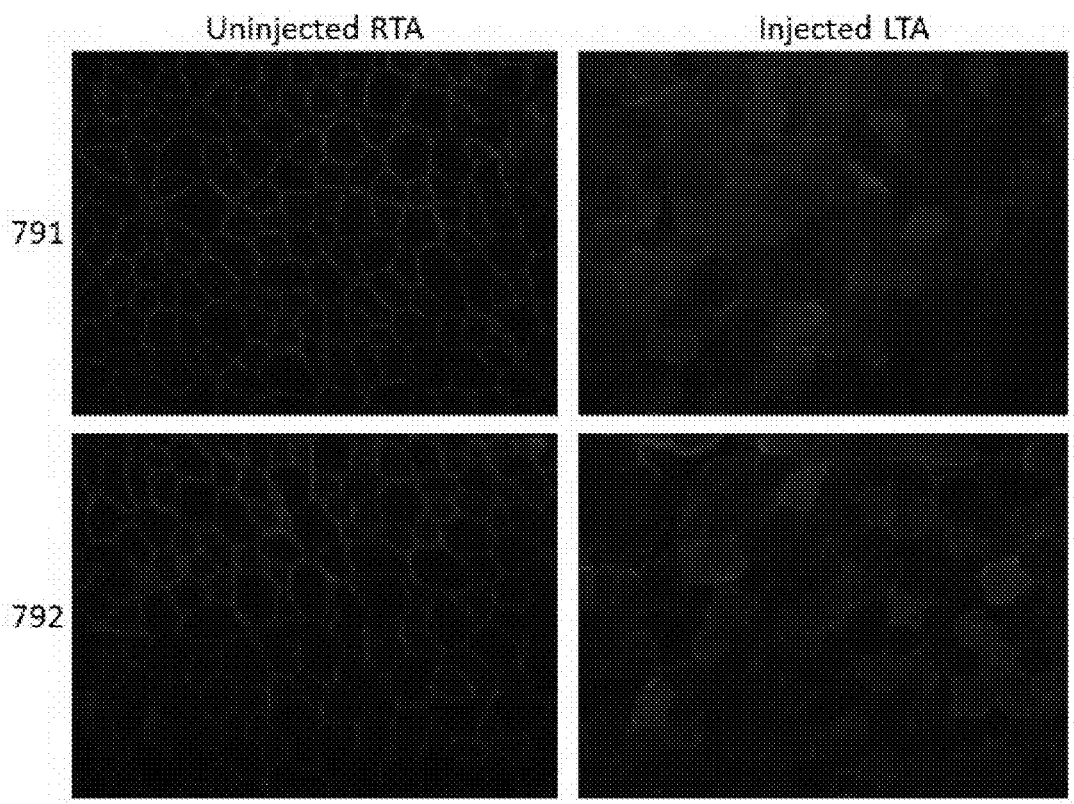
FIGS. 4A-4B depict in vivo vector potency and toxicity in BL6 wild-type (WT) mice.
Figure 4B:
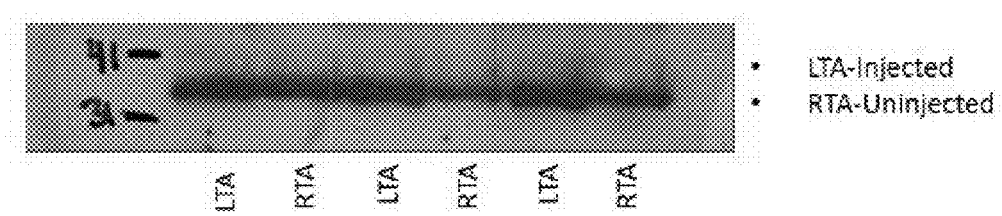
Figure 5:
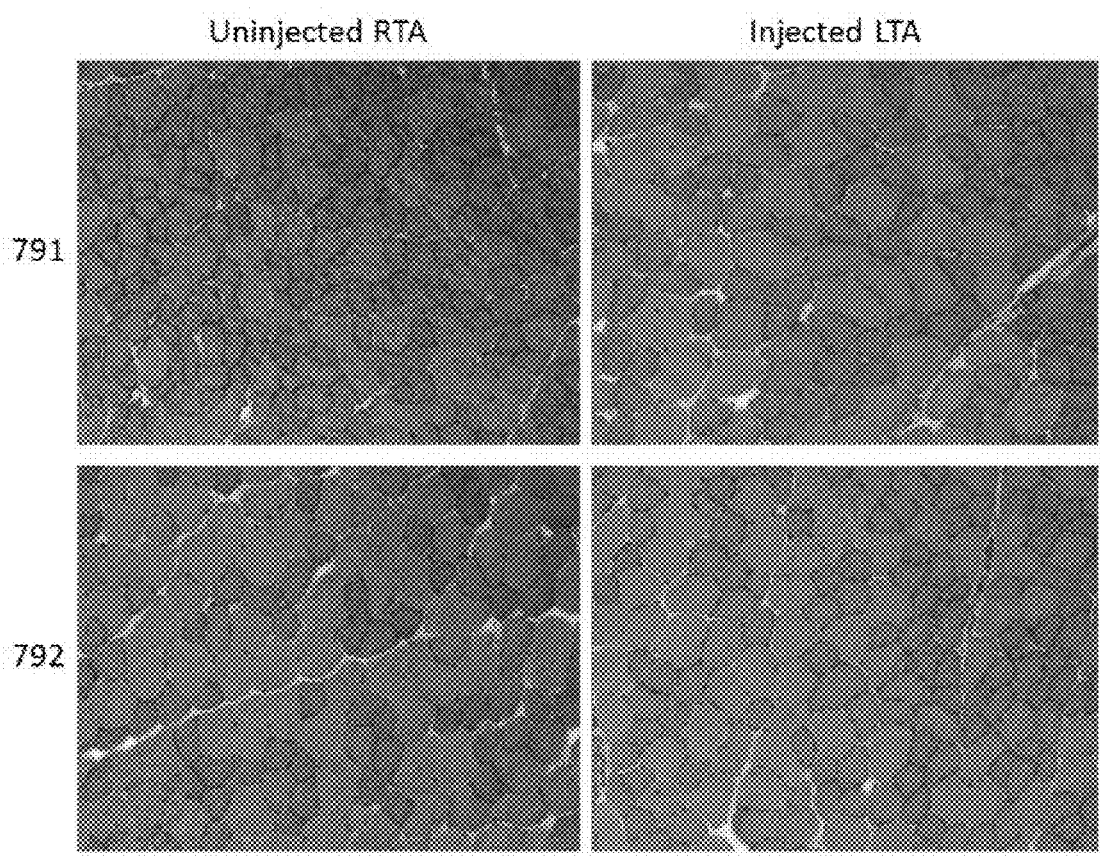
FIG. 5 depicts in vivo vector potency and toxicity in BL6 wild-type (WT) mice. H&E staining of uninjected and injected BL6 WT TA muscles shows no toxicity with complete absence of any central nuclei, necrotic fibers, inflammatory infiltration, or fibrotic tissue.

BL6 WT mice were injected via intramuscular (IM) injection into the TA muscle at 4 weeks of age with scAAVrh.74.MHCK7.hSGCG at a dose of 3e10 vg total dose. Mice were euthanized at 4 weeks post-injection (8 weeks of age) and the TA muscle was extracted and fresh frozen in liquid nitrogen cooled methylbutane. Immunofluorescence (IF) staining for γ-sarcoglycan showed the membrane staining for γ-sarcoglycan in uninjected right TA (RTA) muscle and showed intracellular staining indicative of overexpression of γ-sarcoglycan protein in injected left TA (LTA) muscle (FIG. 4A). Western blotting for γ-sarcoglycan (FIG. 4B) showed overexpression of the γ-sarcoglycan protein in the injected LTA muscle. H&E staining of TA muscle showed no toxicity with complete absence of any central nuclei, necrotic fibers, inflammatory infiltration, or fibrotic tissue in either uninjected RTA or injected LTA (FIG. 5).

Figure 6:
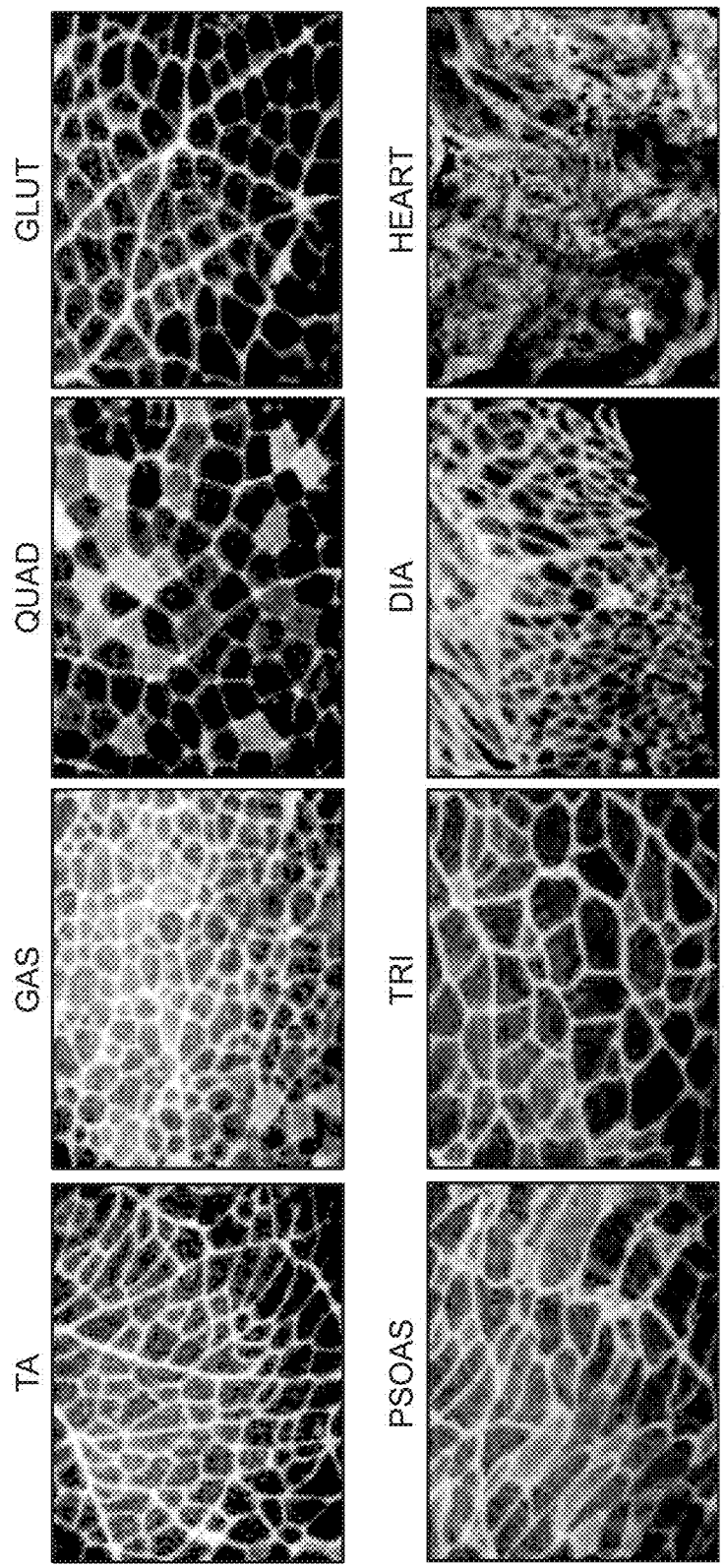
FIG. 6 depicts immunofluorescence staining for γ-sarcoglycan on TA, gastrocnemius (GAS), quadriceps (QUAD), gluteus (GLUT), PSOAS, TRICEP, diaphragm, and heart muscle, demonstrating widespread expression of γ-sarcoglycan.

Example 3: Gene Expression after Systemic Delivery of scAAVrh.74.tMCK.hSGCB

γ-SG KO mice were injected intravenously in the tail vein at 4-5 weeks of age with 1e12 vg total dose (5e13 vg/kg). Mice were euthanized after 6 weeks of treatment. Immunofluorescence staining on TA, gastrocnemius (GAS), quadriceps (QUAD), gluteus (GLUT), PSOAS, TRICEP, diaphragm, and heart muscle demonstrated widespread expression of γ-sarcoglycan (FIG. 6).

Efficacy determination of the scAAVrh.74.MHCK7.hSGCG test article was achieved by performing systemic injections in SGCG−/− mice (genotype: sgcgC57) using a single dose ($1\times10^{13}$ vg total dose, $5\times10^{14}$ vg/kg). Systemic injection of scAAVrh.74.MHCK7.hSGCG at clinical dose ($1\times10^{12}$ vg total dose ($5\times10^{13}$ vg/kg)), mid dose ($4\times10^{12}$ vg total dose ($2\times10^{14}$ vg/kg)), and high dose ($1\times10^{13}$ vg total dose ($5\times10^{14}$ vg/kg)) into the tail vein of SGCG−/− mouse with euthanasia 3 months post-injection.

Figure 8A:
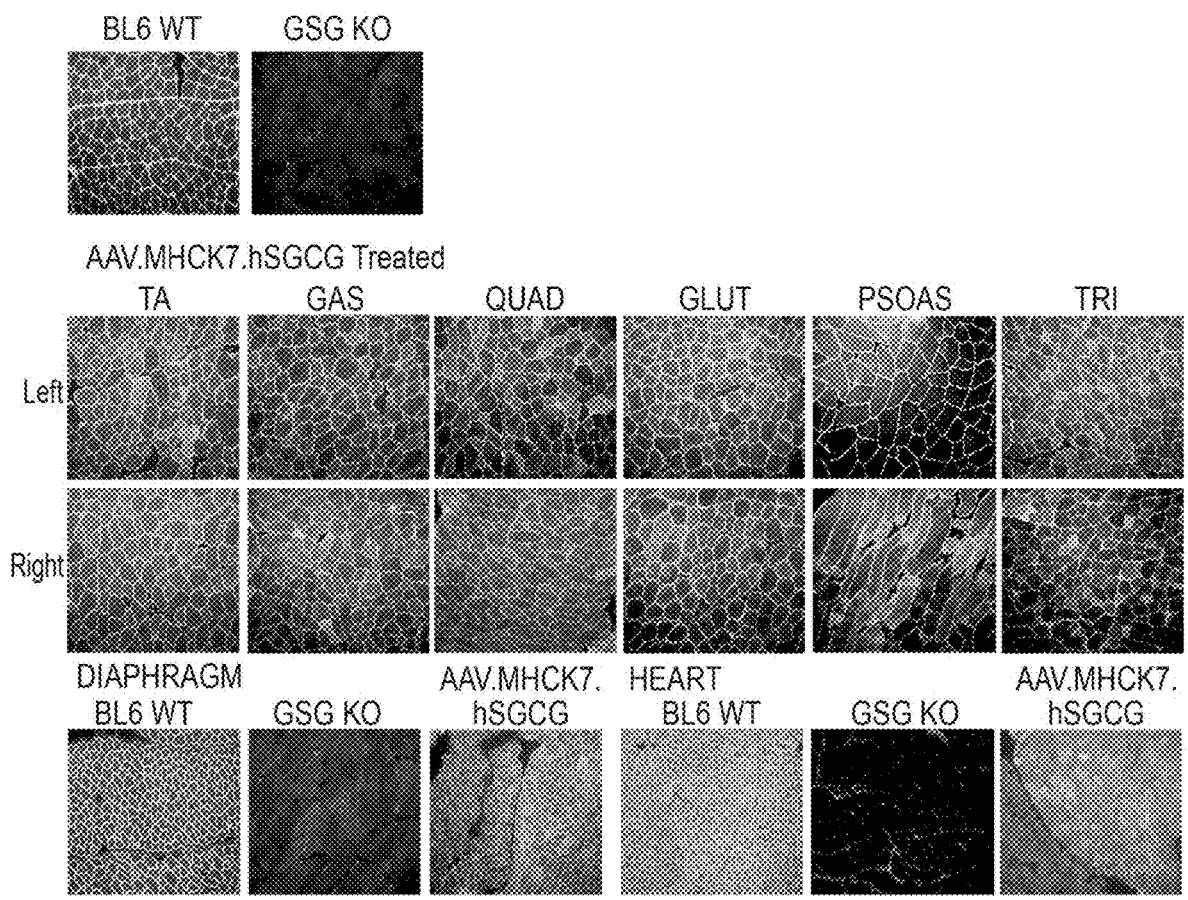
FIGS. 8A-8B show expression of SGCG in IV treated animals. Immunofluorescence imaging of skeletal muscles, diaphragm, and heart from SGCG−/− mice intravenously injected with 1e13 vg total dose scAAVrh.74.MHCK7.hSGCG is shown in representative 20× images (FIG. 8A). Western blotting shows hSGCG expression in all skeletal muscles and the heart from mice given intravenous delivery of scAAVrh.74.MHCK7.hSGCG (FIG. 8B).
Figure 8B:
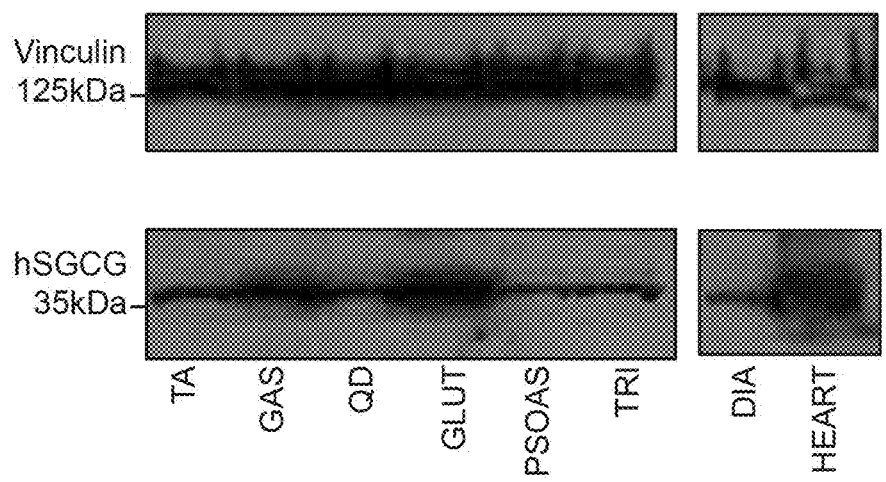

Following the results of our scAAVrh.74.MHCK7.hSGCG potency assay, Applicant delivered vector through a tail vein injection to 5 SGCG−/− mice at our potency dose of $1\times10^{13}$ vg total dose ($5\times10^{14}$ vg/kg) to assess transgene expression and efficacy of our vector when delivered systemically at an extended time point of 3 months. Mice were injected at 4 weeks of age and a full necropsy was performed at 3 months post-injection. All skeletal muscles discussed above in the potency assay along with the diaphragm and heart were extracted for analysis. Organs including the lungs, kidneys, liver, spleen, and gonads were also removed for toxicology and biodistribution studies. In short, hSGCG transgene expression remained high following 3 months treatment and all muscles from treated mice were again highly transduced. This was accompanied by improved muscle histopathology and improved TA and diaphragm muscle function. Systemic delivery of the scAAVrh.74.MHCK7.hSGCG vector did not induce any toxicity in muscles or organs γ-Sarcoglycan Expression Immunofluorescence staining for human γ-sarcoglycan was used to determine hSGCG transgene expression in six skeletal muscles, both left and right, in additional to the diaphragm and heart of all the SGCG−/− mice given a systemic injection of the scAAVrh.74.MHCK7.hSGCG vector. These muscles included the TA, GAS, QUAD, GLUT, PSOAS, TRI. For the purposes of expression analysis and transduction efficiency, images for the left and right muscles from 5 treated mice were utilized for quantification. Four 20× images were taken of each muscle and the percent of hSGCG positive fibers (number of positive expressing fibers/total number of fibers) was determined for each image resulting in the average percent transduction for each muscle from each mouse. FIG. 8A shows representative images from the treated mice and demonstrate the high levels of expression averaging 92.26% across all muscles quantified including the diaphragm. Applicant again also saw high levels of transduction in cardiac muscle in all vector treated mice. FIG. 8B shows Western blotting that confirms expression of the hSGCG transgene in all skeletal muscles and the heart from mice given intravenous delivery of the scAAVrh.74.MHCK7.hSGCG vector. TABLE 4 lists the average percent expression among the four 20× images for each muscle from each mouse, along with the average for each muscle across all 5 mice.

TABLE 4

Average Percent γ-Sarcoglycan Transgene Expression

| Animal ID | 5229 | 5230 | 5231 | 5232 | 5233 | Average |
|---|---|---|---|---|---|---|
| Muscle | | | | | | |
| TA | 97.79 | 97.79 | 99.54 | 99.13 | 96.59 | 98.17 |
| GAS | 90.88 | 90.88 | 74.14 | 97.67 | 93.49 | 89.41 |
| QUAD | 88.37 | 88.37 | 96.85 | 95.01 | 76.15 | 88.95 |
| GLUT | 96.19 | 96.19 | 91.12 | 100 | 92.83 | 95.27 |
| PSOAS | 97.55 | 97.55 | 99.01 | 49.88 | 97.92 | 88.38 |
| TRI | 97.32 | 97.32 | 99.31 | 94.98 | 93.31 | 96.45 |
| DIA | 93.02 | 93.02 | 75.56 | 97.14 | 87.22 | 89.19 |

Histopathology of Treated Muscle

Figure 9A:
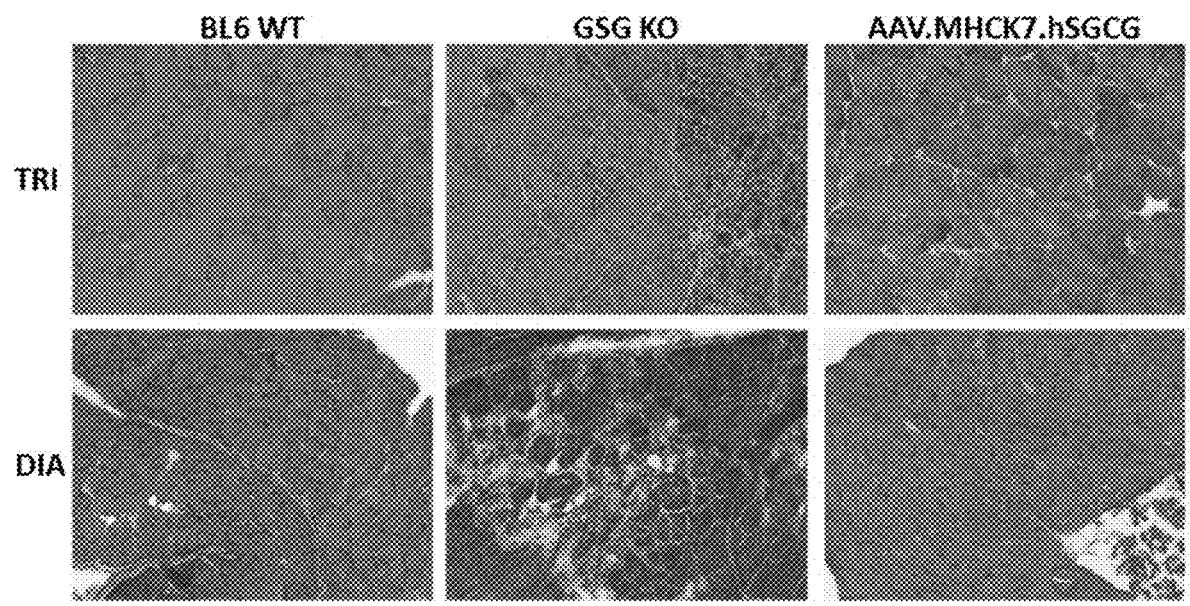
FIGS. 9A-9B show histological evaluation of tissues following systemic treatment. Hematoxylin & Eosin staining of TRI and DIA skeletal muscles in BL6 WT, untreated SGCG−/−, and AAV.MHCK7.hSGCG treated SGCG−/− mice shows the reversal of dystrophic pathology following treatment (FIG. 9A). Quantification of the percentage of fibers with central nucleation shows a decrease in treated muscles. BL6 WT (n=5), untreated SGCG−/− (n=6), AAV.MHCK7.hSGCG treated (n=5) (FIG. 9B). *=$p<0.001$, **=$p<0.0001$.
Figure 9B:
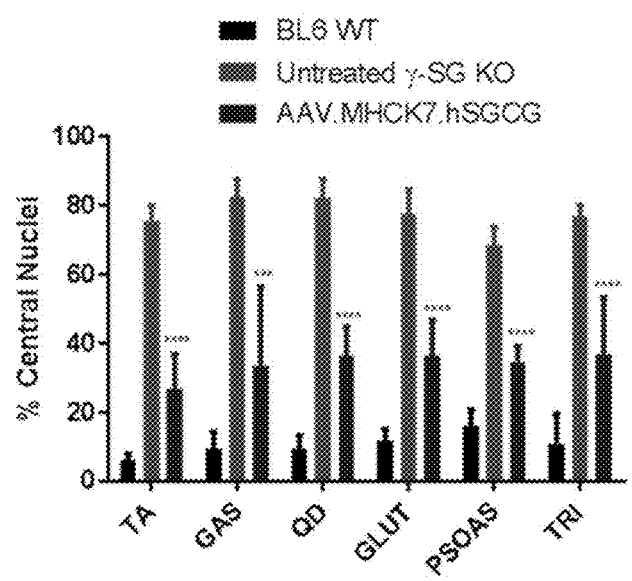
Figure 10B:
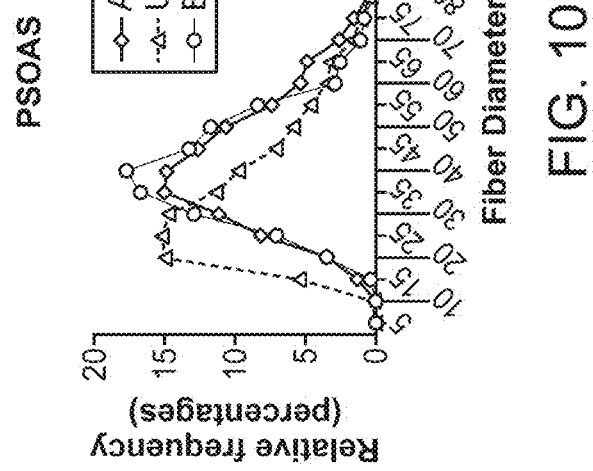
FIGS. 10A-10F show fiber diameter quantification. Quantification of fiber diameters was performed in the GAS (FIG. 10A), PSOAS (FIG. 10B), and TRI (FIG. 10C) of BL6 WT (n=5), untreated SGCG−/−(n=6), and AAV.MHCK7.hSGCG treated SGCG−/− (n=5) mice and normalization of fiber diameter distribution following treatment. Average fiber diameter is decreased in in the GAS (FIG. 10D), PSOAS (FIG. 10E), and TRI (FIG. 10F) muscle of untreated SGCG−/− mice and increased to WT levels in each muscle following AAV.MHCK7.hSGCG treatment in SGCG−/− mice. ****=$p<0.0001$.
Figure 10C:
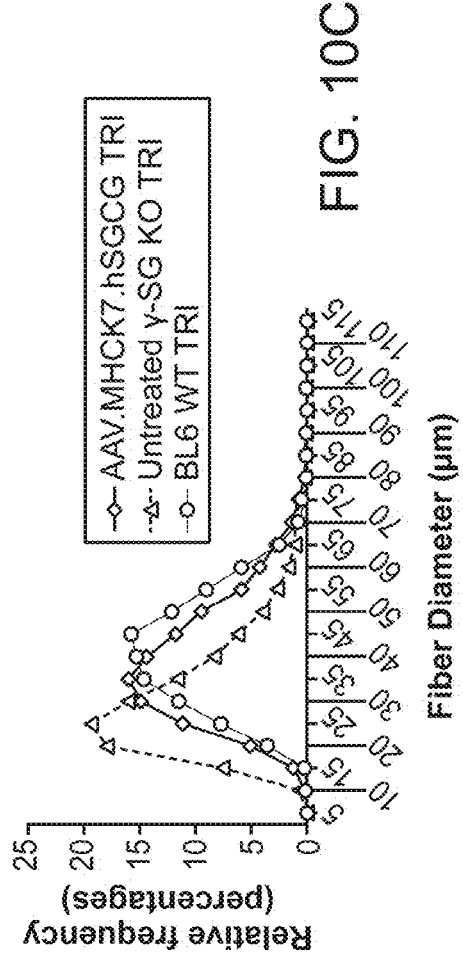
Figure 10A:
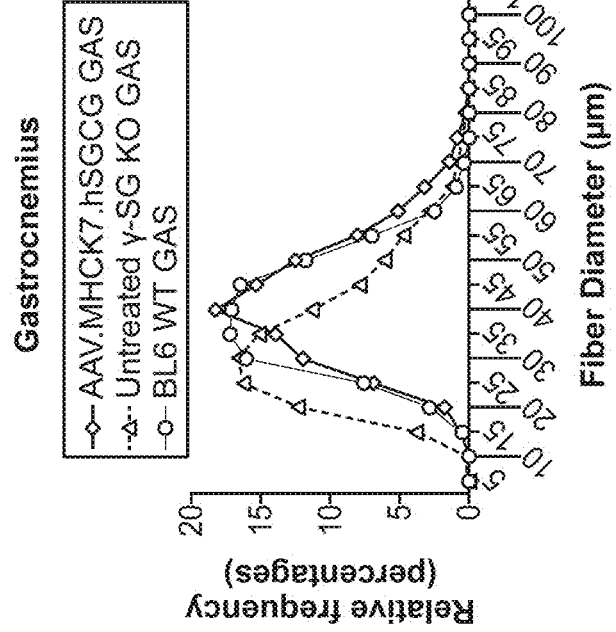
Figure 10F:
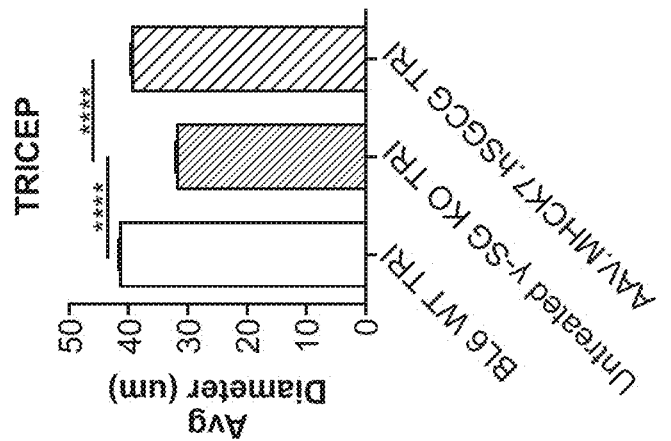
Figure 10E:
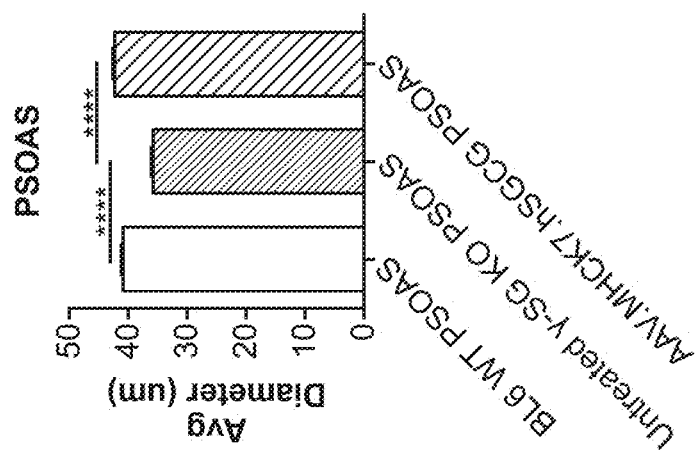
Figure 10D:
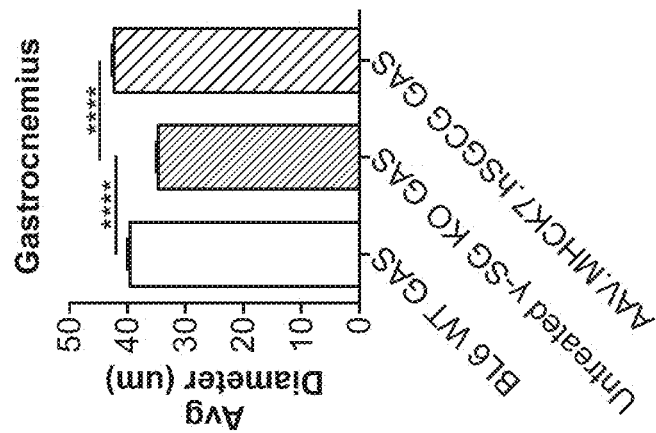

Muscles from SGCG−/− mice, both skeletal and cardiac, exhibit widespread myopathy including pronounced myofiber atrophy and hypertrophy with multiple focal areas of necrosis. Also present are increasing numbers of mononuclear cell inflammation (lymphocytes and macrophages, with scattered neutrophils) and increased dystrophic calcification, fatty infiltration, central nucleation, and fibrosis. Hematoxylin & eosin staining in FIG. 9A illustrates this dystrophic phenotype in SGCG−/− mice when compared to normal WT mice and the improvement of muscle pathology following treatment. Quantification of histological parameters shows a significant elevation of the number of centrally nucleated fibers in the skeletal muscles of SGCG−/− mice, followed by a reduction in central nucleation in numerous different skeletal muscles as a result of γ-sarcoglycan gene transfer (FIG. 9B). A more in-depth analysis of muscle histopathology reveals a normalization of fiber size distribution accompanied by an increase in average fiber diameter in diseased SGCG−/− mice treated with vector in all three muscles examined (GAS, PSOAS, and TRI) (FIGS. 10A-10F). The individual central nuclei counts and average fiber diameters for the various muscles were analyzed from each mouse.

Example 4: Physiological Deficits of γ-SG KO Mice

Sirius red stain will be performed to quantify the amount of fibrotic tissue. γ-SG KO mice and BL6 WT mice will be tested at 4 months of age to assess whether there are force deficits in skeletal muscle. The tibialis anterior (TA) muscle will be tested for a significant decrease in specific force and resistance to injury compared to controls. The diaphragm muscle will also be tested in a similar manner to detect any significant decreases. This measureable decrease will provide a functional outcome measure to establish efficacy for AAV.hSGCB therapy.

Example 5: Functional Outcomes After scAAVrh74.tMCK.hSGCB Treatment

Cohorts of γ-SG KO mice will be injected on a rolling basis for three-month studies to quantify efficacy and toxicity (TABLE 5). Mice will be subjected to activity cage analysis prior to euthanasia to determine overall activity of treated mice compared to γ-SG KO controls. TA and diaphragm muscle will be subjected to physiology analysis to determine specific force outputs and resistance to injury/fatigue. γ-SG KO muscles will be compared to BL6 WT controls to establish functional outcome measures that will be used to determine efficacy of treatment in treated mice. All skeletal muscles will be IF (immunofluorescence) stained for expression of γ-sarcoglycan, H&E stained for histopathology. Quantitative polymerase chain reaction (qPCR) will be performed on muscles and organs from injected mice to determine vector genome biodistribution.

TABLE 5

| Mouse Strain | Test Article | Human Dose | Sample Size | Endpoint |
|---|---|---|---|---|
| C57/BL6 | LR* | NA | 6 | 12 weeks |
| SGCG KO | LR | NA | 6 | 12 weeks |
| SGCG KO | scAAVrh74.MHCK7.SGCG | $5 \times 10^{13}$ vg/kg | 6 | 12 weeks |
| SGCG KO | scAAVrh74.MHCK7.SGCG | $1 \times 10^{14}$ vg/kg | 6 | 12 weeks |
| SGCG KO | scAAVrh74.MHCK7.SGCG | $2 \times 10^{14}$ vg/kg | 6 | 12 weeks |

Example 6: Functional Assessment of Systemic Delivery

Figure 11A:
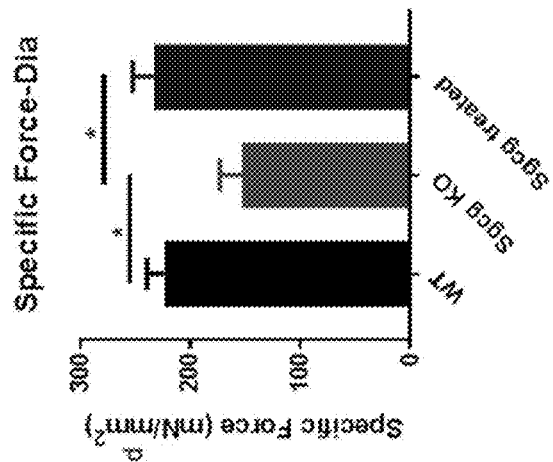
FIGS. 11A-11C show TA and diaphragm physiology. TA and DIA muscles of BL6 WT (n=5), untreated SGCG−/− (n=6), and AAV.MHCK7.hSGCG treated (n=5) mice subjected to measurement of normalized specific force production. TA muscle subjected to eccentric contraction injury protocol (FIG. 11A). Improvement in TA specific force output and resistance to contraction induced injury in treated SGCG−/− mice was observed (FIG. 11B). DIA specific force output was restored to WT levels in treated SGCG−/− mice (FIG. 11C). *=$p<0.05$, ****=$p<0.0001$.
Figure 11B:
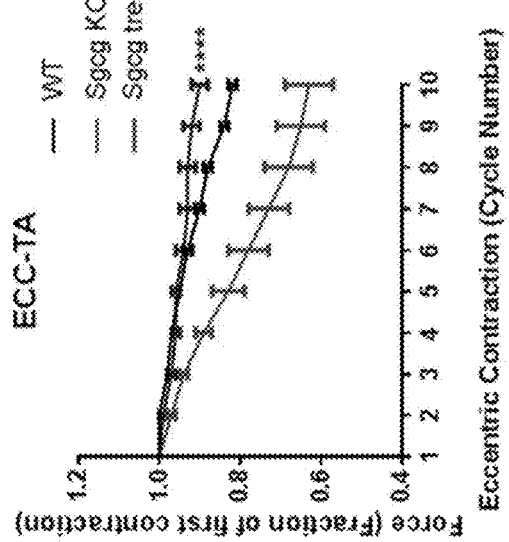
Figure 11C:
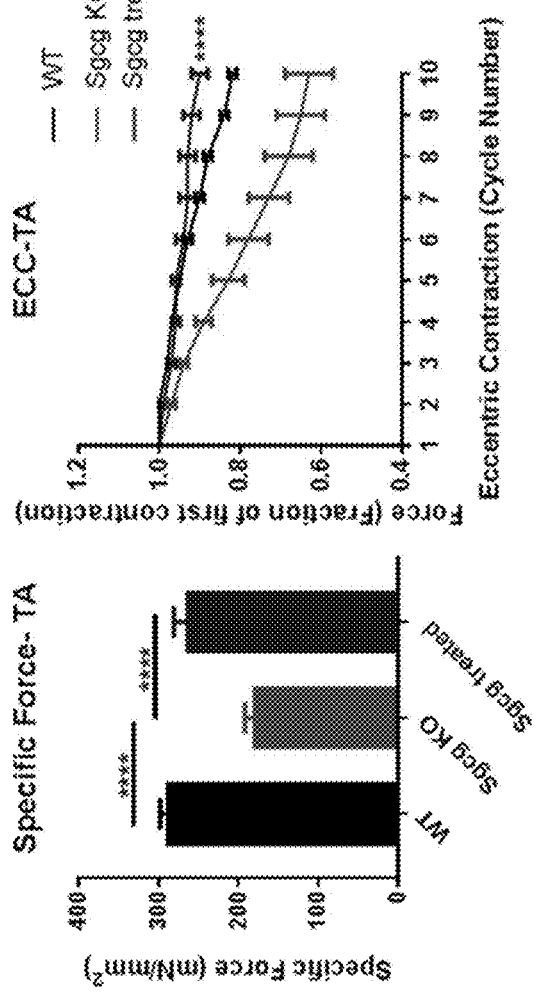

To determine whether hSGCG gene transfer provides a functional benefit to diseased muscle, Applicant assessed the functional properties of the TA and diaphragm muscle from SGCG−/− mice treated with scAAVrh.74.MHCK7.hSCGG. As outlined in Examples 1 to 5, Applicant first demonstrated histopathology in limb skeletal muscle and the diaphragms in mice in the absence of γ-sarcoglycan. In situ analysis of the TA muscle of untreated SGCG−/− mice revealed a statistically significant decrease of 37.68% in normalized specific force production compared to BL6 WT TA muscles (BL6 WT: 291.65 mN/mm$^2$ vs. SGCG−/−: 181.77 mN/mm$^2$). Specific force outputs were significantly increased to normal WT levels compared to SGCG−/− muscle following treatment (SGCG−/−: 181.77 mN/mm² vs. Treated: 266.02 mN/mm²) (FIG. 11A and FIG. 11C). One additional functional outcome measure to determine the functional benefits of hSGCG gene transfer is to assess the resistance to contraction induced injury in the TA muscle following repeated eccentric contractions. The TA muscle of normal BL6 WT mice untreated SGCG−/− mice lost only 18% of force production following a round of 10 eccentric contractions, compared to a 37% loss of force in untreated SGCG−/− TA muscle. Vector treated SGCG−/− muscles had an improvement to above WT levels where they saw only a 10% loss of force following the eccentric contraction (ECC) protocol (FIG. 11B).

Figure 12:
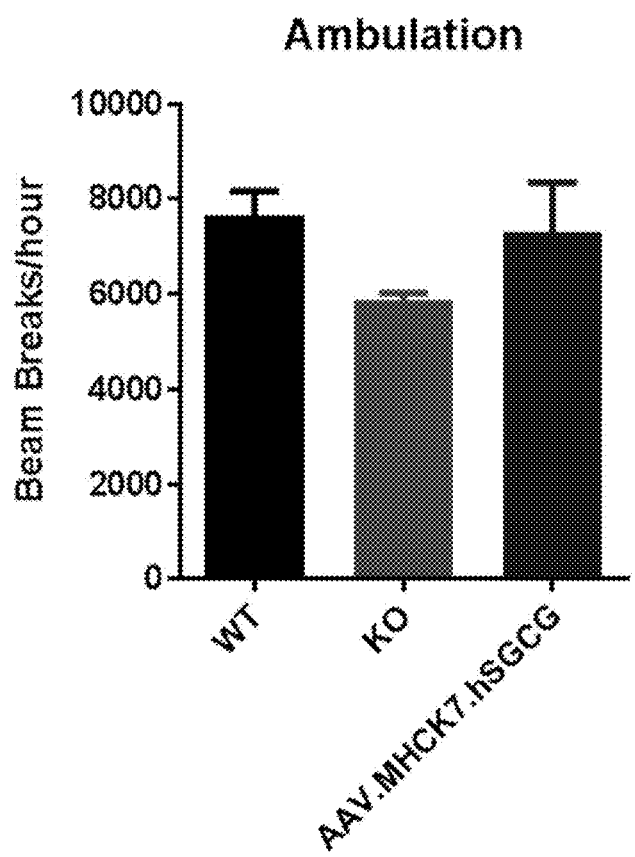
FIG. 12 shows laser monitoring of open-field cage activity. Overall ambulation in x and y planes is decreased in SGCG−/− mice and improved in AAV.MCHK7.hSGCG treated mice. BL6 WT (n=6), untreated SGCG−/− (n=6), and AAV.MHCK7.hSGCG treated (n=5).

In order to further test potential functional benefits resulting from a systemic delivery of a therapeutic hSGCG transgene and ultimately improving the disease phenotype of SGCG−/− mice, laser-monitoring of open-field cage activity was performed on all groups of mice. The graph in FIG. 12 depicts a decrease of 23.64% in total ambulation in x and y planes in SGCG−/− mice compared to normal BL6 WT (BL6 WT: 7655.42 beam breaks/hr vs. SGCG−/−: 5846.00 beam breaks/hr). scAAVrh.74.MHCK7.hSGCG treated mice were overall more active compared to SGCG−/− mice by qualitative observation, and a quantitative measurement of the open-field cage activity showed a 24.90% increase in ambulation (SGCG−/−: 5846.00 beam breaks/hr vs Treated: 7301.80 beam breaks/hr). The detailed values for each parameter in individual mice were also measured.

Example 7: Toxicology and Vector Biodistribution

The purpose of this study was to assess any potential toxicity or safety concerns of hSGCG gene therapy in SGCG−/− mice at 3 months after delivery of the test article scAAVrh.74.MHCK7.hSGCG, utilizing the same animals described above. Test article was given to 5 SGCG−/− at $1.0 \times 10^{13}$ vg total dose ($5 \times 10^{14}$ vg/kg) by the intravenous (IV) route in a volume of 460 µL split into two separate 230 µL injections, morning and afternoon, at 4 weeks of age. Six uninjected SGCG−/− mice served as untreated diseased controls, and 5 C57BL/6 WT mice served as normal healthy controls (TABLE 6). Full necropsies were performed on all mice to extract six skeletal muscles (TA, GAS, QUAD, GLUT, PSOAS, and TRI), both left and right side, along with the diaphragm and heart, as well as internal organs including the lungs, kidneys, liver, spleen, and gonads. To assess the safety of our vector, hematoxylin & eosin staining was performed on cryosections of the muscle tissue and all organs harvested were formalin fixed and also stained with hematoxylin & eosin. These sections were then formally reviewed for toxicity by an independent veterinary pathologist and no adverse effects were detected, and the results are summarized below in TABLE 7 and the detailed histopathology report was also prepared. Quantitative PCR was performed to assess vector biodistribution and those results are shown below in TABLE 7 and FIG. 13.

Histopathology Review of Vector Transduced Tissue

In order to determine the safety and toxicology profile of scAAVrh.74.MHCK7.hSGCG using systemic delivery, all skeletal muscles including the diaphragm, along with the heart and five other organs harvested from the group of vector dosed SGCG−/− mice and controls from this preclinical study were stained with H&E and sections of each tissue were formally reviewed by an independent veterinary pathologist. Group details and study design are shown in TABLE 6.

TABLE 6

Summary of Cohorts for scAAVrh.74.MHCK7.hSGCG Gene Transfer Histopathology Review

| | Genotype | Cohort | Dose (vg) | Sex | Age at Injection | Age at Necropsy | Time on Treatment |
|---|---|---|---|---|---|---|---|
| 1 | SGCG−/− | Test Article | $1.0 \times 10^{13}$ | Female | 1 month | 4 months | 3 months |
| | | | | Female | 1 month | 4 months | 3 months |
| | | | | Female | 1 month | 4 months | 3 months |
| | | | | Female | 1 month | 4 months | 3 months |
| | | | | Female | 1 month | 4 months | 3 months |
| 2 | BL6 WT | Vehicle Control | LRS | Male | 1 month | 4 months | 3 months |
| | | | | Male | 1 month | 4 months | 3 months |
| | | | | Male | 1 month | 4 months | 3 months |
| | | | | Male | 1 month | 4 months | 3 months |
| | | | | Male | 1 month | 4 months | 3 months |
| 3 | SGCG−/− | Disease Control | N/A | Female | N/A | 4 months | N/A |
| | | | | Female | N/A | 4 months | N/A |
| | | | | Male | N/A | 4 months | N/A |
| | | | | Male | N/A | 4 months | N/A |

In summary, IV injection of scAAVrh.74.MHCK7.hSGCG did not elicit any microscopic changes in myofibers of any skeletal muscles examined (TABLE 7). In addition, no treatment-related lesions were seen in any of the tissues evaluated histologically, indicating the test article was well tolerated, see full report in Appendix J (Report No. AAVrh74-SGCG-MOUSE-001.1). Any changes noted were seen in both treated and control mice and were considered incidental findings. Furthermore, the independent review indicated that relative to reference specimens from control mice, administration of the test article scAAVrh.74.MHCK7.hSGCG substantially reduced myofiber atrophy, degeneration, and destruction, suggesting the vector can ameliorate the degree of myopathy associated with the absence of SGCG in diseased mice.

TABLE 7

Histopathology Results scAAVrh.74.MHCK7.hSGCG Safety Study in SGCG−/− Mice

| Test Article (vector dose) | Age at Injection | Treatment Length | Tissues Analyzed | Formal Histopath |
|---|---|---|---|---|
| scAAVrh.74.MHCK7.hSGCG (1e13vg total dose-5e14 vg/kg) 5 animals analyzed | 1 month | 3 months | Skeletal Muscles, Heart, Lungs, Kidney, Liver, Spleen, Gonads | No Findings |

Vector Genome Biodistribution

Figure 13:
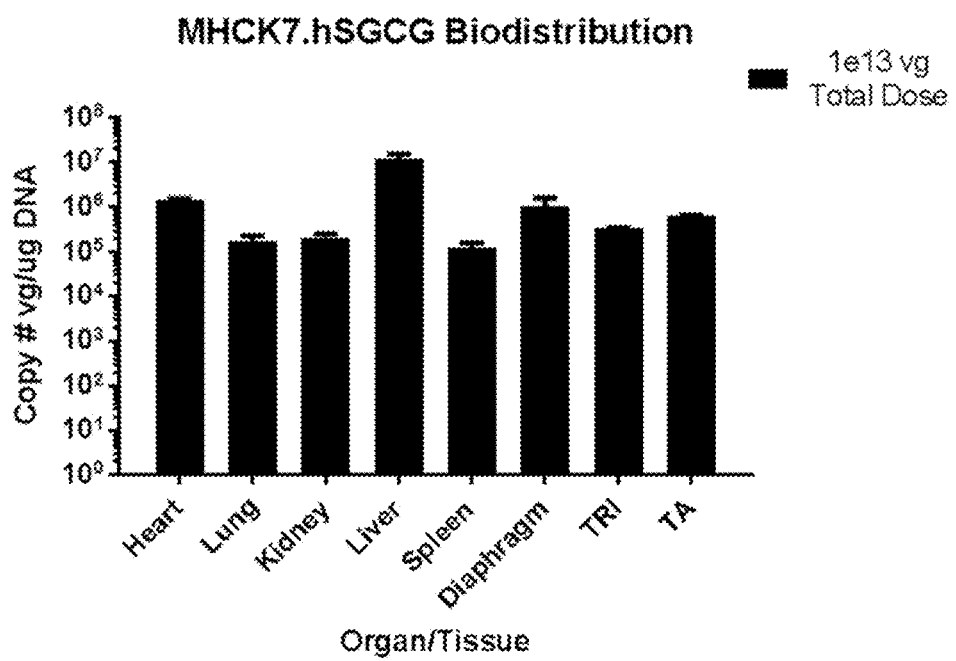
FIG. 13 shows biodistribution of vector genomes. Vector genome distribution of average vg copies per microgram genomic DNA (gDNA) were measured in various tissues from two SGCG−/− mice 3 months after IV delivery of 1e13 vg total dose of s cAAVrh. 74.MHCK7.hSGC G.

The presence of test article-specific DNA sequences was examined using a real time, quantitative PCR assay (qPCR). Biodistribution analysis was performed on tissue samples collected from two vector dosed SGCG−/− animals. A positive signal is anything equal to or greater than 100 single-stranded DNA copies/µg genomic DNA detected. Tissues were harvested at necropsy and vector specific primer probe sets specific for sequences of the MHCK7 promoter were utilized. TABLE 8 and FIG. 13 depict the vector genome copies detected in each tissue sample from scAAVrh.74.MHCK7.hSGCG injected mice.

scAAVrh.74.MHCK7.hSGCG transcript was detected at varying levels in all collected tissues. As expected, while vector was detected at high levels in the liver due to the nature of the intravenous delivery route, the highest levels were seen in skeletal muscle and the heart. The lowest levels were detected in the lungs, kidney, and spleen. These data indicate that the test article was efficiently delivered into all investigated tissues of vector dosed mice.

TABLE 8

Quantitative PCR Results Following High Dose scAAVrh.74.MHCK7.hSGCG Systemic Delivery in SGCG-/- Mice

| Tissue | Vector genome copies/µg | |
|---|---|---|
| | 5229 | 5231 |
| Heart | 1.56E+06 | 1.30E+06 |
| Lung | 1.15E+05 | 2.29E+05 |
| Kidney | 1.74E+05 | 2.48E+05 |
| Liver | 9.23E+06 | 1.50E+07 |
| Spleen | 1.58E+05 | 9.05E+04 |
| Diaphragm | 4.63E+05 | 1.60E+06 |
| TRI | 3.35E+05 | 3.48E+05 |
| TA | 6.23E+05 | 6.70E+05 |

Analysis of Serum Chemistries

To further evaluate liver function, Applicant assessed the levels of two liver enzymes that are normal serum chemistry parameters, alkaline aminotransferase (ALT) and aspartate aminotransferase (AST). Elevation of either of these enzymes can be indicative of hepatocyte damage and impaired liver function. Applicant analyzed the serum from all 6 C57BL/6 WT mice, all 6 untreated SGCG−/− mice, and all 5 scAAVrh.74.MHCK7.hSGCG dosed mice. FIG. 14A show an elevation of ALT in untreated SGCG−/− mice to double the levels seen in healthy BL6 WT mice (BL6 WT: 44.20 U/L vs. SGCG−/−: 89.00 U/L). IV delivery of the scAAVrh.74.MHCK7.hSGCG to SGCG−/− mice resulted in a 32.02% decrease in ALT levels (SGCG−/−: 89.00 U/L vs. Treated: 60.50 U/L). FIG. 14B shows AST levels in all three groups of mice indicated a significant elevation of 113.27% in untreated SGCG−/− mice (BL6 WT: 326.00 U/L vs. SGCG−/−: 695.25 U/L). These AST levels were reduced by 41.10% following systemic delivery of scAAVrh.74.MHCK7.hSGCG (FIG. 14B). Taken together, while liver enzymes considered to be biomarkers of liver damage are elevated in diseased SGCG−/− mice, systemic hSGCG gene transfer in SGCG−/− diseased mice normalizes the levels of both ALT and AST. Individual values for each enzyme in all mice were determined.

In conclusion, systemic delivery of two different doses of the AAV virus carrying the hSGCB transgene was shown to be safe and non-toxic. Doses tested include $1.2 \times 10^{13}$ vg total dose ($6.0 \times 10^{14}$ vg/kg) and $1.0 \times 10^{13}$ vg total dose ($5.0 \times 10^{14}$ vg/kg). In particular, systemic delivery of a high dose ($1.0 \times 10^{13}$ vg total dose—$5.0 \times 10^{14}$ vg/kg) of scAAVrh.74.MHCK7.hSGCG through the tail vein of SGCG−/− is safe and effective in restoring γ-sarcoglycan expression and reversing dystrophic histopathology in diseased muscle.

---

What is claimed:

1. A recombinant AAV (rAAV) vector comprising an AAV capsid and a gene expression cassette comprising a polynucleotide sequence encoding γ-sarcoglycan and a muscle specific control element, wherein the polynucleotide sequence encoding γ-sarcoglycan is under the transcriptional control of the muscle specific control element, wherein the polynucleotide sequence comprises a nucleotide sequence at least 95% identical to SEQ ID NO: 1 or SEQ ID NO: 3.

2. The rAAV vector of claim 1, wherein the rAAV vector: comprises a self-complementary AAV vector genome; comprises a genome lacking AAV rep and cap DNA; is of the serotype AAV1, AAV2, AAV4, AAVS, AAV6, AAV, AAV8, AAVO, AAVIO, AAVI11, AAV12, AAV13, AAV rh74, or a variant thereof.

3. The rAAV vector of claim 2, wherein the rAAV vector is of the AAV rh74 serotype and comprises the amino acid sequence set forth in SEQ ID NO:10.

4. The rAAV vector of claim 1, wherein the polynucleotide encoding γ-sarcoglycan is operatively linked to the muscle-specific control element.

5. The rAAV vector of claim 4, wherein the muscle-specific control element is selected from the group consisting of human skeletal actin gene element, cardiac actin gene element, myocyte-specific enhancer binding factor mef element, muscle creatine kinase (MCK) promoter, truncated MCK (tMCK) promoter, myosin heavy chain (MHC) element, MHCK7 promoter, C5-12, murine creatine kinase enhancer element, skeletal fast-twitch troponin c gene element, slow-twitch cardiac troponin c gene element, the slow-twitch troponin I gene element, hypoxia-inducible nuclear factors, steroid-inducible element, and glucocorticoid response element (gre).

6. The rAAV vector of claim 1, wherein the muscle specific control element is an MHCK7 promoter.

7. The rAAV vector of claim 6, wherein the MHCK promoter comprises the nucleotide sequence set forth in SEQ ID NO: 4.

8. The rAAV vector of claim 1, wherein the rAAV vector comprises an intron comprising the nucleotide sequence set forth in SEQ ID NO: 5.

9. The rAAV vector of claim 1, wherein the polynucleotide sequence encoding γ-sarcoglycan comprises a nucleotide sequence at least 95% identical to SEQ ID NO: 1 encodes the amino acid sequence of SEQ ID NO: 2.

10. A method of treating γ-sarcoglycanopathy in a subject, comprising administering to the subject a therapeutically effective amount of a recombinant adeno-associated virus (AAV) vector of claim 1.

11. The rAAV vector of claim 1, wherein the polynucleotide sequence encoding γ-sarcoglycan comprises the nucleotide sequence set forth in SEQ ID NO: 1.

12. The rAAV vector of claim 1, wherein the capsid is of the serotype AAV1, AAV2, AAV4, AAV5, AAV6, AAV7, AAV8, AAV9, AAV10, AAV11, AAV12, AAV13, AAV rh74, or a variant thereof.

13. A composition comprising the rAAV vector of claim 1.

14. A host cell, comprising an rAAV vector of claim 1.

15. A combination therapy, comprising the composition of claim 13 and a corticosteroid.

16. A kit, comprising the composition of claim 13 and a corticosteroid.

17. The rAAV vector of claim 1, wherein the polynucleotide sequence encoding γ-sarcoglycan comprises the nucleotide sequence set forth in SEQ ID NO: 3.

* * * * *

UNITED STATES PATENT AND TRADEMARK OFFICE
CERTIFICATE OF CORRECTION

Page 1 of 1

PATENT NO. : 12,263,230 B2
APPLICATION NO. : 16/966407
DATED : April 1, 2025
INVENTOR(S) : Louise R. Rodino-Klapac It is certified that error appears in the above-identified patent and that said Letters Patent is hereby corrected as shown below:

In the Claims

Claim 2, Column 55, Line 39 should read:
serotype AAV1, AAV2, AAV4, AAV5, AAV6, AAV7, AAV8, Claim 2, Column 55, Line 40 should read:
AAV9, AAV10, AAV11, AAV12, AAV13, AAV rh74, or a Signed and Sealed this
Twenty-sixth Day of August, 2025

Coke Morgan Stewart
*Acting Director of the United States Patent and Trademark Office*